US012557916B2

(12) United States Patent
Sohn et al.

(10) Patent No.: US 12,557,916 B2
(45) Date of Patent: Feb. 24, 2026

(54) BED SYSTEM FOR DETECTING SNORE SIDE

(71) Applicant: Sleep Number Corporation, Minneapolis, MN (US)

(72) Inventors: Kwanghyun Sohn, San Jose, CA (US); Saeed Babaeizadeh, Arlington, MA (US); Yong Li, San Jose, CA (US)

(73) Assignee: Sleep Number Corporation, Minneapolis, MN (US)

( * ) Notice: Subject to any disclaimer, the term of this patent is extended or adjusted under 35 U.S.C. 154(b) by 18 days.

(21) Appl. No.: 18/639,292

(22) Filed: Apr. 18, 2024

(65) Prior Publication Data

US 2024/0349905 A1 Oct. 24, 2024

Related U.S. Application Data

(60) Provisional application No. 63/460,697, filed on Apr. 20, 2023.

(51) Int. Cl.
| | |
|---|---|
| *A47C 27/08* | (2006.01) |
| *A61B 5/00* | (2006.01) |
| (Continued) | |

(52) U.S. Cl.
CPC ........ *A47C 27/083* (2013.01); *A61B 5/02055* (2013.01); *A61B 5/4815* (2013.01);
(Continued)

(58) Field of Classification Search
CPC . A47C 27/083; A61B 5/02055; A61B 5/4815; A61B 2562/0204;
(Continued)

(56) References Cited

U.S. PATENT DOCUMENTS

| | | | |
|---|---|---|---|
| 3,727,606 | A | 4/1973 | Sielaff |
| 3,998,209 | A | 12/1976 | Macvaugh |

(Continued)

FOREIGN PATENT DOCUMENTS

| | | |
|---|---|---|
| CN | 1557270 | 12/2004 |
| CN | 101224149 | 7/2008 |

(Continued)

OTHER PUBLICATIONS

U.S. Appl. No. 16/719,177, Nunn et al., Dec. 18, 2019.
(Continued)

*Primary Examiner* — Daryl C Pope
(74) *Attorney, Agent, or Firm* — Fish & Richardson P.C.

(57) ABSTRACT

This document generally describes bed systems for automatically determining which side of a bed a detected snore originates from, where two sleepers are in the bed. A bed system can include sensors for collecting acoustic readings and pressure readings, on respective sides of the bed. The collected sensor readings can be processed by a computer system to determine whether a snore is detected at the bed system and which side of the bed system the snore originates from. Based on the determination of the snorer side of the bed system, the computer system can also generate one or more actions, which can be used to mitigate, reduce, or otherwise stop the snoring on the determined snorer side of the bed system.

20 Claims, 28 Drawing Sheets

(51) Int. Cl.
　　*A61B 5/0205* 　　　　(2006.01)
　　*G06N 20/00* 　　　　(2019.01)
(52) U.S. Cl.
　　CPC ...... *G06N 20/00* (2019.01); *A61B 2562/0204*
　　　　　　　(2013.01); *A61B 2562/0247* (2013.01)
(58) Field of Classification Search
　　CPC .......... A61B 2562/0247; A61B 5/7267; A61B
　　　　　　5/113; A61B 5/4818; A61B 5/6891; A61B
　　　　　　　　　　　　　5/6892; G06N 20/00
　　See application file for complete search history.

(56) References Cited

U.S. PATENT DOCUMENTS

| | | | |
|---|---|---|---|
| 4,146,885 A | 3/1979 | Lawson, Jr. |
| 4,299,233 A | 11/1981 | Lemelson |
| 4,657,026 A | 4/1987 | Tagg |
| 4,662,012 A | 5/1987 | Tarbet |
| 4,766,628 A | 8/1988 | Walker |
| 4,788,729 A | 12/1988 | Walker |
| 4,829,616 A | 5/1989 | Walker |
| 4,890,344 A | 1/1990 | Walker |
| 4,897,890 A | 2/1990 | Walker |
| 4,908,895 A | 3/1990 | Walker |
| 4,982,466 A | 1/1991 | Higgins et al. |
| 4,991,244 A | 2/1991 | Walker |
| 5,020,176 A | 6/1991 | Dotson |
| 5,062,169 A | 11/1991 | Kennedy et al. |
| 5,144,706 A | 9/1992 | Walker et al. |
| 5,170,522 A | 12/1992 | Walker |
| 5,197,490 A | 3/1993 | Steiner et al. |
| 5,459,452 A | 10/1995 | DePonte |
| 5,487,196 A | 1/1996 | Wilkinson et al. |
| 5,509,154 A | 4/1996 | Shafer et al. |
| 5,515,865 A | 5/1996 | Scanlon |
| 5,551,418 A | 9/1996 | Estes |
| 5,564,140 A | 10/1996 | Shoenhair et al. |
| 5,642,546 A | 7/1997 | Shoenhair |
| 5,652,484 A | 7/1997 | Shafer et al. |
| 5,675,855 A | 10/1997 | Culp |
| 5,684,460 A | 11/1997 | Scanlon |
| 5,699,038 A | 12/1997 | Ulrich et al. |
| 5,724,990 A | 3/1998 | Ogino |
| 5,765,246 A | 6/1998 | Shoenhair |
| 5,771,511 A | 6/1998 | Kummer et al. |
| 5,796,340 A | 8/1998 | Miller |
| 5,844,488 A | 12/1998 | Musick |
| 5,848,450 A | 12/1998 | Oexman et al. |
| 5,903,941 A | 5/1999 | Shafer et al. |
| 5,904,172 A | 5/1999 | Gifft et al. |
| 5,948,303 A | 9/1999 | Larson |
| 5,964,720 A | 10/1999 | Pelz |
| 5,989,193 A | 11/1999 | Sullivan |
| 6,024,699 A | 2/2000 | Surwit et al. |
| 6,037,723 A | 3/2000 | Shafer et al. |
| 6,058,537 A | 5/2000 | Larson |
| 6,062,216 A | 5/2000 | Corn |
| 6,079,065 A | 6/2000 | Luff et al. |
| 6,094,762 A | 8/2000 | Viard et al. |
| 6,108,844 A | 8/2000 | Kraft et al. |
| 6,120,441 A | 9/2000 | Griebel |
| 6,146,332 A | 11/2000 | Pinsonneault et al. |
| 6,147,592 A | 11/2000 | Ulrich et al. |
| 6,161,231 A | 12/2000 | Kraft et al. |
| 6,202,239 B1 | 3/2001 | Ward et al. |
| 6,208,250 B1 | 3/2001 | Dixon et al. |
| 6,234,642 B1 | 5/2001 | Bokaemper |
| 6,272,378 B1 | 8/2001 | Baumgart-Schmitt |
| 6,386,201 B1 | 5/2002 | Fard |
| 6,396,224 B1 | 5/2002 | Luff et al. |
| 6,397,419 B1 | 6/2002 | Mechache |
| 6,438,776 B2 | 8/2002 | Ferrand et al. |
| 6,450,957 B1 | 9/2002 | Yoshimi et al. |
| 6,468,234 B1 | 10/2002 | Ford et al. |
| 6,483,264 B1 | 11/2002 | Shafer et al. |
| 6,485,441 B2 | 11/2002 | Woodward |
| 6,546,580 B2 | 4/2003 | Shimada |
| 6,547,743 B2 | 4/2003 | Brydon |
| 6,561,047 B1 | 5/2003 | Gladney |
| 6,566,833 B2 | 5/2003 | Bartlett |
| 6,643,875 B2 | 11/2003 | Boso et al. |
| 6,686,711 B2 | 2/2004 | Rose et al. |
| 6,698,432 B2 | 3/2004 | Ek |
| 6,708,357 B2 | 3/2004 | Gaboury et al. |
| 6,719,708 B1 | 4/2004 | Jansen |
| 6,763,541 B2 | 7/2004 | Mahoney et al. |
| 6,778,090 B2 | 8/2004 | Newham |
| 6,804,848 B1 | 10/2004 | Rose |
| 6,832,397 B2 | 12/2004 | Gaboury et al. |
| 6,840,117 B2 | 1/2005 | Hubbard, Jr. |
| 6,840,907 B1 | 1/2005 | Brydon |
| 6,847,301 B1 | 1/2005 | Olson |
| 6,878,121 B2 | 4/2005 | Krausman |
| 6,883,191 B2 | 4/2005 | Gaboury et al. |
| 6,993,380 B1 | 1/2006 | Modarres |
| 7,041,049 B1 | 5/2006 | Raniere |
| 7,077,810 B2 | 7/2006 | Lange et al. |
| 7,150,718 B2 | 12/2006 | Okada |
| 7,237,287 B2 | 7/2007 | Weismiller et al. |
| 7,253,366 B2 | 8/2007 | Bhai |
| 7,304,580 B2 | 12/2007 | Sullivan et al. |
| 7,314,451 B2 | 1/2008 | Halperin et al. |
| 7,321,811 B1 | 1/2008 | Rawls-Meehan |
| 7,330,127 B2 | 2/2008 | Price et al. |
| 7,387,124 B2 | 6/2008 | Noda et al. |
| 7,389,554 B1 | 6/2008 | Rose |
| 7,396,331 B2 | 7/2008 | Mack |
| 7,429,247 B2 | 9/2008 | Okada et al. |
| 7,437,787 B2 | 10/2008 | Bhai |
| 7,465,280 B2 | 12/2008 | Rawls-Meehan |
| 7,480,951 B2 | 1/2009 | Weismiller |
| 7,506,390 B2 | 3/2009 | Dixon et al. |
| 7,513,003 B2 | 4/2009 | Mossbeck |
| 7,520,006 B2 | 4/2009 | Menkedick et al. |
| 7,524,279 B2 | 4/2009 | Auphan |
| 7,532,934 B2 | 5/2009 | Lee et al. |
| 7,538,659 B2 | 5/2009 | Ulrich |
| 7,568,246 B2 | 8/2009 | Weismiller et al. |
| 7,631,377 B1 | 12/2009 | Sanford |
| 7,637,859 B2 | 12/2009 | Lindback et al. |
| 7,652,581 B2 | 1/2010 | Gentry et al. |
| 7,666,151 B2 | 2/2010 | Sullivan et al. |
| 7,669,263 B2 | 3/2010 | Menkedick et al. |
| 7,676,872 B2 | 3/2010 | Block et al. |
| 7,685,663 B2 | 3/2010 | Rawls-Meehan |
| 7,698,761 B2 | 4/2010 | Neuenswander et al. |
| 7,699,784 B2 | 4/2010 | Wan et al. |
| 7,717,848 B2 | 5/2010 | Heruth et al. |
| 7,749,154 B2 | 7/2010 | Cornel |
| 7,784,128 B2 | 8/2010 | Kramer |
| 7,785,257 B2 | 8/2010 | Mack et al. |
| 7,805,785 B2 | 10/2010 | Rawls-Meehan |
| 7,841,031 B2 | 11/2010 | Rawls-Meehan |
| 7,849,545 B2 | 12/2010 | Flocard et al. |
| 7,854,031 B2 | 12/2010 | Rawls-Meehan |
| 7,860,723 B2 | 12/2010 | Rawls-Meehan |
| 7,862,523 B2 | 1/2011 | Ruotoistenmaki |
| 7,865,988 B2 | 1/2011 | Koughan et al. |
| 7,868,757 B2 | 1/2011 | Radivojevic et al. |
| 7,869,903 B2 | 1/2011 | Turner et al. |
| 7,930,783 B2 | 4/2011 | Rawls-Meehan |
| 7,933,669 B2 | 4/2011 | Rawls-Meehan |
| 7,953,613 B2 | 5/2011 | Gizewski |
| 7,954,189 B2 | 6/2011 | Rawls-Meehan |
| 7,956,755 B2 | 6/2011 | Lee et al. |
| 7,967,739 B2 | 6/2011 | Auphan |
| 7,979,169 B2 | 7/2011 | Rawls-Meehan |
| 8,019,486 B2 | 9/2011 | Rawls-Meehan |
| 8,020,230 B2 | 9/2011 | Rawls-Meehan |
| 8,028,363 B2 | 10/2011 | Rawls-Meehan |
| 8,032,263 B2 | 10/2011 | Rawls-Meehan |
| 8,032,960 B2 | 10/2011 | Rawls-Meehan |
| 8,046,114 B2 | 10/2011 | Rawls-Meehan |

(56)                    References Cited

U.S. PATENT DOCUMENTS

| | | |
|---|---|---|
| 8,046,115 B2 | 10/2011 | Rawls-Meehan |
| 8,046,116 B2 | 10/2011 | Rawls-Meehan |
| 8,046,117 B2 | 10/2011 | Rawls-Meehan |
| 8,050,805 B2 | 11/2011 | Rawls-Meehan |
| 8,052,612 B2 | 11/2011 | Tang |
| 8,065,764 B2 | 11/2011 | Kramer |
| 8,069,852 B2 | 12/2011 | Burton |
| 8,073,535 B2 | 12/2011 | Jung et al. |
| 8,078,269 B2 | 12/2011 | Suzuki et al. |
| 8,078,336 B2 | 12/2011 | Rawls-Meehan |
| 8,078,337 B2 | 12/2011 | Rawls-Meehan |
| 8,083,682 B2 | 12/2011 | Dalal et al. |
| 8,090,478 B2 | 1/2012 | Skinner et al. |
| 8,092,399 B2 | 1/2012 | Sasaki |
| 8,094,013 B1 | 1/2012 | Lee |
| 8,096,960 B2 | 1/2012 | Loree et al. |
| 8,144,001 B1 | 3/2012 | D'Souza |
| 8,146,191 B2 | 4/2012 | Bobey et al. |
| 8,150,562 B2 | 4/2012 | Rawls-Meehan |
| 8,166,589 B2 | 5/2012 | Hijlkema |
| 8,177,724 B2 | 5/2012 | Derchak et al. |
| 8,181,290 B2 | 5/2012 | Brykalski et al. |
| 8,181,296 B2 | 5/2012 | Rawls-Meehan |
| 8,266,742 B2 | 9/2012 | Andrienko |
| 8,272,892 B2 | 9/2012 | McNeely et al. |
| 8,276,585 B2 | 10/2012 | Buckley |
| 8,279,057 B2 | 10/2012 | Hirose |
| 8,280,748 B2 | 10/2012 | Allen |
| 8,281,433 B2 | 10/2012 | Riley et al. |
| 8,282,452 B2 | 10/2012 | Grigsby et al. |
| 8,284,047 B2 | 10/2012 | Collins, Jr. |
| 8,287,452 B2 | 10/2012 | Young et al. |
| 8,336,369 B2 | 12/2012 | Mahoney |
| 8,341,784 B2 | 1/2013 | Scott |
| 8,341,786 B2 | 1/2013 | Oexman et al. |
| 8,348,840 B2 | 1/2013 | Heit et al. |
| 8,350,709 B2 | 1/2013 | Receveur |
| 8,375,488 B2 | 2/2013 | Rawls-Meehan |
| 8,376,954 B2 | 2/2013 | Lange et al. |
| 8,382,484 B2 | 2/2013 | Wetmore et al. |
| 8,386,008 B2 | 2/2013 | Yuen et al. |
| 8,398,538 B2 | 3/2013 | Dothie |
| 8,403,865 B2 | 3/2013 | Halperin et al. |
| 8,413,274 B2 | 4/2013 | Weismiller et al. |
| 8,421,606 B2 | 4/2013 | Collins, Jr. et al. |
| 8,428,696 B2 | 4/2013 | Foo |
| 8,444,558 B2 | 5/2013 | Young et al. |
| 8,491,492 B2 | 7/2013 | Shinar et al. |
| 8,517,953 B2 | 8/2013 | Lange et al. |
| 8,620,615 B2 | 12/2013 | Oexman |
| 8,672,853 B2 | 3/2014 | Young |
| 8,679,034 B2 | 3/2014 | Halperin et al. |
| 8,769,747 B2 | 7/2014 | Mahoney et al. |
| 8,832,887 B2 | 9/2014 | Mossbeck |
| 8,840,564 B2 | 9/2014 | Pinhas et al. |
| 8,909,357 B2 | 12/2014 | Rawls-Meehan |
| 8,931,329 B2 | 1/2015 | Mahoney et al. |
| 8,966,689 B2 | 3/2015 | McGuire et al. |
| 8,973,183 B1 | 3/2015 | Palashewski et al. |
| 8,984,687 B2 | 3/2015 | Stusynski et al. |
| 9,370,457 B2 | 6/2016 | Nunn |
| 9,392,879 B2 | 7/2016 | Nunn et al. |
| 9,445,751 B2 | 9/2016 | Young et al. |
| 9,504,416 B2 | 11/2016 | Young et al. |
| 9,510,688 B2 | 12/2016 | Nunn et al. |
| 9,635,953 B2 | 5/2017 | Nunn et al. |
| 9,770,114 B2 | 9/2017 | Brosnan et al. |
| 9,844,275 B2 | 12/2017 | Nunn et al. |
| 9,931,085 B2 | 4/2018 | Young et al. |
| 10,058,467 B2 | 8/2018 | Stusynski et al. |
| 10,092,242 B2 | 10/2018 | Nunn et al. |
| 10,149,549 B2 | 12/2018 | Erko et al. |
| 10,182,661 B2 | 1/2019 | Nunn et al. |
| 10,201,234 B2 | 2/2019 | Nunn et al. |
| 10,251,490 B2 | 4/2019 | Nunn et al. |
| 10,342,358 B1 | 7/2019 | Palashewski et al. |
| 10,441,086 B2 | 10/2019 | Nunn et al. |
| 10,441,087 B2 | 10/2019 | Karschnik et al. |
| 10,448,749 B2 | 10/2019 | Palashewski et al. |
| 10,492,969 B2 | 12/2019 | Stusynski et al. |
| 10,632,032 B1 | 4/2020 | Stusynski et al. |
| 10,646,050 B2 | 5/2020 | Nunn et al. |
| 10,674,832 B2 | 6/2020 | Brosnan et al. |
| 10,716,512 B2 | 7/2020 | Erko et al. |
| 10,729,255 B2 | 8/2020 | Erko et al. |
| 10,736,432 B2 | 8/2020 | Brosnan et al. |
| 10,750,875 B2 | 8/2020 | Palashewski et al. |
| 10,827,846 B2 | 11/2020 | Karschnik et al. |
| 10,881,219 B2 | 1/2021 | Nunn et al. |
| 10,898,717 B2 | 1/2021 | Mashiach et al. |
| 10,957,335 B2 | 3/2021 | Demirli et al. |
| 10,959,535 B2 | 3/2021 | Karschnik et al. |
| D916,745 S | 4/2021 | Stusynski et al. |
| 10,980,351 B2 | 4/2021 | Nunn et al. |
| 11,096,849 B2 | 8/2021 | Stusynski et al. |
| 11,122,909 B2 | 9/2021 | Palashewski et al. |
| 11,160,683 B2 | 11/2021 | Nunn et al. |
| 11,206,929 B2 | 12/2021 | Palashewski et al. |
| 11,298,075 B2 | 4/2022 | Paalasmaa et al. |
| D954,725 S | 6/2022 | Stusynski et al. |
| D968,436 S | 11/2022 | Stusynski et al. |
| D975,121 S | 1/2023 | Stusynski et al. |
| D1,000,464 S | 10/2023 | Stusynski et al. |
| D1,018,476 S | 3/2024 | Dixon et al. |
| 12,029,322 B2 | 7/2024 | Hill et al. |
| 2002/0124311 A1 | 9/2002 | Peftoulidis |
| 2002/0184711 A1 | 12/2002 | Mahoney et al. |
| 2002/0189621 A1 | 12/2002 | Ek |
| 2003/0045806 A1 | 3/2003 | Brydon |
| 2003/0128125 A1 | 7/2003 | Burbank et al. |
| 2003/0163874 A1 | 9/2003 | Boso et al. |
| 2003/0166995 A1 | 9/2003 | Jansen |
| 2003/0182728 A1 | 10/2003 | Chapman et al. |
| 2003/0221261 A1 | 12/2003 | Tarbet et al. |
| 2004/0049132 A1 | 3/2004 | Barron et al. |
| 2005/0022606 A1 | 2/2005 | Partin et al. |
| 2005/0038326 A1 | 2/2005 | Mathur |
| 2005/0115561 A1 | 6/2005 | Stahmann et al. |
| 2005/0190065 A1 | 9/2005 | Ronholm |
| 2005/0190068 A1 | 9/2005 | Gentry et al. |
| 2005/0283039 A1 | 12/2005 | Cornel |
| 2006/0020178 A1 | 1/2006 | Sotos et al. |
| 2006/0031996 A1 | 2/2006 | Rawls-Meehan |
| 2006/0047217 A1 | 3/2006 | Mirtalebi |
| 2006/0152378 A1 | 7/2006 | Lokhorst |
| 2006/0162074 A1 | 7/2006 | Bader |
| 2007/0049842 A1 | 3/2007 | Hill et al. |
| 2007/0118054 A1 | 5/2007 | Pinhas et al. |
| 2007/0149883 A1 | 6/2007 | Yesha |
| 2007/0179334 A1 | 8/2007 | Groves et al. |
| 2007/0180047 A1 | 8/2007 | Dong et al. |
| 2007/0180618 A1 | 8/2007 | Weismiller et al. |
| 2007/0276202 A1 | 11/2007 | Raisanen et al. |
| 2008/0052837 A1 | 3/2008 | Blumberg |
| 2008/0071200 A1 | 3/2008 | Rawls-Meehan |
| 2008/0077020 A1 | 3/2008 | Young et al. |
| 2008/0092291 A1 | 4/2008 | Rawls-Meehan |
| 2008/0092292 A1 | 4/2008 | Rawls-Meehan |
| 2008/0092293 A1 | 4/2008 | Rawls-Meehan |
| 2008/0092294 A1 | 4/2008 | Rawls-Meehan |
| 2008/0093784 A1 | 4/2008 | Rawls-Meehan |
| 2008/0097774 A1 | 4/2008 | Rawls-Meehan |
| 2008/0097778 A1 | 4/2008 | Rawls-Meehan |
| 2008/0097779 A1 | 4/2008 | Rawls-Meehan |
| 2008/0104750 A1 | 5/2008 | Rawls-Meehan |
| 2008/0104754 A1 | 5/2008 | Rawls-Meehan |
| 2008/0104755 A1 | 5/2008 | Rawls-Meehan |
| 2008/0104756 A1 | 5/2008 | Rawls-Meehan |
| 2008/0104757 A1 | 5/2008 | Rawls-Meehan |
| 2008/0104758 A1 | 5/2008 | Rawls-Meehan |
| 2008/0104759 A1 | 5/2008 | Rawls-Meehan |
| 2008/0104760 A1 | 5/2008 | Rawls-Meehan |
| 2008/0104761 A1 | 5/2008 | Rawls-Meehan |
| 2008/0109959 A1 | 5/2008 | Rawls-Meehan |

(56) References Cited

U.S. PATENT DOCUMENTS

| | | |
|---|---|---|
| 2008/0109964 A1 | 5/2008 | Flocard et al. |
| 2008/0109965 A1 | 5/2008 | Mossbeck |
| 2008/0115272 A1 | 5/2008 | Rawls-Meehan |
| 2008/0115273 A1 | 5/2008 | Rawls-Meehan |
| 2008/0115274 A1 | 5/2008 | Rawls-Meehan |
| 2008/0115275 A1 | 5/2008 | Rawls-Meehan |
| 2008/0115276 A1 | 5/2008 | Rawls-Meehan |
| 2008/0115277 A1 | 5/2008 | Rawls-Meehan |
| 2008/0115278 A1 | 5/2008 | Rawls-Meehan |
| 2008/0115279 A1 | 5/2008 | Rawls-Meehan |
| 2008/0115280 A1 | 5/2008 | Rawls-Meehan |
| 2008/0115281 A1 | 5/2008 | Rawls-Meehan |
| 2008/0115282 A1 | 5/2008 | Rawls-Meehan |
| 2008/0120775 A1 | 5/2008 | Rawls-Meehan |
| 2008/0120776 A1 | 5/2008 | Rawls-Meehan |
| 2008/0120777 A1 | 5/2008 | Rawls-Meehan |
| 2008/0120778 A1 | 5/2008 | Rawls-Meehan |
| 2008/0120779 A1 | 5/2008 | Rawls-Meehan |
| 2008/0120784 A1 | 5/2008 | Warner et al. |
| 2008/0122616 A1 | 5/2008 | Warner |
| 2008/0126122 A1 | 5/2008 | Warner et al. |
| 2008/0126132 A1 | 5/2008 | Warner |
| 2008/0127418 A1 | 6/2008 | Rawls-Meehan |
| 2008/0127424 A1 | 6/2008 | Rawls-Meehan |
| 2008/0147442 A1 | 6/2008 | Warner |
| 2008/0162171 A1 | 7/2008 | Rawls-Meehan |
| 2008/0189865 A1 | 8/2008 | Bhai |
| 2008/0262657 A1 | 10/2008 | Howell et al. |
| 2008/0275314 A1 | 11/2008 | Mack et al. |
| 2008/0281611 A1 | 11/2008 | Rawls-Meehan |
| 2008/0281612 A1 | 11/2008 | Rawls-Meehan |
| 2008/0281613 A1 | 11/2008 | Rawls-Meehan |
| 2008/0288272 A1 | 11/2008 | Rawls-Meehan |
| 2008/0288273 A1 | 11/2008 | Rawls-Meehan |
| 2008/0306351 A1 | 12/2008 | Izumi |
| 2008/0307582 A1 | 12/2008 | Flocard et al. |
| 2009/0018853 A1 | 1/2009 | Rawls-Meehan |
| 2009/0018854 A1 | 1/2009 | Rawls-Meehan |
| 2009/0018855 A1 | 1/2009 | Rawls-Meehan |
| 2009/0018856 A1 | 1/2009 | Rawls-Meehan |
| 2009/0018857 A1 | 1/2009 | Rawls-Meehan |
| 2009/0018858 A1 | 1/2009 | Rawls-Meehan |
| 2009/0024406 A1 | 1/2009 | Rawls-Meehan |
| 2009/0037205 A1 | 2/2009 | Rawls-Meehan |
| 2009/0043595 A1 | 2/2009 | Rawls-Meehan |
| 2009/0064420 A1 | 3/2009 | Rawls-Meehan |
| 2009/0100599 A1 | 4/2009 | Rawls-Meehan |
| 2009/0121660 A1 | 5/2009 | Rawls-Meehan |
| 2009/0139029 A1 | 6/2009 | Rawls-Meehan |
| 2009/0203972 A1 | 8/2009 | Henehgan et al. |
| 2009/0275808 A1 | 11/2009 | DiMaio et al. |
| 2009/0314354 A1 | 12/2009 | Chaffee |
| 2010/0025900 A1 | 2/2010 | Rawls-Meehan |
| 2010/0090383 A1 | 4/2010 | Rawls-Meehan |
| 2010/0094139 A1 | 4/2010 | Brauers et al. |
| 2010/0099954 A1 | 4/2010 | Dickinson et al. |
| 2010/0152546 A1 | 6/2010 | Behan et al. |
| 2010/0170043 A1 | 7/2010 | Young et al. |
| 2010/0170044 A1 | 7/2010 | Kao et al. |
| 2010/0174198 A1 | 7/2010 | Young et al. |
| 2010/0174199 A1 | 7/2010 | Young et al. |
| 2010/0191136 A1 | 7/2010 | Wolford |
| 2010/0199432 A1 | 8/2010 | Rawls-Meehan |
| 2010/0231421 A1 | 9/2010 | Rawls-Meehan |
| 2010/0302044 A1 | 12/2010 | Chacon et al. |
| 2010/0317930 A1 | 12/2010 | Oexman et al. |
| 2011/0001622 A1 | 1/2011 | Gentry |
| 2011/0010014 A1 | 1/2011 | Oexman et al. |
| 2011/0015495 A1 | 1/2011 | Dothie et al. |
| 2011/0041592 A1 | 2/2011 | Schmoeller et al. |
| 2011/0068935 A1 | 3/2011 | Riley et al. |
| 2011/0087113 A1 | 4/2011 | Mack et al. |
| 2011/0094041 A1 | 4/2011 | Rawls-Meehan |
| 2011/0115635 A1 | 5/2011 | Petrovski et al. |
| 2011/0138539 A1 | 6/2011 | Mahoney et al. |
| 2011/0144455 A1 | 6/2011 | Young et al. |
| 2011/0156915 A1 | 6/2011 | Brauers et al. |
| 2011/0163885 A1 | 7/2011 | Poulos et al. |
| 2011/0224510 A1 | 9/2011 | Oakhill |
| 2011/0239374 A1 | 10/2011 | Rawls-Meehan |
| 2011/0252569 A1 | 10/2011 | Rawls-Meehan |
| 2011/0258784 A1 | 10/2011 | Rawls-Meehan |
| 2011/0282216 A1 | 11/2011 | Shinar et al. |
| 2011/0283462 A1 | 11/2011 | Rawls-Meehan |
| 2011/0291795 A1 | 12/2011 | Rawls-Meehan |
| 2011/0291842 A1 | 12/2011 | Oexman |
| 2011/0295083 A1 | 12/2011 | Doelling et al. |
| 2011/0302720 A1 | 12/2011 | Yakam et al. |
| 2011/0306844 A1 | 12/2011 | Young |
| 2012/0017371 A1 | 1/2012 | Pollard |
| 2012/0025992 A1 | 2/2012 | Tallent et al. |
| 2012/0053423 A1 | 3/2012 | Kenalty et al. |
| 2012/0053424 A1 | 3/2012 | Kenalty et al. |
| 2012/0056729 A1 | 3/2012 | Rawls-Meehan |
| 2012/0057685 A1 | 3/2012 | Rawls-Meehan |
| 2012/0090698 A1 | 4/2012 | Giori et al. |
| 2012/0110738 A1 | 5/2012 | Rawls-Meehan |
| 2012/0110739 A1 | 5/2012 | Rawls-Meehan |
| 2012/0110740 A1 | 5/2012 | Rawls-Meehan |
| 2012/0112890 A1 | 5/2012 | Rawls-Meehan |
| 2012/0112891 A1 | 5/2012 | Rawls-Meehan |
| 2012/0112892 A1 | 5/2012 | Rawls-Meehan |
| 2012/0116591 A1 | 5/2012 | Rawls-Meehan |
| 2012/0119886 A1 | 5/2012 | Rawls-Meehan |
| 2012/0119887 A1 | 5/2012 | Rawls-Meehan |
| 2012/0138067 A1 | 6/2012 | Rawls-Meehan |
| 2012/0154155 A1 | 6/2012 | Brasch |
| 2012/0186019 A1 | 7/2012 | Rawls-Meehan |
| 2012/0198632 A1 | 8/2012 | Rawls-Meehan |
| 2012/0204887 A1 | 8/2012 | Connor |
| 2012/0240340 A1 | 9/2012 | Driscoll et al. |
| 2012/0304391 A1 | 12/2012 | Driscoll et al. |
| 2012/0311790 A1 | 12/2012 | Nomura et al. |
| 2013/0160212 A1 | 6/2013 | Oexman et al. |
| 2013/0174347 A1 | 7/2013 | Oexman et al. |
| 2013/0227787 A1 | 9/2013 | Herbst et al. |
| 2014/0007656 A1 | 1/2014 | Mahoney |
| 2014/0047644 A1 | 2/2014 | Mossbeck |
| 2014/0137332 A1 | 5/2014 | McGuire et al. |
| 2014/0182061 A1 | 7/2014 | Zaiss |
| 2014/0250597 A1 | 9/2014 | Chen et al. |
| 2014/0257571 A1 | 9/2014 | Chen et al. |
| 2014/0259417 A1 | 9/2014 | Nunn et al. |
| 2014/0259418 A1 | 9/2014 | Nunn et al. |
| 2014/0259419 A1 | 9/2014 | Stusynski |
| 2014/0259431 A1 | 9/2014 | Fleury |
| 2014/0259433 A1 | 9/2014 | Nunn et al. |
| 2014/0259434 A1 | 9/2014 | Nunn et al. |
| 2014/0277611 A1 | 9/2014 | Nunn et al. |
| 2014/0277778 A1 | 9/2014 | Nunn et al. |
| 2014/0277822 A1 | 9/2014 | Nunn et al. |
| 2014/0313700 A1 | 10/2014 | Connell et al. |
| 2015/0007393 A1 | 1/2015 | Palashewski et al. |
| 2015/0025327 A1 | 1/2015 | Young et al. |
| 2015/0026896 A1 | 1/2015 | Fleury et al. |
| 2015/0136146 A1 | 5/2015 | Hood et al. |
| 2015/0157137 A1 | 6/2015 | Nunn et al. |
| 2015/0157519 A1 | 6/2015 | Stusynski et al. |
| 2015/0173671 A1 | 6/2015 | Paalasmaa et al. |
| 2015/0182033 A1 | 7/2015 | Brosnan et al. |
| 2015/0182397 A1 | 7/2015 | Palashewski et al. |
| 2015/0182399 A1 | 7/2015 | Palashewski et al. |
| 2015/0182418 A1 | 7/2015 | Zaiss |
| 2015/0290059 A1 | 10/2015 | Brosnan et al. |
| 2015/0374137 A1 | 12/2015 | Mahoney et al. |
| 2016/0015184 A1 | 1/2016 | Nunn et al. |
| 2016/0015314 A1 | 1/2016 | Dusanter et al. |
| 2016/0100696 A1 | 4/2016 | Palashewski et al. |
| 2016/0338871 A1 | 11/2016 | Nunn et al. |
| 2016/0367039 A1 | 12/2016 | Young et al. |
| 2017/0065220 A1 | 3/2017 | Young et al. |
| 2017/0128001 A1 | 5/2017 | Torre et al. |
| 2017/0135632 A1 | 5/2017 | Franceschetti et al. |
| 2017/0143269 A1 | 5/2017 | Young et al. |

(56) References Cited

U.S. PATENT DOCUMENTS

| | | | |
|---|---|---|---|
| 2019/0053761 A1 | 2/2019 | Torre et al. | |
| 2019/0069840 A1 | 3/2019 | Young et al. | |
| 2019/0200777 A1* | 7/2019 | Demirli | A61B 5/7267 |
| 2019/0201265 A1 | 7/2019 | Sayadi et al. | |
| 2019/0201266 A1 | 7/2019 | Sayadi et al. | |
| 2019/0201267 A1 | 7/2019 | Demirli et al. | |
| 2019/0201268 A1 | 7/2019 | Sayadi et al. | |
| 2019/0201270 A1 | 7/2019 | Sayadi et al. | |
| 2019/0201271 A1 | 7/2019 | Grey et al. | |
| 2019/0328146 A1 | 10/2019 | Palashewski et al. | |
| 2019/0328147 A1 | 10/2019 | Palashewski et al. | |
| 2019/0357696 A1 | 11/2019 | Palashewski et al. | |
| 2020/0315367 A1 | 10/2020 | Demirli et al. | |
| 2020/0336010 A1 | 10/2020 | Holmvik et al. | |
| 2020/0337470 A1 | 10/2020 | Sayadi et al. | |
| 2020/0359807 A1 | 11/2020 | Brosnan et al. | |
| 2020/0367663 A1 | 11/2020 | Nunn et al. | |
| 2020/0383633 A1 | 12/2020 | Su et al. | |
| 2020/0383854 A1 | 12/2020 | Gehrke et al. | |
| 2020/0405070 A1 | 12/2020 | Palashewski et al. | |
| 2020/0405240 A1 | 12/2020 | Palashewski et al. | |
| 2021/0000261 A1 | 1/2021 | Erko et al. | |
| 2021/0034989 A1 | 2/2021 | Palashewski et al. | |
| 2021/0045541 A1 | 2/2021 | Nunn et al. | |
| 2021/0068552 A1 | 3/2021 | Palashewski et al. | |
| 2021/0112992 A1 | 4/2021 | Nunn et al. | |
| 2021/0267380 A1 | 9/2021 | Stusynski | |
| 2021/0282570 A1 | 9/2021 | Karschnik et al. | |
| 2021/0289947 A1 | 9/2021 | Karschnik et al. | |
| 2021/0314405 A1 | 10/2021 | Demirli et al. | |
| 2021/0346218 A1 | 11/2021 | Stusynski et al. | |
| 2021/0368998 A1 | 12/2021 | Saghiri | |
| 2022/0000273 A1 | 1/2022 | Palashewski et al. | |
| 2022/0000654 A1 | 1/2022 | Nunn et al. | |
| 2022/0225786 A1 | 7/2022 | Palashewski et al. | |
| 2022/0265059 A1 | 8/2022 | Palashewski et al. | |
| 2022/0280064 A1 | 9/2022 | Nakata et al. | |
| 2022/0305231 A1 | 9/2022 | Stusynski et al. | |
| 2022/0346565 A1 | 11/2022 | Karschnik et al. | |
| 2022/0354431 A1 | 11/2022 | Molina et al. | |
| 2022/0386947 A1 | 12/2022 | Molina et al. | |
| 2022/0395233 A1 | 12/2022 | Siyahjani et al. | |
| 2023/0018558 A1 | 1/2023 | Demirli et al. | |
| 2023/0035257 A1 | 2/2023 | Karschnik et al. | |
| 2023/0037482 A1 | 2/2023 | Demirli et al. | |
| 2023/0054736 A1 | 2/2023 | Holmvik et al. | |
| 2023/0063373 A1 | 3/2023 | Young et al. | |
| 2023/0142604 A1 | 5/2023 | Dixon et al. | |
| 2023/0148762 A1 | 5/2023 | Karschnik et al. | |
| 2023/0181104 A1* | 6/2023 | Johnston | A47C 31/008 128/845 |
| 2023/0190199 A1 | 6/2023 | Molina | |
| 2023/0210256 A1 | 7/2023 | MacLachlan et al. | |
| 2023/0210268 A1 | 7/2023 | Kirk et al. | |
| 2023/0210269 A1 | 7/2023 | Hill et al. | |
| 2023/0210274 A1 | 7/2023 | Hill et al. | |
| 2023/0210275 A1 | 7/2023 | Hill et al. | |
| 2023/0218093 A1 | 7/2023 | Nunn et al. | |
| 2023/0255843 A1 | 8/2023 | Sayadi et al. | |
| 2023/0363963 A1 | 11/2023 | Sayadi et al. | |
| 2023/0380756 A1 | 11/2023 | Palashewski et al. | |
| 2023/0404282 A1 | 12/2023 | Sayadi et al. | |
| 2023/0404825 A1 | 12/2023 | Stusynski et al. | |
| 2023/0412683 A1 | 12/2023 | Demirli et al. | |
| 2024/0016302 A1 | 1/2024 | Brosnan et al. | |
| 2024/0032705 A1 | 2/2024 | Nunn et al. | |
| 2024/0041221 A1 | 2/2024 | Blomseth et al. | |
| 2024/0041677 A1 | 2/2024 | Grey et al. | |
| 2024/0091487 A1 | 3/2024 | Molina et al. | |
| 2024/0138579 A1 | 5/2024 | Karschnik et al. | |
| 2024/0156279 A1 | 5/2024 | Nunn et al. | |
| 2024/0164533 A1 | 5/2024 | Johnston et al. | |
| 2024/0172878 A1 | 5/2024 | Palashewski et al. | |
| 2024/0215735 A1 | 7/2024 | Palashewski et al. | |

FOREIGN PATENT DOCUMENTS

| | | |
|---|---|---|
| CN | 102458317 | 5/2012 |
| CN | 106691382 | 12/2020 |
| DE | 4005822 | 8/1991 |
| EP | 2263620 | 12/2010 |
| GB | 2471401 | 12/2010 |
| JP | 2004-049388 | 2/2004 |
| JP | 2004-229875 | 8/2004 |
| JP | 2007-283106 | 11/2007 |
| SE | 531524 | 5/2009 |
| WO | WO 2004/082549 | 9/2004 |
| WO | WO 2008/128250 | 10/2008 |
| WO | WO 2009/108228 | 9/2009 |
| WO | WO 2009/123641 | 10/2009 |
| WO | WO 2010/149788 | 12/2010 |
| WO | WO 2016/107121 | 7/2016 |

OTHER PUBLICATIONS

U.S. Appl. No. 17/745,508, Nunn et al., May 16, 2022.
U.S. Appl. No. 18/433,289, Demirli et al., Feb. 5, 2024.
U.S. Appl. No. 18/602,407, Holmvik et al., Mar. 12, 2024.
U.S. Appl. No. 18/604,949, Palashewski et al., Mar. 14, 2024.
U.S. Appl. No. 18/639,292, Mayandi et al., Apr. 18, 2024.
U.S. Appl. No. 18/643,648, Mayandi et al., Apr. 23, 2024.
U.S. Appl. No. 18/680,960, Garcia Molina et al., May 31, 2024.
U.S. Appl. No. 18/749,089, Garcia Molina, Jun. 20, 2024.
U.S. Appl. No. 18/768,651, Palashewski et al., Jul. 10, 2024.
U.S. Appl. No. 18/771,026, Stusynski, Jul. 3, 2024.
U.S. Appl. No. 18/784,273, Nunn et al., Jul. 25, 2024.
U.S. Appl. No. 29/881,955, Stusynski et al., Jan. 9, 2023.
U.S. Appl. No. 29/910,800, Stusynski et al., Aug. 24, 2023.
U.S. Appl. No. 29/924,373, Dixon et al., Jan. 18, 2024.
International Search Report and Written Opinion in International Appln. No. PCT/US2024/025179, mailed on Sep. 26, 2024, 22 pages.
Invitation to Pay Additional Fees and, Where Applicable, Protest Fee in International Appln. No. PCT/US2024/025179, mailed on Aug. 5, 2024, 14 pages.

* cited by examiner

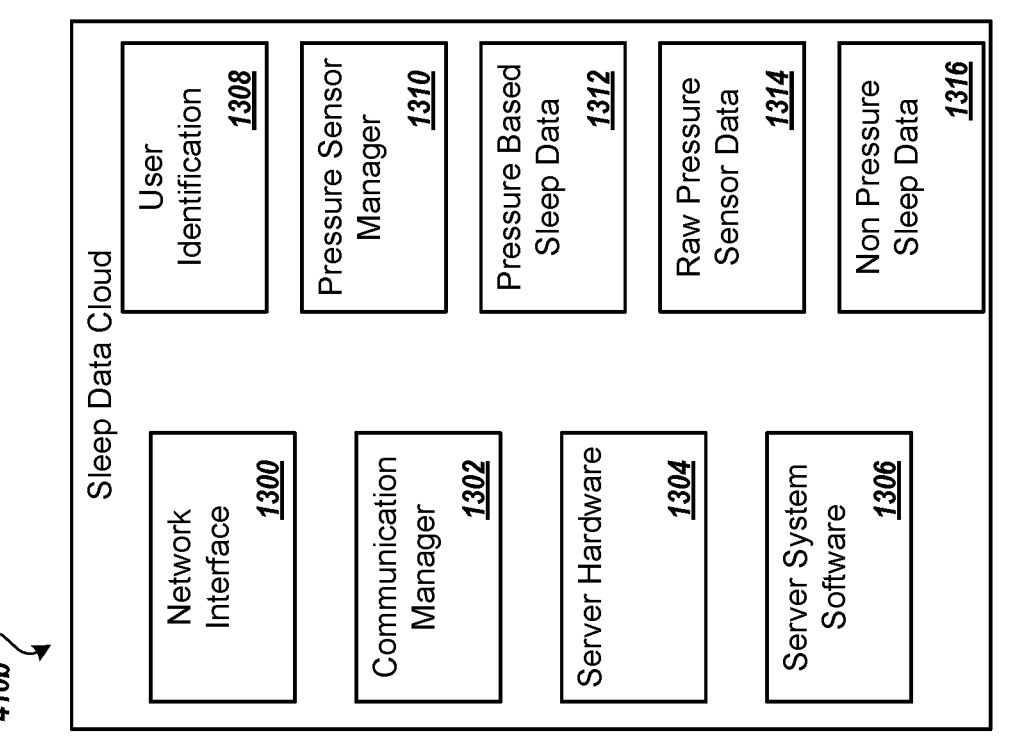

410b

Sleep Data Cloud

| Network Interface 1300 | User Identification 1308 |
| Communication Manager 1302 | Pressure Sensor Manager 1310 |
| Server Hardware 1304 | Pressure Based Sleep Data 1312 |
| Server System Software 1306 | Raw Pressure Sensor Data 1314 |
| | Non Pressure Sleep Data 1316 |

Bed Data Cloud

| Network Interface 1200 | User Identification 1208 |
| Communication Manager 1202 | Device Management 1210 |
| Server Hardware 1204 | Sensor Data 1212 |
| Server System Software 1206 | Advanced Sleep Data 1214 |

FIG. 12

Right side correlation < Left side correlation: Left side snore
Right side correlation > Left side correlation: Right side snore

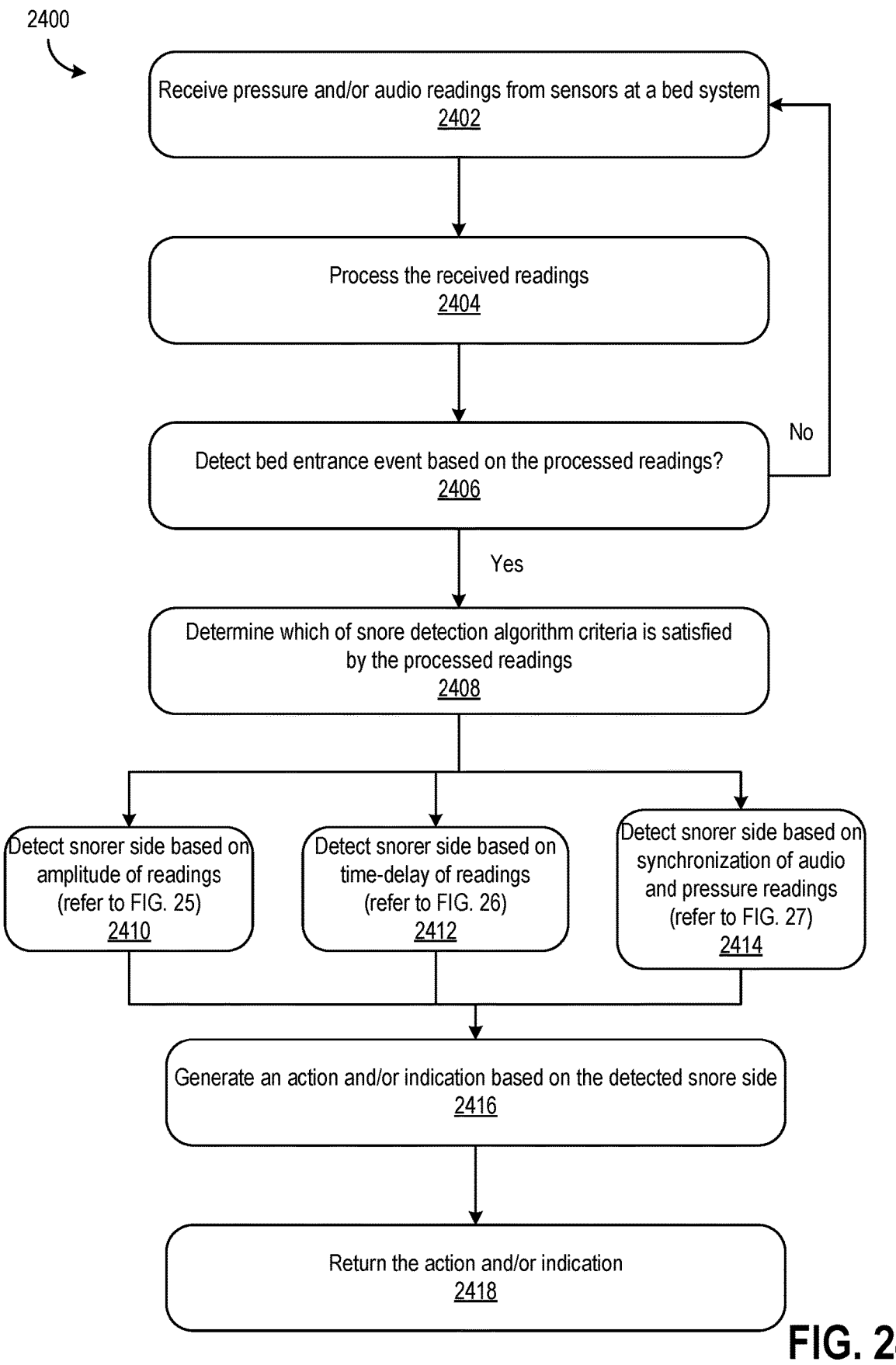

2400

Receive pressure and/or audio readings from sensors at a bed system
2402

Process the received readings
2404

Detect bed entrance event based on the processed readings?
2406

No

Yes

Determine which of snore detection algorithm criteria is satisfied by the processed readings
2408

Detect snorer side based on amplitude of readings (refer to FIG. 25)
2410

Detect snorer side based on time-delay of readings (refer to FIG. 26)
2412

Detect snorer side based on synchronization of audio and pressure readings (refer to FIG. 27)
2414

Generate an action and/or indication based on the detected snore side
2416

Return the action and/or indication
2418

```
┌─────────────────────────────────────────────────────────┐
│  Determine a first amplitude of first acoustic readings    │
│      indicative of sensed acoustics of a first sleeper     │
│                          2502                              │
└─────────────────────────────────────────────────────────┘
                            │
                            ▼
┌─────────────────────────────────────────────────────────┐
│  Determine a second amplitude of second acoustic readings  │
│    indicative of sensed acoustics of a second sleeper      │
│                          2504                              │
└─────────────────────────────────────────────────────────┘
                            │
                            ▼
┌─────────────────────────────────────────────────────────┐
│  Identify a higher amplitude amongst the first and second  │
│                       amplitudes                           │
│                          2506                              │
│  ┌─────────────────────────────────────────────────────┐  │
│  │      Compare the first and second amplitudes to a     │  │
│  │             threshold amplitude level                 │  │
│  │                      2508                             │  │
│  └─────────────────────────────────────────────────────┘  │
│  ┌─────────────────────────────────────────────────────┐  │
│  │  Identify the higher amplitude as the amplitude that   │  │
│  │        exceeds the threshold amplitude level          │  │
│  │                      2510                             │  │
│  └─────────────────────────────────────────────────────┘  │
│  ┌─────────────────────────────────────────────────────┐  │
│  │  Provide as input to a model the first and second      │  │
│  │              acoustic readings                        │  │
│  │                      2512                             │  │
│  └─────────────────────────────────────────────────────┘  │
│  ┌─────────────────────────────────────────────────────┐  │
│  │  Receive as output from the model an indication of a   │  │
│  │    bed side that corresponds to the higher amplitude   │  │
│  │                      2514                             │  │
│  └─────────────────────────────────────────────────────┘  │
└─────────────────────────────────────────────────────────┘
                            │
                            ▼
┌─────────────────────────────────────────────────────────┐
│  Return an indication of a bed side that corresponds to    │
│                 the higher amplitude                       │
│                          2516                              │
└─────────────────────────────────────────────────────────┘
```

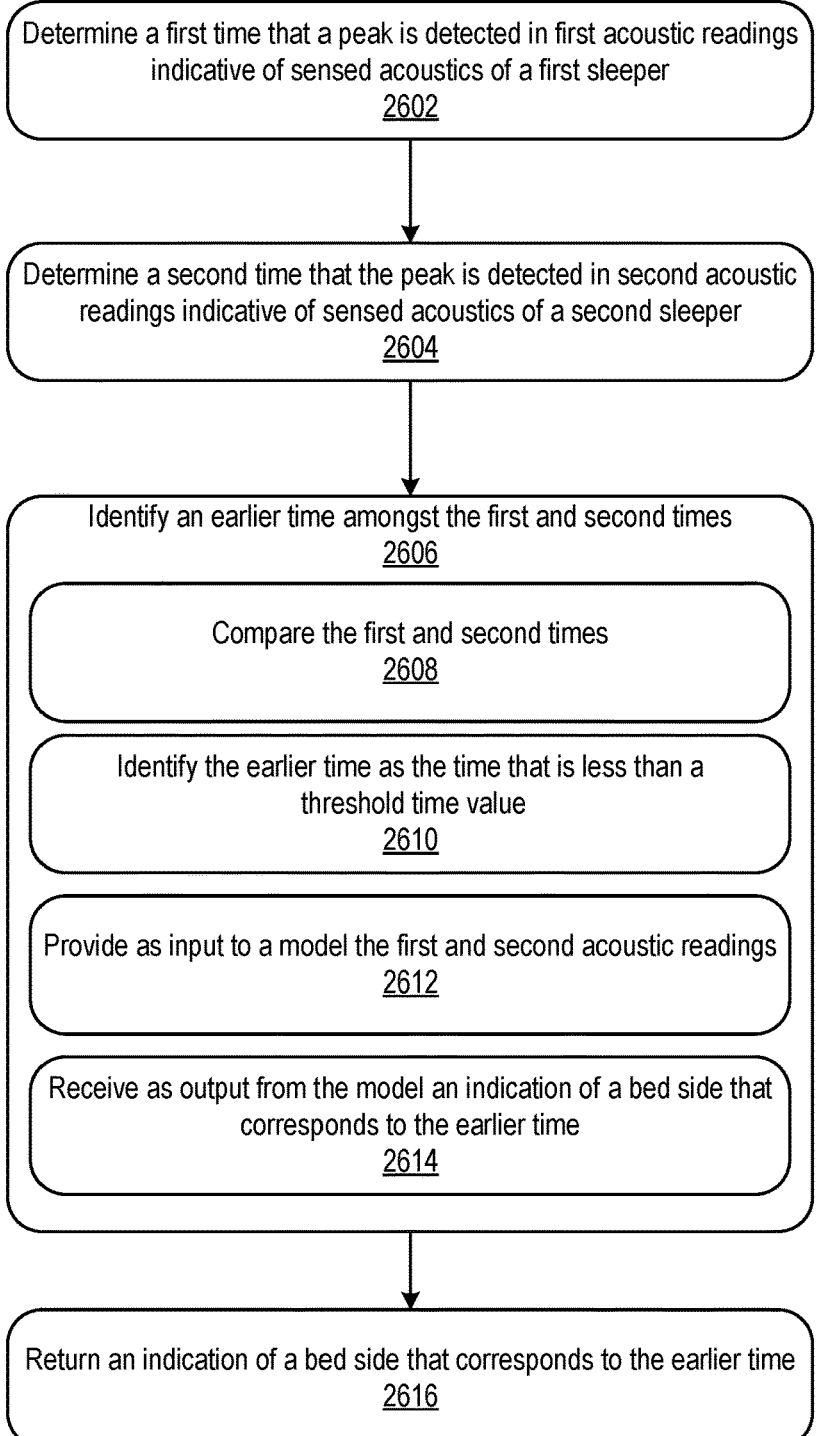

Determine a first time that a peak is detected in first acoustic readings indicative of sensed acoustics of a first sleeper
2602

Determine a second time that the peak is detected in second acoustic readings indicative of sensed acoustics of a second sleeper
2604

Identify an earlier time amongst the first and second times
2606

Compare the first and second times
2608

Identify the earlier time as the time that is less than a threshold time value
2610

Provide as input to a model the first and second acoustic readings
2612

Receive as output from the model an indication of a bed side that corresponds to the earlier time
2614

Return an indication of a bed side that corresponds to the earlier time
2616

BED SYSTEM FOR DETECTING SNORE SIDE

CROSS-REFERENCE TO RELATED APPLICATIONS

This application claims the benefit of U.S. Provisional Application Ser. No. 63/460,697, filed Apr. 20, 2023. The disclosure of the prior application is considered part of the disclosure of this application, and is incorporated in its entirety into this application.

The present document relates to bed systems for detecting a side of a bed where a sleeper is snoring based on computer-automated assessment of sensor readings, such as acoustic sensor readings and/or pressure sensor readings.

BACKGROUND

In general, a bed is a piece of furniture used as a location to sleep or relax. Many modern beds include a soft mattress on a bed frame. The mattress may include springs, foam material, and/or an air chamber to support the weight of one or more occupants.

SUMMARY

This document generally describes bed systems for automatically determining which side of a bed a detected snore originates from, where two sleepers are in the bed. A bed system can include sensors on first and second (e.g., left and right) sides of the bed system. The sensors can include acoustic sensors (e.g., audio sensors) and/or pressure sensors (e.g., inside air chambers of a mattress of the bed). The sensors can collect sensor readings, such as acoustic readings and pressure readings, on respective sides of the bed. The collected sensor readings can be processed by a computer system, such as a controller of the bed system or a remote computing system, to determine whether a snore is detected at the bed system and which side of the bed system the snore originates from. Based on the determination of the snorer side of the bed system, the computer system can also generate one or more actions, which can be used to mitigate, reduce, or otherwise stop the snoring on the determined snorer side of the bed system (e.g., moving or adjusting all or a portion of the sleeping surface for the identified side of the bed supporting the snoring person, such as by tilting the snorer side of the bed system by a predetermined amount or angle, raising a head portion of the snorer side, etc.).

The computer system can determine the snorer side of the bed system using one or more techniques described herein. For example, the computer system can determine the snorer side based on a comparison of amplitudes between acoustic readings from first and second side acoustic sensors and identification of the side of the bed system having the highest amplitude of acoustic readings. As another example, the computer system can determine the snorer side based on a comparison of time-delays between acoustic readings from the first and second side acoustic sensors and identification of the side of the bed system having the smallest time delay of acoustic readings. As yet another example, the computer system can determine the snorer side based on detection of synchronized behavior between the acoustic readings and the pressure readings for each of the first and second sides of the bed system and identification of the side of the bed system having the most synchronized behavior. Any of these techniques can be selected by the computer system during runtime and based on quality of the readings received from the sensors. Any of these techniques can be performed by the computer system by implementing one or more machine learning-trained models that have been trained to detect snorer side based on processing of acoustic and/or pressure readings that are received from sensors at the bed system while 2 sleepers are on the bed system.

Some embodiments described herein include a bed system including a mattress having a first side to support a first user and a second side to support a second user; a first pressure sensor proximate the first side of the mattress configured to sense pressure applied to the first side of the mattress; a second pressure sensor proximate the second side of the mattress configured to sense pressure applied to the second side of the mattress; a first acoustic sensor proximate the first side of the mattress configured to sense acoustics from the first user on the first side of the mattress; a second acoustic sensor proximate the second side of the mattress configured to sense acoustics from the second user on the second side of the mattress; and a computer system in data communication with the first pressure sensor, the second pressure sensor, the first acoustic sensor, and the second acoustic sensor. The computer system can be configured to receive, from the first pressure sensor, first pressure readings indicative of the sensed pressure at the first side of the mattress; receive, from the second pressure sensor, second pressure readings indicative of the sensed pressure at the second side of the mattress; receive, from the first acoustic sensor, first acoustic readings indicative of the sensed acoustics from the first user; receive, from the second acoustic sensor, second acoustic readings indicative of the sensed acoustics from the second user; detect, based on the first and second pressure readings, first and second breathing cycles for the first and second users, respectively; determine a first correlation coefficient for the first breathing cycle and the first acoustic readings; determine a second correlation coefficient for the second breathing cycle and the second acoustic readings; identify a higher correlation coefficient amongst the first and second correlation coefficients, wherein the higher correlation coefficient indicates that one of the first and second users is snoring; and return an indication of a side of the bed system that corresponds to the higher correlation coefficient, wherein the indication indicates the side of the bed system where the one of the first and second users is snoring.

Embodiments described herein can include one or more optional features. For example, identifying the higher correlation coefficient can include providing, as input to a machine learning-trained model, the first breathing cycle, the first acoustic readings, the second breathing cycle, and the second acoustic readings; and receiving, as output from the model, an indication of the higher correlation coefficient, wherein the model was trained to determine the first and second correlation coefficients and compare the first and second correlation coefficients to identify the higher correlation coefficient. Identifying the higher correlation coefficient can include comparing the first and second correlation coefficients to a threshold correlation coefficient value; and identifying the higher correlation coefficient as one of the first and second correlation coefficients that exceeds the threshold correlation coefficient value. Determining the first correlation coefficient further can include synchronizing the first breathing cycle with the first acoustic readings, and determining the second correlation coefficient further comprises synchronizing the second breathing cycle with the second acoustic readings. Detecting the first and second breathing cycles for the first and second users, respectively, can include applying band-pass filtering techniques to each of the first and second pressure readings.

The computer system can be configured to perform the detecting, determining, identifying, and returning steps based on: processing the received readings; and determining that each of the processed readings exceed respective threshold quality levels. In some examples, in response to determining that at least one of the processed first or second pressure readings does not exceed the respective threshold quality levels, the computer system can additionally be configured to determine a first amplitude of the first acoustic readings; determine a second amplitude of the second acoustic readings; identify a higher amplitude amongst the first and second amplitudes, wherein the higher amplitude indicates that one of the first and second users is snoring; and return the indication of the side of the bed system that corresponds to the higher amplitude, wherein the indication indicates the side of the bed system where the one of the first and second users is snoring. In some examples, in response to determining that at least one of the processed first or second pressure readings does not exceed the respective threshold quality levels, the computer system can be configured to determine a first time that a peak is detected in the first acoustic readings, wherein the peak indicates a snore; determine a second time that the peak is detected in the second acoustic readings; identify an earlier time amongst the first time and the second time, wherein the earlier time indicates that one of the first and second users is snoring; and return the indication of the side of the bed system that corresponds to the earlier time, wherein the indication indicates the side of the bed system where the one of the first and second users is snoring.

The computer system can be further configured to generate an action in response to the indication of the side of the bed system where the one of the first and second users is snoring, wherein the action comprises generating instructions that cause a controller of the bed system to (i) automatically raise a head portion of the side of the bed system where the one of the first and second users is snoring or (ii) automatically tilt a portion of a foundation of the bed system that corresponds to the side of the bed system where the one of the first and second users is snoring. In some examples, in response to generating the action, the computer system can be configured to continuously perform the receiving, detecting, determining, identifying, and returning steps. The computer system can be configured to continuously perform the steps until the computer system determines, based on processing at least one of the received readings, that at least one of the first or second users (i) exits the bed system, (ii) wakes up, or (iii) experiences at least a threshold level of movement. The computer system can be configured to perform the detecting, determining, identifying, and returning steps in response to determining, based on processing at least one of the received readings, that at least one of the first or second users (i) entered the bed system or (ii) fell asleep. The computer system can be a controller of the bed system. The computer system can be remote from the bed system.

The bed system further can further include a foundation, wherein the first acoustic sensor is integrated into a first side of the foundation and the second acoustic sensor is integrated into a second side of the foundation, the second side of the foundation being opposite the first side, wherein the first side is configured to support the first user and the second side is configured to support the second user. The first and second acoustic sensors can integrated into at least one device that is positioned near the bed system, the at least one device being at least one of a mobile phone, smartphone, wearable device, laptop, tablet, or home automation device. The computer system can be configured to perform the steps in near real-time.

The computer system can be further configured to determine that both the first and second users are snoring based on: identifying a first audio pitch in the first acoustic readings; identifying a second audio pitch in the second acoustic readings; determining whether the first and second audio pitches indicate a same snore event based on comparing the first and second audio pitches; determining that the first and second audio pitches represent first and second snore events of the first and second users, respectively, based on a determination that the first and second audio pitches do not indicate the same snore event; and returning an indication that the first and second users are snoring. The computer system can be further configured to generate at least one action in response to the indication that the first and second users are snoring, wherein the action comprises generating instructions that cause a controller of the bed system to automatically adjust at least one side of the bed system.

Some embodiments described herein include a bed system configured to support a first user on a first side of the bed system and a second user on a second side of the bed system, the bed system including: a first acoustic sensor positioned proximate the first side of the bed system configured to sense acoustics from the first user; a second acoustic sensor positioned proximate the second side of the bed system configured to sense acoustics from the second user; and a computer system in data communication with the first acoustic sensor and the second acoustic sensor. The computer system can be configured to: receive, from the first acoustic sensor, first acoustic readings indicative of the sensed acoustics from the first user; receive, from the second acoustic sensor, second acoustic readings indicative of the sensed acoustics from the second user; determine a first amplitude of the first acoustic readings; determine a second amplitude of the second acoustic readings; identify a higher amplitude amongst the first and second amplitudes, wherein the higher amplitude indicates that one of the first and second users is snoring; and return an indication of a side of the bed system that corresponds to the higher amplitude, wherein the indication indicates the side of the bed system where the one of the first and second users is snoring.

Embodiments described herein can include one or more optional features. For example, identifying the higher amplitude can include comparing each of the first and second amplitudes to a threshold amplitude level; and identifying the higher amplitude as the first or second amplitude that exceeds the threshold amplitude level. Identifying the higher amplitude can include providing, as input to a machine learning-trained model, the first and second acoustic readings; and receiving, as output from the model, the indication of the side of the bed system that corresponds to the higher amplitude, wherein the model was trained to determine the first and second amplitudes and identify the higher amplitude based on comparing the first and second amplitudes. The bed system can further include at least one pressure sensor and the computer system is configured to: receive, from the at least one pressure sensor, pressure readings indicative of sensed pressure at at least one of the first or second sides of the bed system; process the pressure readings; determine, based on the processing, that the pressure readings are less than a threshold level of quality; and perform, in response to determining that the pressure readings are less than the threshold level of quality, the determining, identifying, and returning steps.

Some embodiments described herein include a bed system configured to support a first user on a first side of the bed system and a second user on a second side of the bed system, the bed system including a first acoustic sensor positioned proximate the first side of the bed system configured to sense acoustics from the first user; a second acoustic sensor positioned proximate the second side of the bed system configured to sense acoustics from the second user; and a computer system in data communication with the first acoustic sensor and the second acoustic sensor. The computer system can be configured to: receive, from the first acoustic sensor, first acoustic readings indicative of the sensed acoustics from the first user; receive, from the second acoustic sensor, second acoustic readings indicative of the sensed acoustics from the second user; determine a first time that a peak is detected in the first acoustic readings, wherein the peak indicates a snore; determine a second time that the peak is detected in the second acoustic readings; identify an earlier time amongst the first time and the second time, wherein the earlier time indicates that one of the first and second users is snoring; and return an indication of a side of the bed system that corresponds to the earlier time, wherein the indication indicates the side of the bed system where the one of the first and second users is snoring.

Embodiments described herein can include one or more optional features. For example, identifying the earlier time can include comparing the first and second times; and identifying the earlier time as the first or second time that is less than a threshold time value. Identifying the earlier time can include providing, as input to a machine learning-trained model, the first and second acoustic readings; and receiving, as output from the model, the indication of the side of the bed system that corresponds to the earlier time, wherein the model was trained to determine the first and second times and identify the earlier time based on comparing the first and second times. The bed system can further include at least one pressure sensor and the computer system is configured to: receive, from the at least one pressure sensor, pressure readings indicative of sensed pressure at the bed system; process the pressure readings; determine, based on the processing, that the pressure readings are less than a threshold level of quality; and perform, in response to determining that the pressure readings are less than the threshold level of quality, the determining, identifying, and returning steps.

Some embodiments described herein include a bed system for supporting a first user and a second user, the bed system including at least one pressure sensor configured to sense pressure applied to the bed system by at least one of the first or second users; at least one acoustic sensor configured to sense acoustics by at least one of the first or second users; and a computer system in data communication with the at least one pressure sensor and the at least one acoustic sensor. The computer system can be configured to: receive, from the at least one pressure sensor, pressure readings indicative of the sensed pressure at the bed system; receive, from the at least one acoustic sensor, acoustic readings indicative of the sensed acoustics from at least one of the first or second users; detect a snore event by at least one of the first or second users based on processing at least one of the pressure readings or the acoustic readings; determine, based on the detected snore event, a side of the bed system; and return an indication of the side of the bed system where the snore event is detected.

Embodiments described herein can include one or more optional features. For example, processing at least one of the pressure readings or the acoustic readings can include providing, as input to a machine learning-trained model, at least one of the pressure readings or the acoustic readings; and receiving, as output from the model, the detected snore event and the determined side of the bed system. The model can be trained to: synchronize a first portion of the pressure readings with a first portion of the acoustic readings, wherein the first portion of the readings correspond to a first side of the bed system where the first user rests; determine a first correlation coefficient between the synchronized first readings; synchronize a second portion of the pressure readings with a second portion of the acoustic readings, wherein the second portion of the readings correspond to a second side of the bed system where the second user rests; determine a second correlation coefficient between the synchronized second readings; and detect the snore event based on identifying a higher correlation coefficient amongst the first and second correlation coefficients. The model can be trained to: determine a first amplitude of a first portion of the acoustic readings, wherein the first portion of the readings correspond to a first side of the bed system where the first user rests; determine a second amplitude of a second portion of the acoustic readings, wherein the second portion of the readings correspond to a second side of the bed system where the second user rests; and detect the snore event based on identifying a higher amplitude amongst the first and second amplitudes. The model can be trained to: determine a first time of a first portion of the acoustic readings at which a peak is detected, wherein the peak indicates a snore and the first portion of the readings correspond to a first side of the bed system where the first user rests; determine a second time of a second portion of the acoustic readings at which the peak is detected, wherein the second portion of the readings correspond to a second side of the bed system where the second user rests; and detect the snore event based on identifying an earlier time amongst the first and second times.

The at least one pressure sensor can include a first pressure sensor integrated into the bed system proximate the first user and a second pressure sensor integrated into the bed system proximate the second user. The first pressure sensor can be integrated into a first side of a foundation of the bed system, wherein the first side of the foundation is configured to support the first user. The second pressure sensor can be integrated into a second side of the foundation, wherein the second side of the foundation is configured to support the second user. The first pressure sensor can be integrated into a first side of a mattress of the bed system, wherein the first side of the mattress is configured to support the first user. The second pressure sensor can be integrated into a second side of the mattress, wherein the second side of the mattress is configured to support the second user. The at least one acoustic sensor can include a first acoustic sensor positioned proximate the first user and a second acoustic sensor positioned proximate the second user. The first acoustic sensor can be integrated into a first side of a foundation of the bed system, wherein the first side of the foundation is configured to support the first user. The second acoustic sensor can be integrated into a second side of the foundation, wherein the second side of the foundation is configured to support the second user.

The devices, system, and techniques described herein may provide one or more of the following advantages. For example, the disclosed techniques provide improved, accurate, and real-time or near real-time identification of which sleeper of a bed system supporting multiple sleepers is snoring. The disclosed techniques leverage existing components of a bed system (e.g., smart bed) such as acoustic sensors and pressure sensors. The disclosed techniques may also leverage processing power at the bed system, such as at a controller of the bed system, to provide faster and lightweight snorer side determinations to be made in real-time or near real-time. As a result of the faster and lightweight processing, the disclosed techniques allow for real-time or near real-time adjustments to be made to the bed system in order to alleviate the detected snoring. The faster and lightweight processing also allows for available compute resources to be used in other processing operations performed at the bed system in real-time or near real-time and while the sleepers are on the bed system (e.g., adjusting a microclimate of the bed, adjusting firmness of the bed).

The disclosed techniques can also be applied to bed systems having any variety of sensors. For example, the disclosed techniques can apply to bed systems having both pressure and acoustic sensors and also bed systems that only have acoustic sensors or only pressure sensors or tactile sensors. As a result, the disclosed techniques can easily be implemented in existing bed systems as well as new bed systems, without requiring modifications or adaptation of the techniques per bed system.

Similarly, the disclosed techniques provide for automatic determination of which method/algorithm to use in detecting snorer side in real-time or near real-time so that the snorer side can be quickly and efficiently determined while the sleepers are on the bed system. For example, pressure and acoustic readings can be processed and it can be determined that the pressure readings are too noisy and/or that the acoustic readings are unreliable. Based on such determinations, the disclosed techniques can quickly adapt and select one of the methods/algorithms described herein to accurately detect snorer side in real-time or near real-time.

The disclosed techniques also may utilize machine learning techniques to accurately and quickly determine the snorer side at the bed system. Machine learning models can be iteratively trained and improved to improve accuracy of detecting snorer side based on the acoustic readings and/or a combination of the acoustic readings and pressure readings. As a result, such models can be reliably used to detect the snorer side regardless of a quality, consistency, fluctuation, and/or quantity of sensor readings that are received and processed by the models.

The details of one or more implementations are set forth in the accompanying drawings and the description below. Other features, aspects and potential advantages will be apparent from the accompanying description and figures.

DESCRIPTION OF DRAWINGS

FIGS. 12-16 are block diagrams of example cloud services that can be used in a data processing system associated with a bed.

FIG. 24 is a flowchart of a process for detecting snorer side at a bed system described herein.

FIG. 25 is a flowchart of a process for detecting snorer side at a bed system based on assessing amplitude of acoustic readings.

FIG. 26 is a flowchart of a process for detecting snorer side at a bed system based on assessing time-delay of acoustic readings.

DETAILED DESCRIPTION

This document generally describes bed systems for automatically determining snorer side at a bed system. Some bed systems are designed for two sleepers. Such a bed system can include a mattress to support a left-side sleeper on a left-side portion of the mattress (e.g., a first side) and a right-side sleeper on a right-side portion of the mattress (e.g., a second side). The bed system can include at least one acoustic sensor (e.g., audio sensor, microphone) configured to sense acoustic energy in an environment of the left-side sleeper and/or the right-side sleeper. Sometimes, each side of the bed system can include at least one acoustic sensor. The bed system may also include at least one pressure sensor configured to sense pressure applied to the left-side portion of the mattress by the left-side sleepers and/or the right-side portion of the mattress by the right-side user. Sometimes, each side of the bed system can include at least one pressure sensor. The bed system can, in some implementations, include other types of sensors in addition to or in place of acoustic and pressure sensors. For example, the bed system can include one or more tactile, visual, infrared, or temperature sensors for use in determining a side of the bed that supports a snoring person. Acoustic, pressure, and/or other readings that are detected/collected by the described sensors can be transmitted to a computer system, such as a controller of the bed system and/or a remote computer system, and processed by the computer system to determine a snorer side at the bed system. The computer system can automatically identify and apply one or more techniques to determine the snorer side based on processing and assessing quality of the received sensor readings. For example, the computer system can apply techniques that detect the snorer side based on assessment of acoustic readings amplitudes, assessment of acoustic readings time-delays, and/or assessment of synchronized behavior between acoustic and pressure readings. Based on the determination of the snorer side, the computer system can also generate and/or implement one or more actions at the bed system in real-time or near real-time to mitigate the detected snoring.

Example Airbed Hardware

Figure 1:
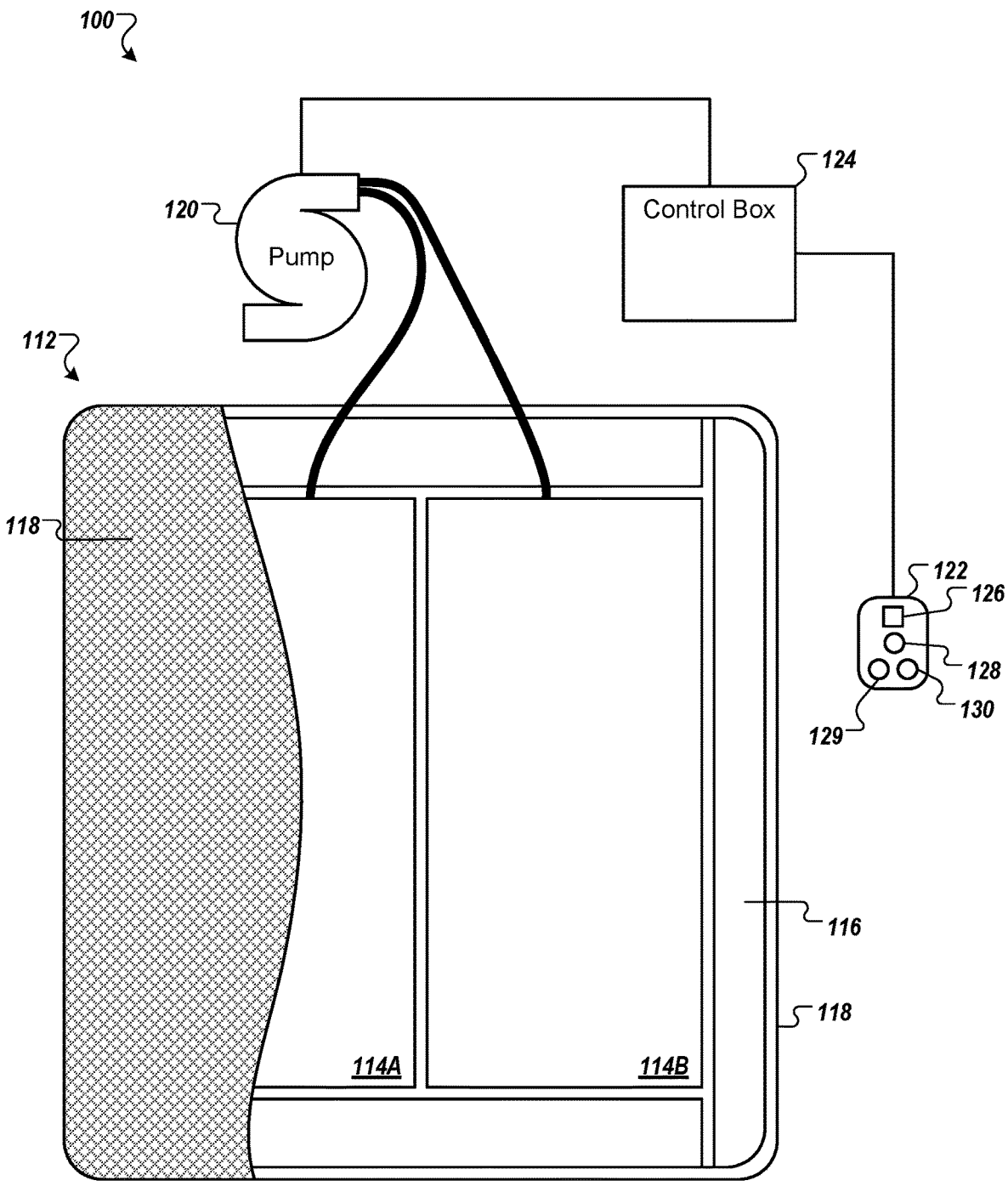
FIG. 1 shows an example air bed system.

FIG. 1 shows an example air bed system 100 that includes a bed 112. The bed 112 can be a mattress that includes at least one air chamber 114 surrounded by a resilient border 116 and encapsulated by bed ticking 118. The resilient border 116 can comprise any suitable material, such as foam. In some embodiments, the resilient border 116 can combine with a top layer or layers of foam (not shown in FIG. 1) to form an upside down foam tub. In other embodiments, mattress structure can be varied as suitable for the application.

As illustrated in FIG. 1, the bed 112 can be a two chamber design having first and second fluid chambers, such as a first air chamber 114A and a second air chamber 114B. Sometimes, the bed 112 can include chambers for use with fluids other than air that are suitable for the application. For example, the fluids can include liquid. In some embodiments, such as single beds or kids' beds, the bed 112 can include a single air chamber 114A or 114B or multiple air chambers 114A and 114B. Although not depicted, sometimes, the bed 112 can include additional air chambers.

The first and second air chambers 114A and 114B can be in fluid communication with a pump 120. The pump 120 can be in electrical communication with a remote control 122 via control box 124. The control box 124 can include a wired or wireless communications interface for communicating with one or more devices, including the remote control 122. The control box 124 can be configured to operate the pump 120 to cause increases and decreases in the fluid pressure of the first and second air chambers 114A and 114B based upon commands input by a user using the remote control 122. In some implementations, the control box 124 is integrated into a housing of the pump 120. Moreover, sometimes, the pump 120 can be in wireless communication (e.g., via a home network, WIFI, BLUETOOTH, or other wireless network) with a mobile device via the control box 124. The mobile device can include but is not limited to the user's smartphone, cell phone, laptop, tablet, computer, wearable device, home automation device, or other computing device. A mobile application can be presented at the mobile device and provide functionality for the user to control the bed 112 and view information about the bed 112. The user can input commands in the mobile application presented at the mobile device. The inputted commands can be transmitted to the control box 124, which can operate the pump 120 based upon the commands.

The remote control 122 can include a display 126, an output selecting mechanism 128, a pressure increase button 129, and a pressure decrease button 130. The remote control 122 can include one or more additional output selecting mechanisms and/or buttons. The display 126 can present information to the user about settings of the bed 112. For example, the display 126 can present pressure settings of both the first and second air chambers 114A and 114B or one of the first and second air chambers 114A and 114B. Sometimes, the display 126 can be a touch screen, and can receive input from the user indicating one or more commands to control pressure in the first and second air chambers 114A and 114B and/or other settings of the bed 112.

The output selecting mechanism 128 can allow the user to switch air flow generated by the pump 120 between the first and second air chambers 114A and 114B, thus enabling control of multiple air chambers with a single remote control 122 and a single pump 120. For example, the output selecting mechanism 128 can by a physical control (e.g., switch or button) or an input control presented on the display 126. Alternatively, separate remote control units can be provided for each air chamber 114A and 114B and can each include the ability to control multiple air chambers. Pressure increase and decrease buttons 129 and 130 can allow the user to increase or decrease the pressure, respectively, in the air chamber selected with the output selecting mechanism 128. Adjusting the pressure within the selected air chamber can cause a corresponding adjustment to the firmness of the respective air chamber. In some embodiments, the remote control 122 can be omitted or modified as appropriate for an application.

Figure 2:
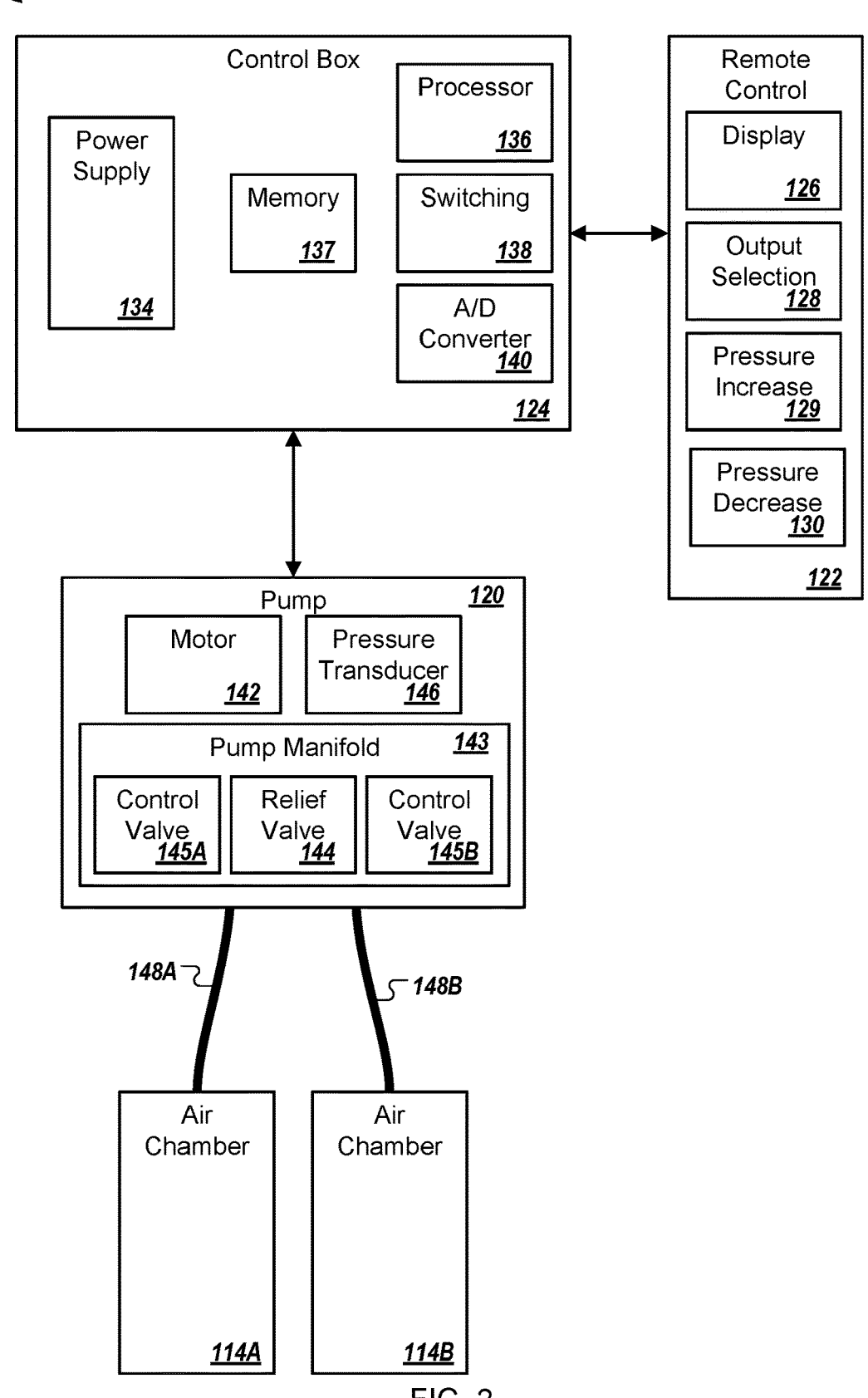
FIG. 2 is a block diagram of an example of various components of an air bed system.

FIG. 2 is a block diagram of an example of various components of an air bed system. These components can be used in the example air bed system 100. The control box 124 can include a power supply 134, a processor 136, a memory 137, a switching mechanism 138, and an analog to digital (A/D) converter 140. The switching mechanism 138 can be, for example, a relay or a solid state switch. In some implementations, the switching mechanism 138 can be located in the pump 120 rather than the control box 124. The pump 120 and the remote control 122 can be in two-way communication with the control box 124. The pump 120 includes a motor 142, a pump manifold 143, a relief valve 144, a first control valve 145A, a second control valve 145B, and a pressure transducer 146. The pump 120 is fluidly connected with the first air chamber 114A and the second air chamber 114B via a first tube 148A and a second tube 148B, respectively. The first and second control valves 145A and 145B can be controlled by switching mechanism 138, and are operable to regulate the flow of fluid between the pump 120 and first and second air chambers 114A and 114B, respectively.

In some implementations, the pump 120 and the control box 124 can be provided and packaged as a single unit. In some implementations, the pump 120 and the control box 124 can be provided as physically separate units. The control box 124, the pump 120, or both can be integrated within or otherwise contained within a bed frame, foundation, or bed support structure that supports the bed 112. Sometimes, the control box 124, the pump 120, or both can be located outside of a bed frame, foundation, or bed support structure (as shown in the example in FIG. 1).

The air bed system 100 in FIG. 2 includes the two air chambers 114A and 114B and the single pump 120 of the bed 112 depicted in FIG. 1. However, other implementations can include an air bed system having two or more air chambers and one or more pumps incorporated into the air bed system to control the air chambers. For example, a separate pump can be associated with each air chamber. As another example, a pump can be associated with multiple chambers. A first pump can be associated with air chambers that extend longitudinally from a left side to a midpoint of the air bed system 100 and a second pump can be associated with air chambers that extend longitudinally from a right side to the midpoint of the air bed system 100. Separate pumps can allow each air chamber to be inflated or deflated independently and/or simultaneously. Additional pressure transducers can also be incorporated into the air bed system 100 such that a separate pressure transducer can be associated with each air chamber.

As an illustrative example, in use, the processor 136 can send a decrease pressure command to one of air chambers 114A or 114B, and the switching mechanism 138 can convert the low voltage command signals sent by the processor 136 to higher operating voltages sufficient to operate the relief valve 144 of the pump 120 and open the respective control valve 145A or 145B. Opening the relief valve 144 can allow air to escape from the air chamber 114A or 114B through the respective air tube 148A or 148B. During deflation, the pressure transducer 146 can send pressure readings to the processor 136 via the A/D converter 140. The A/D converter 140 can receive analog information from pressure transducer 146 and can convert the analog information to digital information useable by the processor 136. The processor 136 can send the digital signal to the remote control 122 to update the display 126 to convey the pressure information to the user. The processor 136 can also send the digital signal to other devices in wired or wireless communication with the air bed system, including but not limited to mobile devices described herein. The user can then view pressure information associated with the air bed system at their device instead of at, or in addition to, the remote control 122.

As another example, the processor 136 can send an increase pressure command. The pump motor 142 can be energized in response to the increase pressure command and send air to the designated one of the air chambers 114A or 114B through the air tube 148A or 148B via electronically operating the corresponding valve 145A or 145B. While air is being delivered to the designated air chamber 114A or 114B to increase the chamber firmness, the pressure transducer 146 can sense pressure within the pump manifold 143. The pressure transducer 146 can send pressure readings to the processor 136 via the A/D converter 140. The processor 136 can use the information received from the A/D converter 140 to determine the difference between the actual pressure in air chamber 114A or 114B and the desired pressure. The processor 136 can send the digital signal to the remote control 122 to update display 126.

Generally speaking, during an inflation or deflation process, the pressure sensed within the pump manifold 143 can provide an approximation of the actual pressure within the respective air chamber that is in fluid communication with the pump manifold 143. An example method includes turning off the pump 120, allowing the pressure within the air chamber 114A or 114B and the pump manifold 143 to equalize, then sensing the pressure within the pump manifold 143 with the pressure transducer 146. Providing a sufficient amount of time to allow the pressures within the pump manifold 143 and chamber 114A or 114B to equalize can result in pressure readings that are accurate approximations of actual pressure within air chamber 114A or 114B. In some implementations, the pressure of the air chambers 114A and/or 114B can be continuously monitored using multiple pressure sensors (not shown). The pressure sensors can be positioned within the air chambers. The pressure sensors can also be fluidly connected to the air chambers, such as along the air tubes 148A and 148B.

In some implementations, information collected by the pressure transducer 146 can be analyzed to determine various states of a user laying on the bed 112. For example, the processor 136 can use information collected by the pressure transducer 146 to determine a heartrate or a respiration rate for the user. As an illustrative example, the user can be laying on a side of the bed 112 that includes the chamber 114A. The pressure transducer 146 can monitor fluctuations in pressure of the chamber 114A, and this information can be used to determine the user's heartrate and/or respiration rate. As another example, additional processing can be performed using the collected data to determine a sleep state of the user (e.g., awake, light sleep, deep sleep). For example, the processor 136 can determine when the user falls asleep and, while asleep, the various sleep states (e.g., sleep stages) of the user. Based on the determined heartrate, respiration rate, and/or sleep states of the user, the processor 136 can determine information about the user's sleep quality. The processor 136 can, for example, determine how well the user slept during a particular sleep cycle. The processor 136 can also determine user sleep cycle trends. Accordingly, the processor 136 can generate recommendations to improve the user's sleep quality and overall sleep cycle. Information that is determined about the user's sleep cycle (e.g., heartrate, respiration rate, sleep states, sleep quality, recommendations to improve sleep quality, etc.) can be transmitted to the user's mobile device and presented in a mobile application, as described above.

Additional information associated with the user of the air bed system 100 that can be determined using information collected by the pressure transducer 146 includes user motion, presence on a surface of the bed 112, weight, heart arrhythmia, snoring, partner snore, and apnea. One or more other health conditions of the user can also be determined based on the information collected by the pressure transducer 146. Taking user presence detection for example, the pressure transducer 146 can be used to detect the user's presence on the bed 112, e.g., via a gross pressure change determination and/or via one or more of a respiration rate signal, heartrate signal, and/or other biometric signals. Detection of the user's presence can be beneficial to determine, by the processor 136, adjustment(s) to make to settings of the bed 112 (e.g., adjusting a firmness when the user is present to a user-preferred firmness setting) and/or peripheral devices (e.g., turning off lights when the user is present, activating a heating or cooling system, etc.).

For example, a simple pressure detection process can identify an increase in pressure as an indication that the user is present. As another example, the processor 136 can determine that the user is present if the detected pressure increases above a specified threshold (so as to indicate that a person or other object above a certain weight is positioned on the bed 112). As yet another example, the processor 136 can identify an increase in pressure in combination with detected slight, rhythmic fluctuations in pressure as corresponding to the user being present. The presence of rhythmic fluctuations can be identified as being caused by respiration or heart rhythm (or both) of the user. The detection of respiration or a heartbeat can distinguish between the user being present on the bed and another object (e.g., a suitcase, a pet, a pillow, etc.) being placed thereon. In some implementations, pressure fluctuations can be measured at the pump 120. For example, one or more pressure sensors can be located within one or more internal cavities of the pump 120 to detect pressure fluctuations within the pump 120. The fluctuations detected at the pump 120 can indicate pressure fluctuations in the chambers 114A and/or 114B. One or more sensors located at the pump 120 can be in fluid communication with the chambers 114A and/or 114B, and the sensors can be operative to determine pressure within the chambers 114A and/or 114B. The control box 124 can be configured to determine at least one vital sign (e.g., heartrate, respiratory rate) based on the pressure within the chamber 114A or the chamber 114B.

The control box 124 can also analyze a pressure signal detected by one or more pressure sensors to determine a heartrate, respiration rate, and/or other vital signs of the user lying or sitting on the chamber 114A and/or 114B. More specifically, when a user lies on the bed 112 and is positioned over the chamber 114A, each of the user's heart beats, breaths, and other movements (e.g., hand, arm, leg, foot, or other gross body movements) can create a force on the bed 112 that is transmitted to the chamber 114A. As a result of this force input, a wave can propagate through the chamber 114A and into the pump 120. A pressure sensor located at the pump 120 can detect the wave, and thus the pressure signal outputted by the sensor can indicate a heartrate, respiratory rate, or other information regarding the user.

With regard to sleep state, the air bed system 100 can determine the user's sleep state by using various biometric signals such as heartrate, respiration, and/or movement of the user. While the user is sleeping, the processor 136 can receive one or more of the user's biometric signals (e.g., heartrate, respiration, motion, etc.) and can determine the user's present sleep state based on the received biometric signals. In some implementations, signals indicating fluctuations in pressure in one or both of the chambers 114A and 114B can be amplified and/or filtered to allow for more precise detection of heartrate and respiratory rate.

Sometimes, the processor 136 can receive additional biometric signals of the user from one or more other sensors or sensor arrays positioned on or otherwise integrated into the air bed system 100. For example, one or more sensors can be attached or removably attached to a top surface of the air bed system 100 and configured to detect signals such as heartrate, respiration rate, and/or motion. The processor 136 can combine biometric signals received from pressure sensors located at the pump 120, the pressure transducer 146, and/or the sensors positioned throughout the air bed system 100 to generate accurate and more precise information about the user and their sleep quality.

Sometimes, the control box 124 can perform a pattern recognition algorithm or other calculation based on the amplified and filtered pressure signal(s) to determine the user's heartrate and/or respiratory rate. For example, the algorithm or calculation can be based on assumptions that a heartrate portion of the signal has a frequency in a range of 0.5-4.0 Hz and that a respiration rate portion of the signal has a frequency in a range of less than 1 Hz. Sometimes, the control box 124 can use one or more machine learning models to determine the user's health information. The models can be trained using training data that includes training pressure signals and expected heartrates and/or respiratory rates. Sometimes, the control box 124 can determine user health information by using a lookup table that corresponds to sensed pressure signals.

The control box 124 can also be configured to determine other characteristics of the user based on the received pressure signal, such as blood pressure, tossing and turning movements, rolling movements, limb movements, weight, presence or lack of presence of the user, and/or the identity of the user.

For example, the pressure transducer 146 can be used to monitor the air pressure in the chambers 114A and 114B of the bed 112. If the user on the bed 112 is not moving, the air pressure changes in the air chamber 114A or 114B can be relatively minimal, and can be attributable to respiration and/or heartbeat. When the user on the bed 112 is moving, however, the air pressure in the mattress can fluctuate by a much larger amount. The pressure signals generated by the pressure transducer 146 and received by the processor 136 can be filtered and indicated as corresponding to motion, heartbeat, or respiration. The processor 136 can attribute such fluctuations in air pressure to the user's sleep quality. Such attributions can be determined based on applying one or more machine learning models and/or algorithms to the pressure signals. For example, if the user shifts and turns a lot during a sleep cycle (for example, in comparison to historic trends of the user's sleep cycles), the processor 136 can determine that the user experienced poor sleep during that particular sleep cycle.

In some implementations, rather than performing the data analysis in the control box 124 with the processor 136, a digital signal processor (DSP) can be provided to analyze the data collected by the pressure transducer 146. Alternatively, the collected data can be sent to a cloud-based computing system for remote analysis.

In some implementations, the example air bed system 100 further includes a temperature controller configured to increase, decrease, or maintain a temperature of the bed 112, for example for the comfort of the user. For example, a pad (e.g., mat, layer, etc.) can be placed on top of or be part of the bed 112, or can be placed on top of or be part of one or both of the chambers 114A and 114B. Air can be pushed through the pad and vented to cool off the user on the bed 112. Additionally or alternatively, the pad can include a heating element used to keep the user warm. In some implementations, the temperature controller can receive temperature readings from the pad. The temperature controller can determine whether the temperature readings are less than or greater than some threshold range and/or value. Based on this determination, the temperature controller can actuate components to push air through the pad to cool off the user or active the heating element. In some implementations, separate pads are used for different sides of the bed 112 (e.g., corresponding to the locations of the chambers 114A and 114B) to provide for differing temperature control for the different sides of the bed 112. Each pad can be selectively controlled by the temperature controller to provide cooling or heating preferred by each user on the different sides of the bed 112. For example, a first user on a left side of the bed 112 can prefer to have their side of the bed 112 cooled during the night while a second user on a right side of the bed 112 can prefer to have their side of the bed 112 warmed during the night.

In some implementations, the user of the air bed system 100 can use an input device, such as the remote control 122 or a mobile device as described above, to input a desired temperature for a surface of the bed 112 (or for a portion of the surface of the bed 112, for example at a foot region, a lumbar or waist region, a shoulder region, and/or a head region of the bed 112). The desired temperature can be encapsulated in a command data structure that includes the desired temperature and also identifies the temperature controller as the desired component to be controlled. The command data structure can then be transmitted via Bluetooth or another suitable communication protocol (e.g., WIFI, a local network, etc.) to the processor 136. In various examples, the command data structure is encrypted before being transmitted. The temperature controller can then configure its elements to increase or decrease the temperature of the pad depending on the temperature input provided at the remote control 122 by the user.

In some implementations, data can be transmitted from a component back to the processor 136 or to one or more display devices, such as the display 126 of the remote controller 122. For example, the current temperature as determined by a sensor element of a temperature controller, the pressure of the bed, the current position of the foundation or other information can be transmitted to control box 124. The control box 124 can transmit this information to the remote control 122 to be displayed to the user (e.g., on the display 126). As described above, the control box 124 can also transmit the received information to a mobile device to be displayed in a mobile application or other graphical user interface (GUI) to the user.

In some implementations, the example air bed system 100 further includes an adjustable foundation and an articulation controller configured to adjust the position of the bed 112 by adjusting the adjustable foundation supporting the bed. For example, the articulation controller can adjust the bed 112 from a flat position to a position in which a head portion of a mattress of the bed is inclined upward (e.g., to facilitate a user sitting up in bed and/or watching television). The bed 112 can also include multiple separately articulable sections. As an illustrative example, the bed 112 can include one or more of a head portion, a lumbar/waist portion, a leg portion, and/or a foot portion, all of which can be separately articulable. As another example, portions of the bed 112 corresponding to the locations of the chambers 114A and 114B can be articulated independently from each other, to allow one user positioned on the bed 112 surface to rest in a first position (e.g., a flat position or other desired position) while a second user rests in a second position (e.g., a reclining position with the head raised at an angle from the waist or another desired position). Separate positions can also be set for two different beds (e.g., two twin beds placed next to each other). The foundation of the bed 112 can include more than one zone that can be independently adjusted.

Sometimes, the bed 112 can be adjusted to one or more user-defined positions based on user input and/or user preferences. For example, the bed 112 can automatically adjust, by the articulation controller, to one or more user-defined settings. As another example, the user can control the articulation controller to adjust the bed 112 to one or more user-defined positions. Sometimes, the bed 112 can be adjusted to one or more positions that may provide the user with improved or otherwise improve sleep and sleep quality. For example, a head portion on one side of the bed 112 can be automatically articulated, by the articulation controller, when one or more sensors of the air bed system 100 detect that a user sleeping on that side of the bed 112 is snoring. As a result, the user's snoring can be mitigated so that the snoring does not wake up another user sleeping in the bed 112.

In some implementations, the bed 112 can be adjusted using one or more devices in communication with the articulation controller or instead of the articulation controller. For example, the user can change positions of one or more portions of the bed 112 using the remote control 122 described above. The user can also adjust the bed 112 using a mobile application or other graphical user interface presented at a mobile computing device of the user.

The articulation controller can also provide different levels of massage to one or more portions of the bed 112 for one or more users. The user(s) can adjust one or more massage settings for the portions of the bed 112 using the remote control 122 and/or a mobile device in communication with the air bed system 100.

Example of a Bed in a Bedroom Environment

Figure 3:
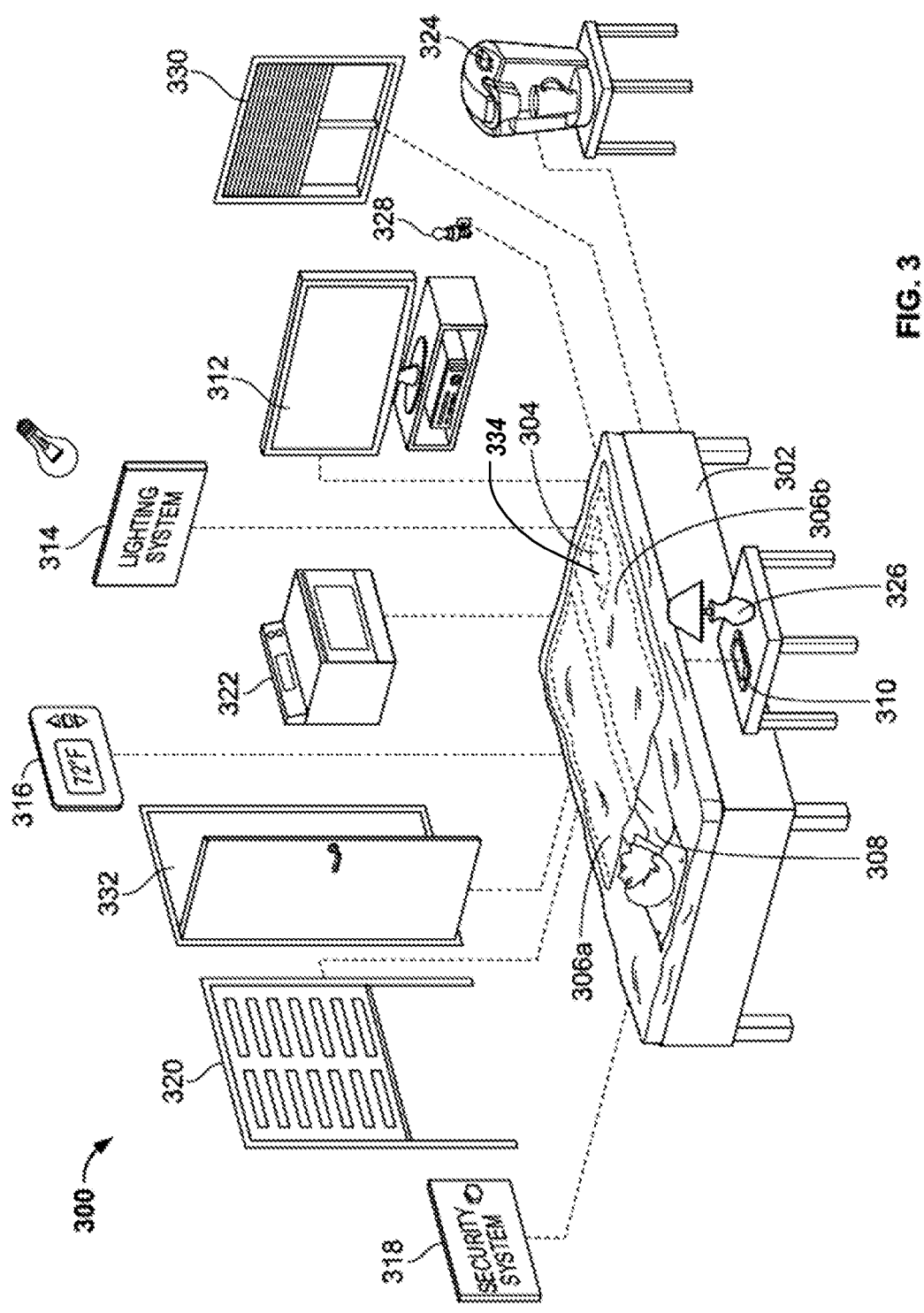
FIG. 3 shows an example environment including a bed in communication with devices located in and around a home.

FIG. 3 shows an example environment 300 including a bed 302 in communication with devices located in and around a home. In the example shown, the bed 302 includes pump 304 for controlling air pressure within two air chambers 306a and 306b (as described above). The pump 304 additionally includes circuitry 334 for controlling inflation and deflation functionality performed by the pump 304. The circuitry 334 is programmed to detect fluctuations in air pressure of the air chambers 306a-b and use the detected fluctuations to identify bed presence of a user 308, the user's sleep state, movement, and biometric signals (e.g., heartrate, respiration rate). The detected fluctuations can also be used to detect when the user 308 is snoring and whether the user 308 has sleep apnea or other health conditions. The detected fluctuations can also be used to determine an overall sleep quality of the user 308.

In the example shown, the pump 304 is located within a support structure of the bed 302 and the control circuitry 334 for controlling the pump 304 is integrated with the pump 304. In some implementations, the control circuitry 334 is physically separate from the pump 304 and is in wireless or wired communication with the pump 304. In some implementations, the pump 304 and/or control circuitry 334 are located outside of the bed 302. In some implementations, various control functions can be performed by systems located in different physical locations. For example, circuitry for controlling actions of the pump 304 can be located within a pump casing of the pump 304 while control circuitry 334 for performing other functions associated with the bed 302 can be located in another portion of the bed 302, or external to the bed 302. The control circuitry 334 located within the pump 304 can also communicate with control circuitry 334 at a remote location through a LAN or WAN (e.g., the internet). The control circuitry 334 can also be included in the control box 124 of FIGS. 1 and 2.

In some implementations, one or more devices other than, or in addition to, the pump 304 and control circuitry 334 can be utilized to identify user bed presence, sleep state, movement, biometric signals, and other information (e.g., sleep quality, health related) about the user 308. For example, the bed 302 can include a second pump, with each pump connected to a respective one of the air chambers 306a-b. For example, the pump 304 can be in fluid communication with the air chamber 306b to control inflation and deflation of the air chamber 306b as well as detect user signals for a user located over the air chamber 306b. The second pump can be in fluid communication with the air chamber 306a and used to control inflation and deflation of the air chamber 306a as well as detect user signals for a user located over the air chamber 306a.

As another example, the bed 302 can include one or more pressure sensitive pads or surface portions operable to detect movement, including user presence, motion, respiration, and heartrate. A first pressure sensitive pad can be incorporated into a surface of the bed 302 over a left portion of the bed 302, where a first user would normally be located during sleep, and a second pressure sensitive pad can be incorporated into the surface of the bed 302 over a right portion of the bed 302, where a second user would normally be located. The movement detected by the pressure sensitive pad(s) or surface portion(s) can be used by control circuitry 334 to identify user sleep state, bed presence, or biometric signals for each user. The pressure sensitive pads can also be removable rather than incorporated into the surface of the bed 302.

The bed 302 can also include one or more temperature sensors and/or array of sensors operable to detect temperatures in microclimates of the bed 302. Detected temperatures in different microclimates of the bed 302 can be used by the control circuitry 334 to determine one or more modifications to the user 308's sleep environment. For example, a temperature sensor located near a core region of the bed 302 where the user 308 rests can detect high temperature values. Such high temperature values can indicate that the user 308 is warm. To lower the user's body temperature in this microclimate, the control circuitry 334 can determine that a cooling element of the bed 302 can be activated. As another example, the control circuitry 334 can determine that a cooling unit in the home can be automatically activated to cool an ambient temperature in the environment 300.

The control circuitry 334 can also process a combination of signals sensed by different sensors that are integrated into, positioned on, or otherwise in communication with the bed 112. For example, pressure and temperature signals can be processed by the control circuitry 334 to more accurately determine one or more health conditions of the user 308 and/or sleep quality of the user 308. Acoustic signals detected by one or more microphones or other audio sensors can also be used in combination with pressure or motion sensors in order to determine when the user 308 snores, whether the user 308 has sleep apnea, and/or overall sleep quality of the user 308. Combinations of one or more other sensed signals are also possible for the control circuitry 334 to more accurately determine one or more health and/or sleep conditions of the user 308.

Accordingly, information detected by one or more sensors or other components of the bed 112 (e.g., motion information) can be processed by the control circuitry 334 and provided to one or more user devices, such as a user device 310 for presentation to the user 308 or to other users. The information can be presented in a mobile application or other graphical user interface at the user device 310. The user 308 can view different information that is processed and/or determined by the control circuitry 334 and based the signals that are detected by components of the bed 302. For example, the user 308 can view their overall sleep quality for a particular sleep cycle (e.g., the previous night), historic trends of their sleep quality, and health information. The user 308 can also adjust one or more settings of the bed 302 (e.g., increase or decrease pressure in one or more regions of the bed 302, incline or decline different regions of the bed 302, turn on or off massage features of the bed 302, etc.) using the mobile application that is presented at the user device 310.

In the example depicted in FIG. 3, the user device 310 is a mobile phone; however, the user device 310 can also be any one of a tablet, personal computer, laptop, a smartphone, a smart television (e.g., a television 312), a home automation device, or other user device capable of wired or wireless communication with the control circuitry 334, one or more other components of the bed 302, and/or one or more devices in the environment 300. The user device 310 can be in communication with the control circuitry 334 of the bed 302 through a network or through direct point-to-point communication. For example, the control circuitry 334 can be connected to a LAN (e.g., through a WIFI router) and communicate with the user device 310 through the LAN. As another example, the control circuitry 334 and the user device 310 can both connect to the Internet and communicate through the Internet. For example, the control circuitry 334 can connect to the Internet through a WIFI router and the user device 310 can connect to the Internet through communication with a cellular communication system. As another example, the control circuitry 334 can communicate directly with the user device 310 through a wireless communication protocol, such as Bluetooth. As yet another example, the control circuitry 334 can communicate with the user device 310 through a wireless communication protocol, such as ZigBee, Z-Wave, infrared, or another wireless communication protocol suitable for the application. As another example, the control circuitry 334 can communicate with the user device 310 through a wired connection such as, for example, a USB connector, serial/RS232, or another wired connection suitable for the application.

As mentioned above, the user device 310 can display a variety of information and statistics related to sleep, or user 308's interaction with the bed 302. For example, a user interface displayed by the user device 310 can present information including amount of sleep for the user 308 over a period of time (e.g., a single evening, a week, a month, etc.), amount of deep sleep, ratio of deep sleep to restless sleep, time lapse between the user 308 getting into bed and falling asleep, total amount of time spent in the bed 302 for a given period of time, heartrate over a period of time, respiration rate over a period of time, or other information related to user interaction with the bed 302 by the user 308 or one or more other users. In some implementations, information for multiple users can be presented on the user device 310, for example information for a first user positioned over the air chamber 306a can be presented along with information for a second user positioned over the air chamber 306b. In some implementations, the information presented on the user device 310 can vary according to the age of the user 308 so that the information presented evolves with the age of the user 308.

The user device 310 can also be used as an interface for the control circuitry 334 of the bed 302 to allow the user 308 to enter information and/or adjust one or more settings of the bed 302. The information entered by the user 308 can be used by the control circuitry 334 to provide better information to the user 308 or to various control signals for controlling functions of the bed 302 or other devices. For example, the user 308 can enter information such as weight, height, and age of the user 308. The control circuitry 334 can use this information to provide the user 308 with a comparison of the user 308's tracked sleep information to sleep information of other people having similar weights, heights, and/or ages as the user 308. The control circuitry 308 can also use this information to accurately determine overall sleep quality and/or health of the user 308 based on information detected by components (e.g., sensors) of the bed 302.

The user 308 may also use the user device 310 as an interface for controlling air pressure of the air chambers 306a and 306b, various recline or incline positions of the bed 302, temperature of one or more surface temperature control devices of the bed 302, or for allowing the control circuitry 334 to generate control signals for other devices (as described below).

The control circuitry 334 may also communicate with other devices or systems, including but not limited to the television 312, a lighting system 314, a thermostat 316, a security system 318, home automation devices, and/or other household devices (e.g., an oven 322, a coffee maker 324, a lamp 326, a nightlight 328). Other examples of devices and/or systems include a system for controlling window blinds 330, devices for detecting or controlling states of one or more doors 332 (such as detecting if a door is open, detecting if a door is locked, or automatically locking a door), and a system for controlling a garage door 320 (e.g., control circuitry 334 integrated with a garage door opener for identifying an open or closed state of the garage door 320 and for causing the garage door opener to open or close the garage door 320). Communications between the control circuitry 334 and other devices can occur through a network (e.g., a LAN or the Internet) or as point-to-point communication (e.g., BLUETOOTH, radio communication, or a wired connection). Control circuitry 334 of different beds 302 can also communicate with different sets of devices. For example, a kid's bed may not communicate with and/or control the same devices as an adult bed. In some embodiments, the bed 302 can evolve with the age of the user such that the control circuitry 334 of the bed 302 communicates with different devices as a function of age of the user of that bed 302.

The control circuitry 334 can receive information and inputs from other devices/systems and use the received information and inputs to control actions of the bed 302 and/or other devices. For example, the control circuitry 334 can receive information from the thermostat 316 indicating a current environmental temperature for a house or room in which the bed 302 is located. The control circuitry 334 can use the received information (along with other information, such as signals detected from one or more sensors of the bed 302) to determine if a temperature of all or a portion of the surface of the bed 302 should be raised or lowered. The control circuitry 334 can then cause a heating or cooling mechanism of the bed 302 to raise or lower the temperature of the surface of the bed 302. The control circuitry 334 can also cause a heating or cooling unit of the house or room in which the bed 302 is located to raise or lower the ambient temperature surrounding the bed 302. Thus, by adjusting the temperature of the bed 302 and/or the room in which the bed 302 is located, the user 308 can experience more improved sleep quality and comfort.

As an example, the user 308 can indicate a desired sleeping temperature of 74 degrees while a second user of the bed 302 indicates a desired sleeping temperature of 72 degrees. The thermostat 316 can transmit signals indicating room temperature at predetermined times to the control circuitry 334. The thermostat 316 can also send a continuous stream of detected temperature values of the room to the control circuitry 334. The transmitted signal(s) can indicate to the control circuitry 334 that the current temperature of the bedroom is 72 degrees. The control circuitry 334 can identify that the user 308 has indicated a desired sleeping temperature of 74 degrees, and can accordingly send control signals to a heating pad located on the user 308's side of the bed to raise the temperature of the portion of the surface of the bed 302 where the user 308 is located until the user 308's desired temperature is achieved. Moreover, the control circuitry 334 can sent control signals to the thermostat 316 and/or a heating unit in the house to raise the temperature in the room in which the bed 302 is located.

The control circuitry 334 can generate control signals to control other devices and propagate the control signals to the other devices. The control signals can be generated based on information collected by the control circuitry 334, including information related to user interaction with the bed 302 by the user 308 and/or one or more other users. Information collected from other devices other than the bed 302 can also be used when generating the control signals. For example, information relating to environmental occurrences (e.g., environmental temperature, environmental noise level, and environmental light level), time of day, time of year, day of the week, or other information can be used when generating control signals for various devices in communication with the control circuitry 334 of the bed 302.

For example, information on the time of day can be combined with information relating to movement and bed presence of the user 308 to generate control signals for the lighting system 314. The control circuitry 334 can, based on detected pressure signals of the user 308 on the bed 302, determine when the user 308 is presently in the bed 302 and when the user 308 falls asleep. Once the control circuitry 334 determines that the user has fallen asleep, the control circuitry 334 can transmit control signals to the lighting system 314 to turn off lights in the room in which the bed 302 is located, to lower the window blinds 330 in the room, and/or to activate the nightlight 328. Moreover, the control circuitry 334 can receive input from the user 308 (e.g., via the user device 310) that indicates a time at which the user 308 would like to wake up. When that time approaches, the control circuitry 334 can transmit control signals to one or more devices in the environment 300 to control devices that may cause the user 308 to wake up. For example, the control signals can be sent to a home automation device that controls multiple devices in the home. The home automation device can be instructed, by the control circuitry 334, to raise the window blinds 330, turn off the nightlight 328, turn on lighting beneath the bed 302, start the coffee machine 324, change a temperature in the house via the thermostat 316, or perform some other home automation. The home automation device can also be instructed to activate an alarm that can cause the user 308 to wake up. Sometimes, the user 308 can input information at the user device 310 that indicates what actions can be taken by the home automation device or other devices in the environment 300.

In some implementations, rather than or in addition to providing control signals for other devices, the control circuitry 334 can provide collected information (e.g., information related to user movement, bed presence, sleep state, or biometric signals) to one or more other devices to allow the one or more other devices to utilize the collected information when generating control signals. For example, the control circuitry 334 of the bed 302 can provide information relating to user interactions with the bed 302 by the user 308 to a central controller (not shown) that can use the provided information to generate control signals for various devices, including the bed 302.

The central controller can, for example, be a hub device that provides a variety of information about the user 308 and control information associated with the bed 302 and other devices in the house. The central controller can include sensors that detect signals that can be used by the control circuitry 334 and/or the central controller to determine information about the user 308 (e.g., biometric or other health data, sleep quality). The sensors can detect signals including such as ambient light, temperature, humidity, volatile organic compound(s), pulse, motion, and audio. These signals can be combined with signals detected by sensors of the bed 302 to determine accurate information about the user 308's health and sleep quality. The central controller can provide controls (e.g., user-defined, presets, automated, user initiated) for the bed 302, determining and viewing sleep quality and health information, a smart alarm clock, a speaker or other home automation device, a smart picture frame, a nightlight, and one or more mobile applications that the user 308 can install and use at the central controller. The central controller can include a display screen that outputs information and receives user input. The display can output information such as the user 308's health, sleep quality, weather, security integration features, lighting integration features, heating and cooling integration features, and other controls to automate devices in the house. The central controller can operate to provide the user 308 with functionality and control of multiple different types of devices in the house as well as the user 308's bed 302.

As an illustrative example of FIG. 3, the control circuitry 334 integrated with the pump 304 can detect a feature of a mattress of the bed 302, such as an increase in pressure in the air chamber 306b, and use this detected increase to determine that the user 308 is present on the bed 302. The control circuitry 334 may also identify a heartrate or respiratory rate for the user 308 to identify that the increased pressure is due to a person sitting, laying, or resting on the bed 302, rather than an inanimate object (e.g., a suitcase) having been placed on the bed 302. In some implementations, the information indicating user bed presence can be combined with other information to identify a current or future likely state for the user 308. For example, a detected user bed presence at 11:00 am can indicate that the user is sitting on the bed (e.g., to tie her shoes, or to read a book) and does not intend to go to sleep, while a detected user bed presence at 10:00 pm can indicate that the user 308 is in bed for the evening and is intending to fall asleep soon. As another example, if the control circuitry 334 detects that the user 308 has left the bed 302 at 6:30 am (e.g., indicating that the user 308 has woken up for the day), and then later detects presence of the user 308 at 7:30 am on the bed 302, the control circuitry 334 can use this information that the newly detected presence is likely temporary (e.g., while the user 308 ties her shoes before heading to work) rather than an indication that the user 308 is intending to stay on the bed 302 for an extended period of time.

If the control circuitry 334 determines that the user 308 is likely to remain on the bed 302 for an extended period of time, the control circuitry 334 can determine one or more home automation controls that can aid the user 308 in falling asleep and experience improved sleep quality throughout the user 308's sleep cycle. For example, the control circuitry 334 can communicate with security system 318 to ensure that doors are locked. The control circuitry 334 can communicate with the oven 322 to ensure that the oven 322 is turned off. The control circuitry 334 can also communicate with the lighting system 314 to dim or otherwise turn off lights in the room in which the bed 302 is located and/or throughout the house, and the control circuitry 334 can communicate with the thermostat 316 to ensure that the house is at a desired temperature of the user 308. The control circuitry 334 can also determine one or more adjustments that can be made to the bed 302 to facilitate the user 308 falling asleep and staying asleep (e.g., changing a position of one or more regions of the bed 302, foot warming, massage features, pressure/firmness in one or more regions of the bed 302, etc.).

In some implementations, the control circuitry 334 may use collected information (including information related to user interaction with the bed 302 by the user 308, environmental information, time information, and user input) to identify use patterns for the user 308. For example, the control circuitry 334 can use information indicating bed presence and sleep states for the user 308 collected over a period of time to identify a sleep pattern for the user. The control circuitry 334 can identify that the user 308 generally goes to bed between 9:30 pm and 10:00 pm, generally falls asleep between 10:00 pm and 11:00 pm, and generally wakes up between 6:30 am and 6:45 am, based on information indicating user presence and biometrics for the user 308 collected over a week or a different time period. The control circuitry 334 can use identified patterns of the user 308 to better process and identify user interactions with the bed 302.

Given the above example user bed presence, sleep, and wake patterns for the user 308, if the user 308 is detected as being on the bed 302 at 3:00 pm, the control circuitry 334 can determine that the user 308's presence on the bed 302 is temporary, and use this determination to generate different control signals than if the control circuitry 334 determined the user 308 was in bed for the evening (e.g., at 3:00 pm, a head region of the bed 302 can be raised to facilitate reading or watching TV while in the bed 302, whereas in the evening, the bed 302 can be adjusted to a flat position to facilitate falling asleep). As another example, if the control circuitry 334 detects that the user 308 got out of bed at 3:00 am, the control circuitry 334 can use identified patterns for the user 308 to determine the user has gotten up temporarily (e.g., to use the bathroom, get a glass of water). The control circuitry 334 can turn on underbed lighting to assist the user 308 in carefully moving around the bed 302 and room. By contrast, if the control circuitry 334 identifies that the user 308 got out of the bed 302 at 6:40 am, the control circuitry 334 can determine the user 308 is up for the day and generate a different set of control signals (e.g., the control circuitry 334 can turn on light 326 near the bed 302 and/or raise the window blinds 330). For other users, getting out of the bed 302 at 3:00 am can be a normal wake-up time, which the control circuitry 334 can learn and respond to accordingly. Moreover, if the bed 302 is occupied by two users, the control circuitry 334 can learn and respond to the patterns of each of the users.

The bed 302 can also generate control signals based on communication with one or more devices. As an illustrative example, the control circuitry 334 can receive an indication from the television 312 that the television 312 is turned on. If the television 312 is located in a different room than the bed 302, the control circuitry 334 can generate a control signal to turn the television 312 off upon making a determination that the user 308 has gone to bed for the evening or otherwise is remaining in the room with the bed 302. If presence of the user 308 is detected on the bed 302 during a particular time range (e.g., between 8:00 pm and 7:00 am) and persists for longer than a threshold period of time (e.g., 10 minutes), the control circuitry 334 can determine the user 308 is in bed for the evening. If the television 312 is on, as described above, the control circuitry 334 can generate a control signal to turn the television 312 off. The control signals can be transmitted to the television (e.g., through a directed communication link or through a network, such as WIFI). As another example, rather than turning off the television 312 in response to detection of user bed presence, the control circuitry 334 can generate a control signal that causes the volume of the television 312 to be lowered by a pre-specified amount.

As another example, upon detecting that the user 308 has left the bed 302 during a specified time range (e.g., between 6:00 am and 8:00 am), the control circuitry 334 can generate control signals to cause the television 312 to turn on and tune to a pre-specified channel (e.g., the user 308 indicated a preference for watching morning news upon getting out of bed). The control circuitry 334 can accordingly generate and transmit the control signal to the television 312 (which can be stored at the control circuitry 334, the television 312, or another location). As another example, upon detecting that the user 308 has gotten up for the day, the control circuitry 334 can generate and transmit control signals to cause the television 312 to turn on and begin playing a previously recorded program from a digital video recorder (DVR) in communication with the television 312.

As another example, if the television 312 is in the same room as the bed 302, the control circuitry 334 may not cause the television 312 to turn off in response to detection of user bed presence. Rather, the control circuitry 334 can generate and transmit control signals to cause the television 312 to turn off in response to determining that the user 308 is asleep. For example, the control circuitry 334 can monitor biometric signals of the user 308 (e.g., motion, heartrate, respiration rate) to determine that the user 308 has fallen asleep. Upon detecting that the user 308 is sleeping, the control circuitry 334 generates and transmits a control signal to turn the television 312 off. As another example, the control circuitry 334 can generate the control signal to turn off the television 312 after a threshold period of time has passed since the user 308 has fallen asleep (e.g., 10 minutes after the user has fallen asleep). As another example, the control circuitry 334 generates control signals to lower the volume of the television 312 after determining that the user 308 is asleep. As yet another example, the control circuitry 334 generates and transmits a control signal to cause the television to gradually lower in volume over a period of time and then turn off in response to determining that the user 308 is asleep. Any of the control signals described above in reference to the television 312 can also be determined by the central controller previously described.

In some implementations, the control circuitry 334 can similarly interact with other media devices, such as computers, tablets, mobile phones, smart phones, wearable devices, stereo systems, etc. For example, upon detecting that the user 308 is asleep, the control circuitry 334 can generate and transmit a control signal to the user device 310 to cause the user device 310 to turn off, or turn down the volume on a video or audio file being played by the user device 310.

The control circuitry 334 can additionally communicate with the lighting system 314, receive information from the lighting system 314, and generate control signals for controlling functions of the lighting system 314. For example, upon detecting user bed presence on the bed 302 during a certain time frame (e.g., between 8:00 pm and 7:00 am) that lasts for longer than a threshold period of time (e.g., 10 minutes), the control circuitry 334 of the bed 302 can determine that the user 308 is in bed for the evening and generate control signals to cause lights in one or more rooms other than the room in which the bed 302 is located to switch off. The control circuitry 334 can generate and transmit control signals to turn off lights in all common rooms, but not in other bedrooms. As another example, the control signals can indicate that lights in all rooms other than the room in which the bed 302 is located are to be turned off, while one or more lights located outside of the house containing the bed 302 are to be turned on. The control circuitry 334 can generate and transmit control signals to cause the nightlight 328 to turn on in response to determining user 308 bed presence or that the user 308 is asleep. The control circuitry 334 can also generate first control signals for turning off a first set of lights (e.g., lights in common rooms) in response to detecting user bed presence, and second control signals for turning off a second set of lights (e.g., lights in the room where the bed 302 is located) when detecting that the user 308 is asleep.

In some implementations, in response to determining that the user 308 is in bed for the evening, the control circuitry 334 of the bed 302 can generate control signals to cause the lighting system 314 to implement a sunset lighting scheme in the room in which the bed 302 is located. A sunset lighting scheme can include, for example, dimming the lights (either gradually over time, or all at once) in combination with changing the color of the light in the bedroom environment, such as adding an amber hue to the lighting in the bedroom. The sunset lighting scheme can help to put the user 308 to sleep when the control circuitry 334 has determined that the user 308 is in bed for the evening. Sometimes, the control signals can cause the lighting system 314 to dim the lights or change color of the lighting in the bedroom environment, but not both.

The control circuitry 334 can also implement a sunrise lighting scheme when the user 308 wakes up in the morning. The control circuitry 334 can determine that the user 308 is awake for the day, for example, by detecting that the user 308 has gotten off the bed 302 (e.g., is no longer present on the bed 302) during a specified time frame (e.g., between 6:00 am and 8:00 am). The control circuitry 334 can also monitor movement, heartrate, respiratory rate, or other biometric signals of the user 308 to determine that the user 308 is awake or is waking up, even though the user 308 has not gotten out of bed. If the control circuitry 334 detects that the user is awake or waking up during a specified timeframe, the control circuitry 334 can determine that the user 308 is awake for the day. The specified timeframe can be, for example, based on previously recorded user bed presence information collected over a period of time (e.g., two weeks) that indicates that the user 308 usually wakes up for the day between 6:30 am and 7:30 am. In response to the control circuitry 334 determining that the user 308 is awake, the control circuitry 334 can generate control signals to cause the lighting system 314 to implement the sunrise lighting scheme in the bedroom in which the bed 302 is located. The sunrise lighting scheme can include, for example, turning on lights (e.g., the lamp 326, or other lights in the bedroom). The sunrise lighting scheme can further include gradually increasing the level of light in the room where the bed 302 is located (or in one or more other rooms). The sunrise lighting scheme can also include only turning on lights of specified colors. The sunrise lighting scheme can include lighting the bedroom with blue light to gently assist the user 308 in waking up and becoming active.

The control circuitry 334 may also generate different control signals for controlling actions of components depending on a time of day that user interactions with the bed 302 are detected. For example, the control circuitry 334 can use historical user interaction information to determine that the user 308 usually falls asleep between 10:00 pm and 11:00 pm and usually wakes up between 6:30 am and 7:30 am on weekdays. The control circuitry 334 can use this information to generate a first set of control signals for controlling the lighting system 314 if the user 308 is detected as getting out of bed at 3:00 am (e.g., turn on lights that guide the user 308 to a bathroom or kitchen) and to generate a second set of control signals for controlling the lighting system 314 if the user 308 is detected as getting out of bed after 6:30 am.

In some implementations, if the user 308 is detected as getting out of bed prior to a specified morning rise time for the user 308, the control circuitry 334 can cause the lighting system 314 to turn on lights that are dimmer than lights that are turned on by the lighting system 314 if the user 308 is detected as getting out of bed after the specified morning rise time. Causing the lighting system 314 to only turn on dim lights when the user 308 gets out of bed during the night (e.g., prior to normal rise time for the user 308) can prevent other occupants of the house from being woken up by the lights while still allowing the user 308 to see in order to reach their destination in the house.

The historical user interaction information for interactions between the user 308 and the bed 302 can be used to identify user sleep and awake timeframes. For example, user bed presence times and sleep times can be determined for a set period of time (e.g., two weeks, a month, etc.). The control circuitry 334 can identify a typical time range or timeframe in which the user 308 goes to bed, a typical timeframe for when the user 308 falls asleep, and a typical timeframe for when the user 308 wakes up (and in some cases, different timeframes for when the user 308 wakes up and when the user 308 actually gets out of bed). Buffer time may be added to these timeframes. For example, if the user is identified as typically going to bed between 10:00 pm and 10:30 pm, a buffer of a half hour in each direction can be added to the timeframe such that any detection of the user getting in bed between 9:30 pm and 11:00 pm is interpreted as the user 308 going to bed for the evening. As another example, detection of bed presence of the user 308 starting from a half hour before the earliest typical time that the user 308 goes to bed extending until the typical wake up time (e.g., 6:30 am) for the user 308 can be interpreted as the user 308 going to bed for the evening. For example, if the user 308 typically goes to bed between 10:00 pm and 10:30 pm, if the user 308's bed presence is sensed at 12:30 am one night, that can be interpreted as the user 308 getting into bed for the evening even though this is outside of the user 308's typical time-frame for going to bed because it has occurred prior to the user 308's normal wake up time. In some implementations, different timeframes are identified for different times of year (e.g., earlier bed time during winter vs. summer) or at different times of the week (e.g., user 308 wakes up earlier on weekdays than on weekends).

The control circuitry 334 can distinguish between the user 308 going to bed for an extended period (e.g., for the night) as opposed to being present on the bed 302 for a shorter period (e.g., for a nap) by sensing duration of presence of the user 308 (e.g., by detecting pressure and/or temperature signals of the user 308 on the bed 302 by sensors integrated into the bed 302). In some examples, the control circuitry 334 can distinguish between the user 308 going to bed for an extended period (e.g., for the night) versus going to bed for a shorter period (e.g., for a nap) by sensing duration of the user 308's sleep. The control circuitry 334 can set a time threshold whereby if the user 308 is sensed on the bed 302 for longer than the threshold, the user 308 is considered to have gone to bed for the night. In some examples, the threshold can be about 2 hours, whereby if the user 308 is sensed on the bed 302 for greater than 2 hours, the control circuitry 334 registers that as an extended sleep event. In other examples, the threshold can be greater than or less than two hours. The threshold can be determined based on historic trends indicating how long the user 302 usually sleeps or otherwise stays on the bed 302.

The control circuitry 334 can detect repeated extended sleep events to automatically determine a typical bed time range of the user 308, without requiring the user 308 to enter a bed time range. This can allow the control circuitry 334 to accurately estimate when the user 308 is likely to go to bed for an extended sleep event, regardless of whether the user 308 typically goes to bed using a traditional sleep schedule or a non-traditional sleep schedule. The control circuitry 334 can then use knowledge of the bed time range of the user 308 to control one or more components (including components of the bed 302 and/or non-bed peripherals) based on sensing bed presence during the bed time range or outside of the bed time range.

The control circuitry 334 can automatically determine the bed time range of the user 308 without requiring user inputs. The control circuitry 334 may also determine the bed time range automatically and in combination with user inputs (e.g., using signals sensed by sensors of the bed 302 and/or the central controller). The control circuitry 334 can set the bed time range directly according to user inputs. The control circuitry 334 can associate different bed times with different days of the week. In each of these examples, the control circuitry 334 can control components (e.g., the lighting system 314, thermostat 316, security system 318, oven 322, coffee maker 324, lamp 326, nightlight 328), as a function of sensed bed presence and the bed time range.

The control circuitry 334 can also determine control signals to be transmitted to the thermostat 316 based on user-inputted preferences and/or maintaining improved or preferred sleep quality of the user 308. For example, the control circuitry 334 can determine, based on historic sleep patterns and quality of the user 308 and by applying machine learning models, that the user 308 experiences their best sleep when the bedroom is at 74 degrees. The control circuitry 334 can receive temperature signals from devices and/or sensors in the bedroom indicating a bedroom tem-perature. When the temperature is below 74 degrees, the control circuitry 334 can determine control signals that cause the thermostat 316 to activate a heating unit to raise the temperature to 74 degrees in the bedroom. When the temperature is above 74 degrees, the control circuitry 334 can determine control signals that cause the thermostat 316 to activate a cooling unit to lower the temperature back to 74 degrees. Sometimes, the control circuitry 334 can determine control signals that cause the thermostat 316 to maintain the bedroom within a temperature range intended to keep the user 308 in particular sleep states and/or transition to next preferred sleep states.

Similarly, the control circuitry 334 can generate control signals to cause heating or cooling elements on the surface of the bed 302 to change temperature at various times, either in response to user interaction with the bed 302, at various pre-programmed times, based on user preference, and/or in response to detecting microclimate temperatures of the user 308 on the bed 302. For example, the control circuitry 334 can activate a heating element to raise the temperature of one side of the surface of the bed 302 to 73 degrees when it is detected that the user 308 has fallen asleep. As another example, upon determining that the user 308 is up for the day, the control circuitry 334 can turn off a heating or cooling element. The user 308 can pre-program various times at which the temperature at the bed surface should be raised or lowered. As another example, temperature sensors on the bed surface can detect microclimates of the user 308. When a detected microclimate drops below a predetermined threshold temperature, the control circuitry 334 can activate a heating element to raise the user 308's body temperature, thereby improving the user 308's comfortability, maintain-ing their sleep cycle, transitioning the user 308 to a next preferred sleep state, and/or maintaining or improving the user 308's sleep quality.

In response to detecting user bed presence and/or that the user 308 is asleep, the control circuitry 334 can also cause the thermostat 316 to change the temperature in different rooms to different values. Other control signals are also possible, and can be based on user preference and user input. Moreover, the control circuitry 334 can receive temperature information from the thermostat 316 and use this information to control functions of the bed 302 or other devices (e.g., adjusting temperatures of heating elements of the bed 302, such as a foot warming pad). The control circuitry 334 may also generate and transmit control signals for controlling other temperature control systems, such as floor heating elements in the bedroom or other rooms.

The control circuitry 334 can communicate with the security system 318, receive information from the security system 318, and generate control signals for controlling functions of the security system 318. For example, in response to detecting that the user 308 in is bed for the evening, the control circuitry 334 can generate control signals to cause the security system 318 to engage or disengage security functions. As another example, the control circuitry 334 can generate and transmit control signals to cause the security system 318 to disable in response to determining that the user 308 is awake for the day (e.g., user 308 is no longer present on the bed 302).

The control circuitry 334 can also receive alerts from the security system 318 and indicate the alert to the user 308. For example, the security system can detect a security breach (e.g., someone opened the door 332 without entering the security code, someone opened a window when the security system 318 is engaged) and communicate the security breach to the control circuitry 334. The control circuitry 334 can then generate control signals to alert the user 308, such as causing the bed 302 to vibrate, causing portions of the bed 302 to articulate (e.g., the head section to raise or lower), causing the lamp 326 to flash on and off at regular intervals, etc. The control circuitry 334 can also alert the user 308 of one bed 302 about a security breach in another bedroom, such as an open window in a kid's bedroom. The control circuitry 334 can send an alert to a garage door controller (e.g., to close and lock the door). The control circuitry 334 can send an alert for the security to be disengaged. The control circuitry 334 can also set off a smart alarm or other alarm device/clock near the bed 302. The control circuitry 334 can transmit a push notification, text message, or other indication of the security breach to the user device 310. Also, the control circuitry 334 can transmit a notification of the security breach to the central controller, which can then determine one or more responses to the security breach.

The control circuitry 334 can additionally generate and transmit control signals for controlling the garage door 320 and receive information indicating a state of the garage door 320 (e.g., open or closed). The control circuitry 334 can also request information on a current state of the garage door 320. If the control circuitry 334 receives a response (e.g., from the garage door opener) that the garage door 320 is open, the control circuitry 334 can notify the user 308 that the garage door is open (e.g., by displaying a notification or other message at the user device 310, outputting a notification at the central controller), and/or generate a control signal to cause the garage door opener to close the door. The control circuitry 334 can also cause the bed 302 to vibrate, cause the lighting system 314 to flash lights in the bedroom, etc. Control signals can also vary depend on the age of the user 308. Similarly, the control circuitry 334 can similarly send and receive communications for controlling or receiving state information associated with the door 332 or the oven 322.

In some implementations, different alerts can be generated for different events. For example, the control circuitry 334 can cause the lamp 326 (or other lights, via the lighting system 314) to flash in a first pattern if the security system 318 has detected a breach, flash in a second pattern if garage door 320 is on, flash in a third pattern if the door 332 is open, flash in a fourth pattern if the oven 322 is on, and flash in a fifth pattern if another bed has detected that a user 308 of that bed has gotten up (e.g., a child has gotten out of bed in the middle of the night as sensed by a sensor in the child's bed). Other examples of alerts include a smoke detector detecting smoke (and communicating this detection to the control circuitry 334), a carbon monoxide tester, a heater malfunctioning, or an alert from another device capable of communicating with the control circuitry 334 and detecting an occurrence to bring to the user 308's attention.

The control circuitry 334 can also communicate with a system or device for controlling a state of the window blinds 330. For example, in response to determining that the user 308 is up for the day or that the user 308 set an alarm to wake up at a particular time, the control circuitry 334 can generate and transmit control signals to cause the window blinds 330 to open. By contrast, if the user 308 gets out of bed prior to a normal rise time for the user 308, the control circuitry 334 can determine that the user 308 is not awake for the day and may not generate control signals that cause the window blinds 330 to open. The control circuitry 334 can also generate and transmit control signals that cause a first set of blinds to close in response to detecting user bed presence and a second set of blinds to close in response to detecting that the user 308 is asleep.

As other examples, in response to determining that the user 308 is awake for the day, the control circuitry 334 can generate and transmit control signals to the coffee maker 324 to cause the coffee maker 324 to brew coffee. The control circuitry 334 can generate and transmit control signals to the oven 322 to cause the oven 322 to begin preheating. The control circuitry 334 can use information indicating that the user 308 is awake for the day along with information indicating that the time of year is currently winter and/or that the outside temperature is below a threshold value to generate and transmit control signals to cause a car engine block heater to turn on. The control circuitry 334 can generate and transmit control signals to cause devices to enter a sleep mode in response to detecting user bed presence, or in response to detecting that the user 308 is asleep (e.g., causing a mobile phone of the user 308 to switch into sleep or night mode so that notifications are muted to not disturb the user 308's sleep). Later, upon determining that the user 308 is up for the day, the control circuitry 334 can generate and transmit control signals to cause the mobile phone to switch out of sleep/night mode.

The control circuitry 334 can also communicate with one or more noise control devices. For example, upon determining that the user 308 is in bed for the evening, or that the user 308 is asleep (e.g., based on pressure signals received from the bed 302, audio/decibel signals received from audio sensors positioned on or around the bed 302), the control circuitry 334 can generate and transmit control signals to cause noise cancelation devices to activate. The noise cancelation devices can be part of the bed 302 or located in the bedroom. Upon determining that the user 308 is in bed for the evening or that the user 308 is asleep, the control circuitry 334 can generate and transmit control signals to turn the volume on, off, up, or down, for one or more sound generating devices, such as a stereo system radio, television, computer, tablet, mobile phone, etc.

Additionally, functions of the bed 302 can be controlled by the control circuitry 334 in response to user interactions. For example, the articulation controller can adjust the bed 302 from a flat position to a position in which a head portion of a mattress of the bed 302 is inclined upward (e.g., to facilitate a user sitting up in bed, reading, and/or watching television). Sometimes, the bed 302 includes multiple separately articulable sections. Portions of the bed corresponding to the locations of the air chambers 306a and 306b can be articulated independently from each other, to allow one person to rest in a first position (e.g., a flat position) while a second person rests in a second position (e.g., a reclining position with the head raised at an angle from the waist). Separate positions can be set for two different beds (e.g., two twin beds placed next to each other). The foundation of the bed 302 can include more than one zone that can be independently adjusted. The articulation controller can also provide different levels of massage to one or more users on the bed 302 or cause the bed to vibrate to communicate alerts to the user 308 as described above.

The control circuitry 334 can adjust positions (e.g., incline and decline positions for the user 308 and/or an additional user) in response to user interactions with the bed 302 (e.g., causing the articulation controller to adjust to a first recline position in response to sensing user bed presence). The control circuitry 334 can cause the articulation controller to adjust the bed 302 to a second recline position (e.g., a less reclined, or flat position) in response to determining that the user 308 is asleep. As another example, the control circuitry 334 can receive a communication from the television 312 indicating that the user 308 has turned off the television 312, and in response, the control circuitry 334 can cause the articulation controller to adjust the bed position to a preferred user sleeping position (e.g., due to the user turning off the television 312 while the user 308 is in bed indicating the user 308 wishes to go to sleep).

In some implementations, the control circuitry 334 can control the articulation controller to wake up one user without waking another user of the bed 302. For example, the user 308 and a second user can each set distinct wakeup times (e.g., 6:30 am and 7:15 am respectively). When the wakeup time for the user 308 is reached, the control circuitry 334 can cause the articulation controller to vibrate or change the position of only a side of the bed on which the user 308 is located. When the wakeup time for the second user is reached, the control circuitry 334 can cause the articulation controller to vibrate or change the position of only the side of the bed on which the second user is located. Alternatively, when the second wakeup time occurs, the control circuitry 334 can utilize other methods (such as audio alarms, or turning on the lights) to wake the second user since the user 308 is already awake and therefore will not be disturbed when the control circuitry 334 attempts to wake the second user.

Still referring to FIG. 3, the control circuitry 334 for the bed 302 can utilize information for interactions with the bed 302 by multiple users to generate control signals for controlling functions of various other devices. For example, the control circuitry 334 can wait to generate control signals for devices until both the user 308 and a second user are detected in the bed 302. The control circuitry 334 can generate a first set of control signals to cause the lighting system 314 to turn off a first set of lights upon detecting bed presence of the user 308 and generate a second set of control signals for turning off a second set of lights in response to detecting bed presence of a second user. The control circuitry 334 can also wait until it has been determined that both users are awake for the day before generating control signals to open the window blinds 330. One or more other home automation control signals can be determined and generated by the control circuitry 334, the user device 310, and/or the central controller.

Examples of Data Processing Systems Associated with a Bed

Described are example systems and components for data processing tasks that are, for example, associated with a bed. In some cases, multiple examples of a particular component or group of components are presented. Some examples are redundant and/or mutually exclusive alternatives. Connections between components are shown as examples to illustrate possible network configurations for allowing communication between components. Different formats of connections can be used as technically needed/desired. The connections generally indicate a logical connection that can be created with any technologically feasible format. For example, a network on a motherboard can be created with a printed circuit board, wireless data connections, and/or other types of network connections. Some logical connections are not shown for clarity (e.g., connections with power supplies and/or computer readable memory).

Figures 4A, 4B:
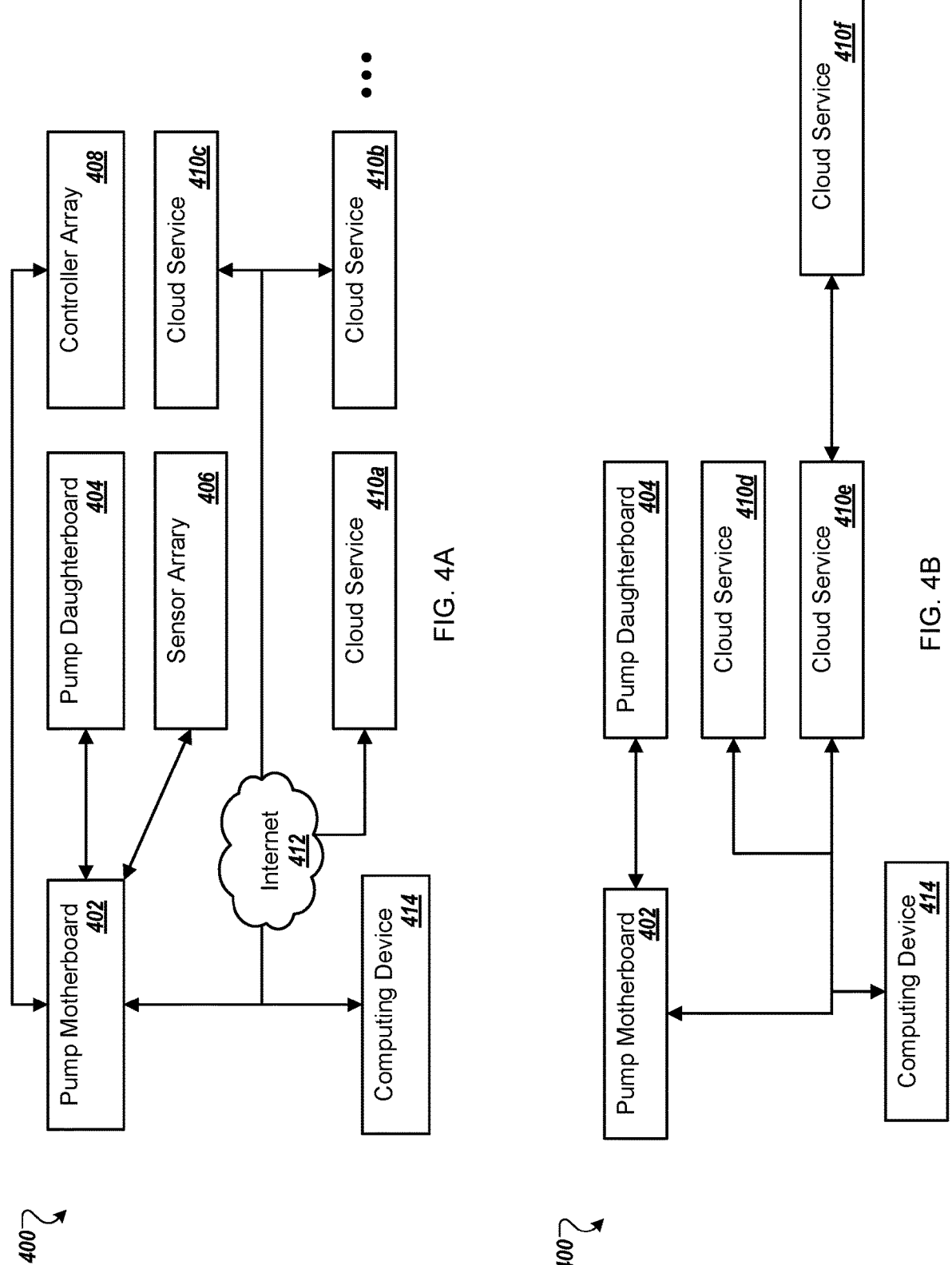
FIGS. 4A and 4B are block diagrams of example data processing systems that can be associated with a bed.

FIG. 4A is a block diagram of an example data processing system 400 that can be associated with a bed system, including those described above (e.g., see FIGS. 1-3). The system 400 includes a pump motherboard 402 and a pump daughterboard 404. The system 400 includes a sensor array 406 having one or more sensors configured to sense physical phenomenon of the environment and/or bed, and to report sensing back to the pump motherboard 402 (e.g., for analysis). The sensor array 406 can include one or more different types of sensors, including but not limited to pressure, temperature, light, movement (e.g. motion), and audio. The system 400 also includes a controller array 408 that can include one or more controllers configured to control logic-controlled devices of the bed and/or environment (e.g., home automation devices, security systems light systems, and other devices described in FIG. 3). The pump motherboard 400 can be in communication with computing devices 414 and cloud services 410 over local networks (e.g., Internet 412) or otherwise as is technically appropriate.

In FIG. 4A, the pump motherboard 402 and daughterboard 404 are communicably coupled. They can be conceptually described as a center or hub of the system 400, with the other components conceptually described as spokes of the system 400. This can mean that each spoke component communicates primarily or exclusively with the pump motherboard 402. For example, a sensor of the sensor array 406 may not be configured to, or may not be able to, communicate directly with a corresponding controller. Instead, the sensor can report a sensor reading to the motherboard 402, and the motherboard 402 can determine that, in response, a controller of the controller array 408 should adjust some parameters of a logic controlled device or otherwise modify a state of one or more peripheral devices.

One advantage of a hub-and-spoke network configuration, or a star-shaped network, is a reduction in network traffic compared to, for example, a mesh network with dynamic routing. If a particular sensor generates a large, continuous stream of traffic, that traffic is transmitted over one spoke to the motherboard 402. The motherboard 402 can marshal and condense that data to a smaller data format for retransmission for storage in a cloud service 410. Additionally or alternatively, the motherboard 402 can generate a single, small, command message to be sent down a different spoke in response to the large stream. For example, if the large stream of data is a pressure reading transmitted from the sensor array 406 a few times a second, the motherboard 402 can respond with a single command message to the controller array 408 to increase the pressure in an air chamber of the bed. In this case, the single command message can be orders of magnitude smaller than the stream of pressure readings.

As another advantage, a hub-and-spoke network configuration can allow for an extensible network that accommodates components being added, removed, failing, etc. This can allow more, fewer, or different sensors in the sensor array 406, controllers in the controller array 408, computing devices 414, and/or cloud services 410. For example, if a particular sensor fails or is deprecated by a newer version, the system 400 can be configured such that only the motherboard 402 needs to be updated about the replacement sensor. This can allow product differentiation where the same motherboard 402 can support an entry level product with fewer sensors and controllers, a higher value product with more sensors and controllers, and customer personalization where a customer can add their own selected components to the system 400.

Additionally, a line of air bed products can use the system 400 with different components. In an application in which every air bed in the product line includes both a central logic unit and a pump, the motherboard 402 (and optionally the daughterboard 404) can be designed to fit within a single, universal housing. For each upgrade of the product in the product line, additional sensors, controllers, cloud services, etc., can be added. Design, manufacturing, and testing time can be reduced by designing all products in a product line from this base, compared to a product line in which each product has a bespoke logic control system.

Each of the components discussed above can be realized in a wide variety of technologies and configurations. Below, some examples of each component are discussed. Sometimes, two or more components of the system 400 can be realized in a single alternative component; some components can be realized in multiple, separate components; and/or some functionality can be provided by different components.

FIG. 4B is a block diagram showing communication paths of the system 400. As described, the motherboard 402 and daughterboard 404 may act as a hub of the system 400. When the pump daughterboard 404 communicates with cloud services 410 or other components, communications may be routed through the motherboard 402. This may allow the bed to have a single connection with the Internet 412. The computing device 414 may also have a connection to the Internet 412, possibly through the same gateway used by the bed and/or a different gateway (e.g., a cell service provider).

In FIG. 4B, cloud services 410*d* and 410*e* may be configured such that the motherboard 402 communicates with the cloud service directly (e.g., without having to use another cloud service 410 as an intermediary). Additionally or alternatively, some cloud services 410 (e.g., 410*f*) may only be reachable by the motherboard 402 through an intermediary cloud service (e.g., 410*e*). While not shown here, some cloud services 410 may be reachable either directly or indirectly by the pump motherboard 402.

Additionally, some or all of the cloud services 410 may communicate with other cloud services, including the transfer of data and/or remote function calls according to any technologically appropriate format. For example, one cloud service 410 may request a copy for another cloud service's

410 data (e.g., for purposes of backup, coordination, migration, calculations, data mining). Many cloud services 410 may also contain data that is indexed according to specific users tracked by the user account cloud 410*c* and/or the bed data cloud 410*a*. These cloud services 410 may communicate with the user account cloud 410*c* and/or the bed data cloud 410*a* when accessing data specific to a particular user or bed.

Figure 5:
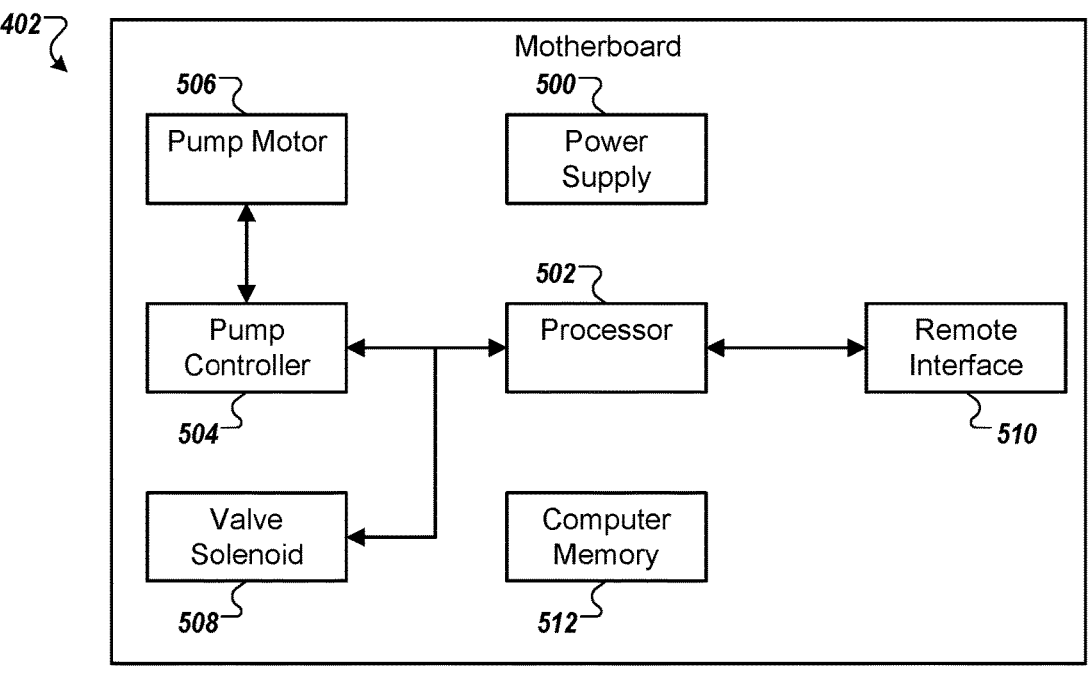
FIGS. 5 and 6 are block diagrams of examples of motherboards that can be used in a data processing system associated with a bed.

FIG. 5 is a block diagram of an example motherboard 402 in a data processing system associated with a bed system (e.g., refer to FIGS. 1-3). In this example, compared to other examples described below, this motherboard 402 consists of relatively fewer parts and can be limited to provide a relatively limited feature set.

The motherboard 402 includes a power supply 500, a processor 502, and computer memory 512. In general, the power supply 500 includes hardware used to receive electrical power from an outside source and supply it to components of the motherboard 402. The power supply may include a battery pack and/or wall outlet adapter, an AC to DC converter, a DC to AC converter, a power conditioner, a capacitor bank, and/or one or more interfaces for providing power in the current type, voltage, etc., needed by other components of the motherboard 402.

The processor 502 is generally a device for receiving input, performing logical determinations, and providing output. The processor 502 can be a central processing unit, a microprocessor, general purpose logic circuitry, application-specific integrated circuitry, a combination of these, and/or other hardware.

The memory 512 is generally one or more devices for storing data, which may include long term stable data storage (e.g., on a hard disk), short term unstable (e.g., on Random Access Memory), or any other technologically appropriate configuration.

The motherboard 402 includes a pump controller 504 and a pump motor 506. The pump controller 504 can receive commands from the processor 502 to control functioning of the pump motor 506. For example, the pump controller 504 can receive a command to increase pressure of an air chamber by 0.3 pounds per square inch (PSI). The pump controller 504, in response, engages a valve so that the pump motor 506 pumps air into the selected air chamber, and can engage the pump motor 506 for a length of time that corresponds to 0.3 PSI or until a sensor indicates that pressure has been increased by 0.3 PSI. Sometimes, the message can specify that the chamber should be inflated to a target PSI, and the pump controller 504 can engage the pump motor 506 until the target PSI is reached.

A valve solenoid 508 can control which air chamber a pump is connected to. In some cases, the solenoid 508 can be controlled by the processor 502 directly. In some cases, the solenoid 508 can be controlled by the pump controller 504.

A remote interface 510 of the motherboard 402 can allow the motherboard 402 to communicate with other components of a data processing system. For example, the motherboard 402 can be able to communicate with one or more daughterboards, with peripheral sensors, and/or with peripheral controllers through the remote interface 510. The remote interface 510 can provide any technologically appropriate communication interface, including but not limited to multiple communication interfaces such as WIFI, Bluetooth, and copper wired networks.

Figure 6:
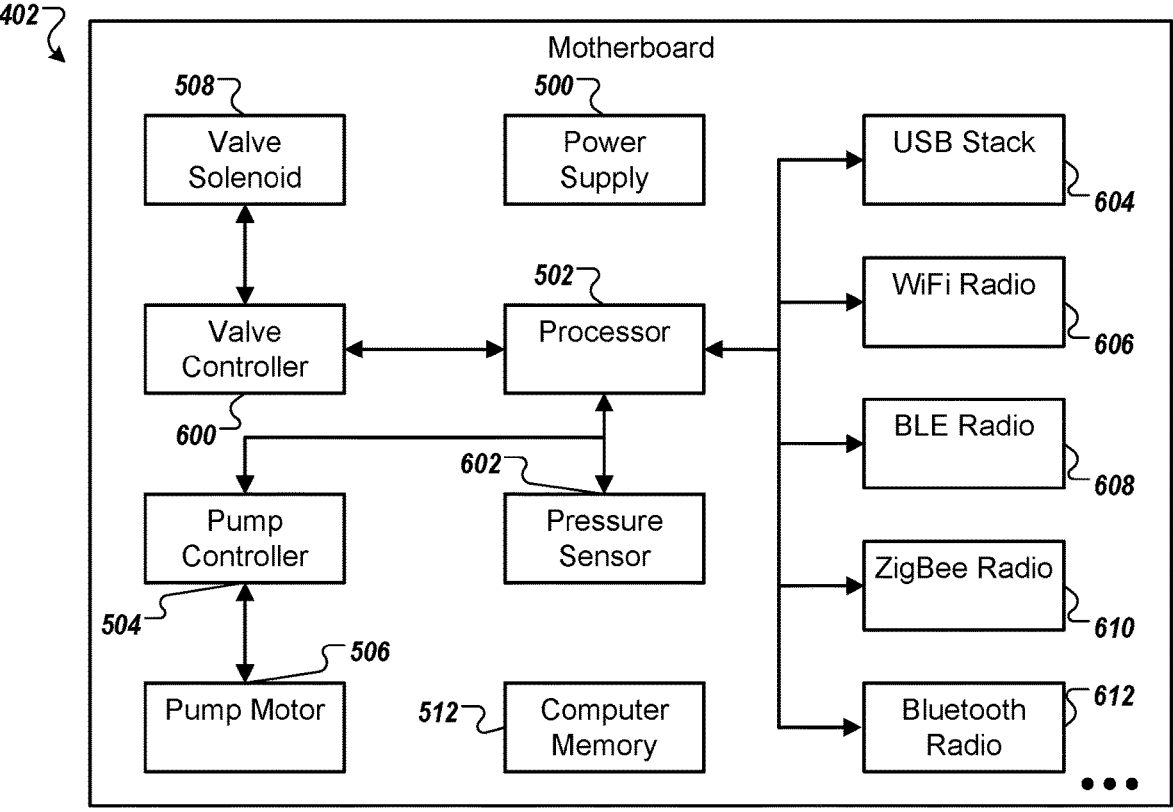

FIG. 6 is a block diagram of another example motherboard 402. Compared to the motherboard 402 in FIG. 5, the motherboard 402 in FIG. 6 can contain more components and provide more functionality in some applications.

This motherboard 402 can further include a valve controller 600, a pressure sensor 602, a universal serial bus (USB) stack 604, a WiFi radio 606, a Bluetooth Low Energy (BLE) radio 608, a ZigBee radio 610, a Bluetooth radio 612, and a computer memory 512.

The valve controller 600 can convert commands from the processor 502 into control signals for the valve solenoid 508. For example, the processor 502 can issue a command to the valve controller 600 to connect the pump to a particular air chamber out of a group of air chambers in an air bed. The valve controller 600 can control the position of the valve solenoid 508 so the pump is connected to the indicated air chamber.

The pressure sensor 602 can read pressure readings from one or more air chambers of the air bed. The pressure sensor 602 can also preform digital sensor conditioning. As described herein, multiple pressure sensors 602 can be included as part of the motherboard 402 or otherwise in communication with the motherboard 402.

The motherboard 402 can include a suite of network interfaces 604, 606, 608, 610, 612, etc., including but not limited to those shown in FIG. 6. These network interfaces can allow the motherboard to communicate over a wired or wireless network with any devices, including but not limited to peripheral sensors, peripheral controllers, computing devices, and devices and services connected to the Internet 412.

Figure 7:
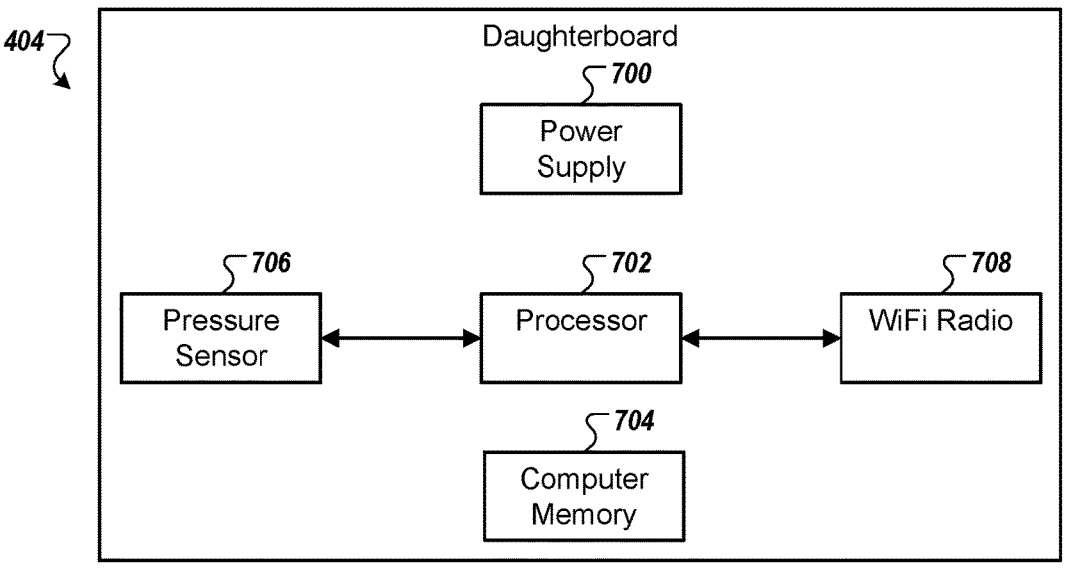
FIG. 7 is a block diagram of an example of a daughterboard that can be used in a data processing system associated with a bed.

FIG. 7 is a block diagram of an example daughterboard 404 used in a data processing system associated with a bed system described herein. One or more daughterboards 404 can be connected to the motherboard 402. Some daughterboards 404 can be designed to offload particular and/or compartmentalized tasks from the motherboard 402. This can be advantageous if the particular tasks are computationally intensive, proprietary, or subject to future revisions. For example, the daughterboard 404 can be used to calculate a particular sleep data metric. This metric can be computationally intensive, and calculating the metric on the daughterboard 404 can free up resources of the motherboard 402 while the metric is calculated. The sleep metric may be subject to future revisions. To update the system 400 with the new metric, it is possible that only the daughterboard 404 calculates the metric to be replaced. In this case, the same motherboard 402 and other components can be used, saving the need to perform unit testing of additional components instead of just the daughterboard 404.

The daughterboard 404 includes a power supply 700, a processor 702, computer readable memory 704, a pressure sensor 706, and a WiFi radio 708. The processor 702 can use the pressure sensor 706 to gather information about pressure of air bed chambers. The processor 702 can perform an algorithm to calculate a sleep metric (e.g., sleep quality, bed presence, whether the user fell asleep, a heartrate, a respiration rate, movement, etc.). Sometimes, the sleep metric can be calculated from only air chamber pressure. The sleep metric can also be calculated using signals from a variety of sensors (e.g., movement, pressure, temperature, and/or audio sensors). The processor 702 can receive that data from sensors that may be internal to the daughterboard 404, accessible via the WiFi radio 708, or otherwise in communication with the processor 702. Once the sleep metric is calculated, the processor 702 can report that sleep metric to, for example, the motherboard 402. The motherboard 402 can generate instructions for outputting the sleep metric to the user or using the sleep metric to determine other user information or controls to control the bed and/or peripheral devices.

Figure 8:
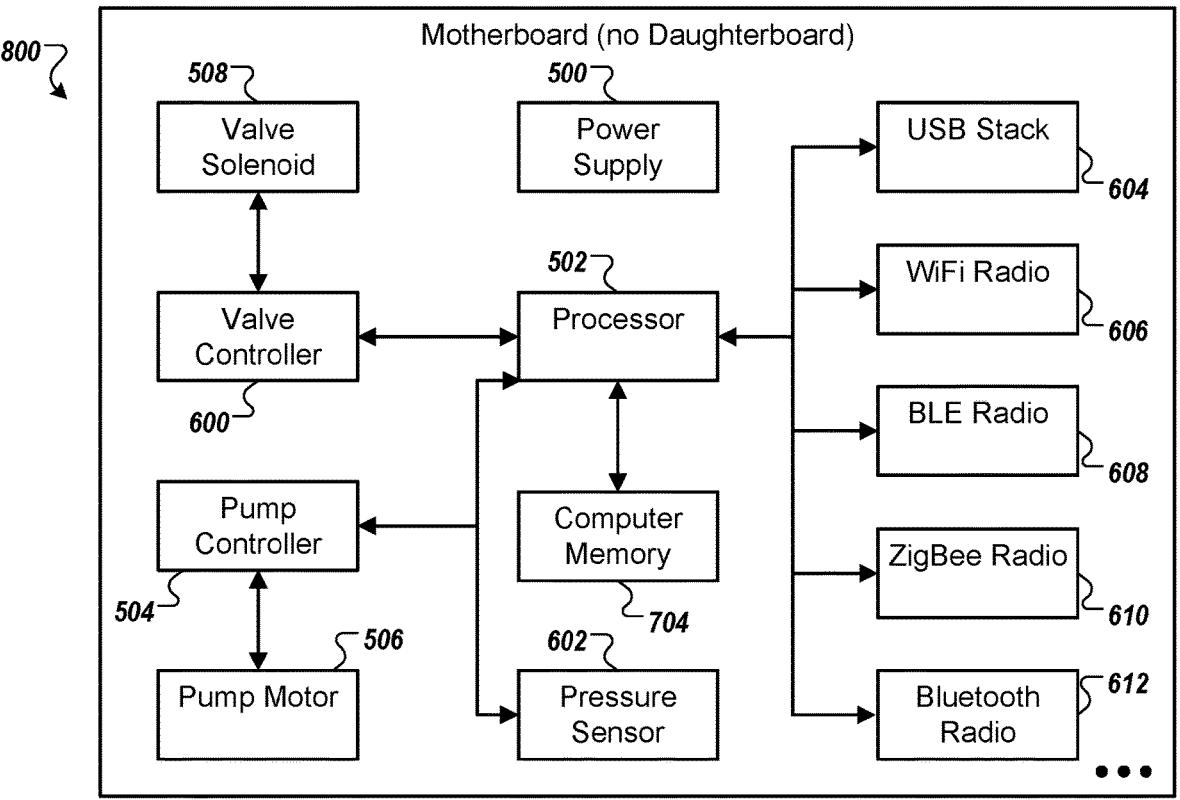
FIG. 8 is a block diagram of an example of a motherboard with no daughterboard that can be used in a data processing system associated with a bed.

FIG. 8 is a block diagram of an example motherboard 800 with no daughterboard used in a data processing system associated with a bed system. In this example, the motherboard 800 can perform most, all, or more of the features described with reference to the motherboard 402 in FIG. 6 and the daughterboard 404 in FIG. 7.

Figure 9A:
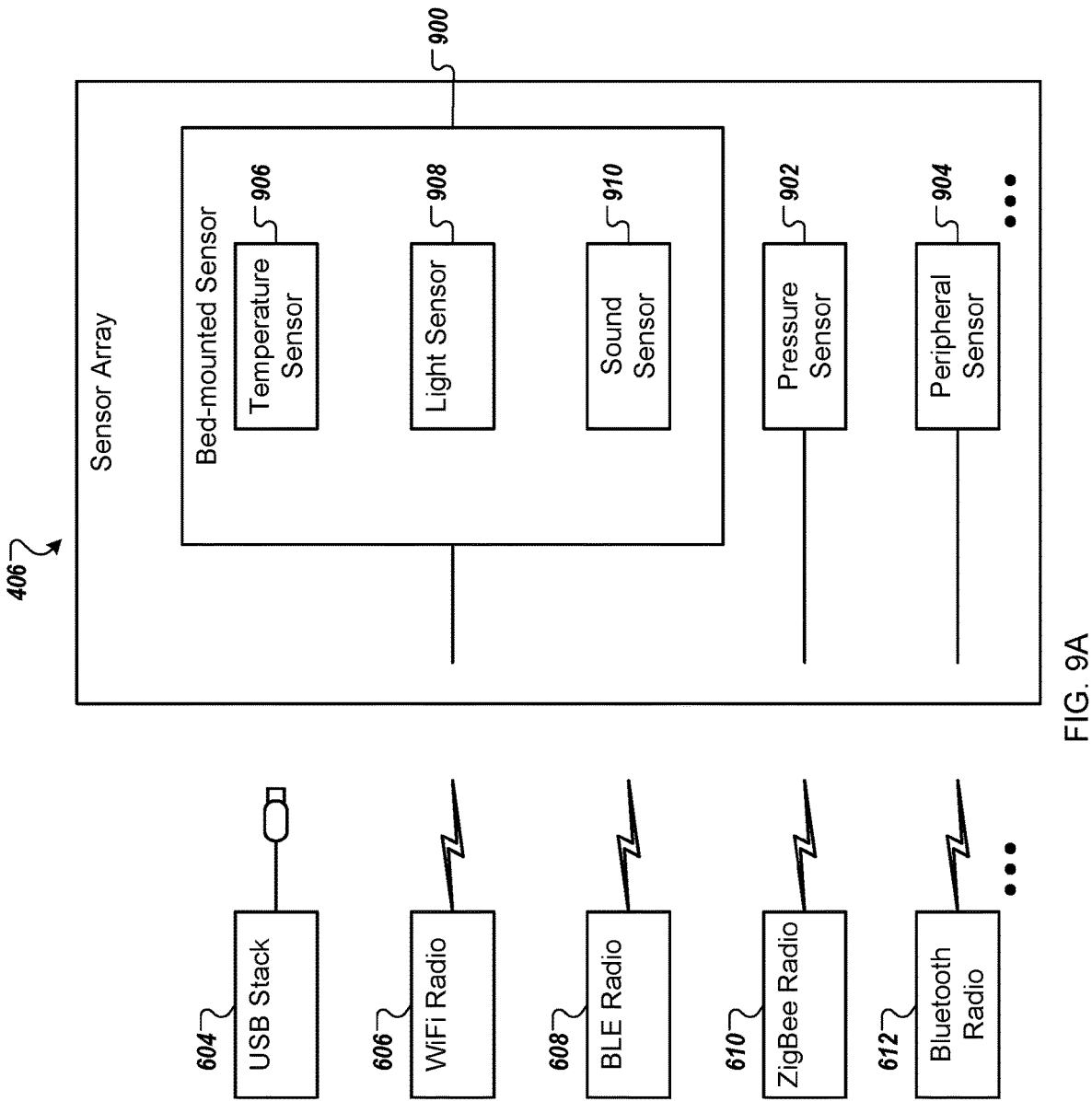
FIG. 9A is a block diagram of an example of a sensory array that can be used in a data processing system associated with a bed.

FIG. 9A is a block diagram of an example sensory array 406 used in a data processing system associated with a bed system described herein. The sensor array 406 is a conceptual grouping of some or all peripheral sensors that communicate with the motherboard 402 but are not native to the motherboard 402. The peripheral sensors 902, 904, 906, 908, 910, etc. of the sensor array 406 communicate with the motherboard 402 through one or more network interfaces 604, 606, 608, 610, and 612 of the motherboard, as is appropriate for the configuration of the particular sensor. For example, a sensor that outputs a reading over a USB cable can communicate through the USB stack 604.

Some peripheral sensors of the sensor array 406 can be bed mounted sensors 900 (e.g., temperature sensor 906, light sensor 908, sound sensor 910). The bed mounted sensors 900 can be embedded into a bed structure and sold with the bed, or later affixed to the structure (e.g., part of a pressure sensing pad that is removably installed on a top surface of the bed, part of a temperature sensing or heating pad that is removably installed on the top surface of the bed, integrated into the top surface, attached along connecting tubes between a pump and air chambers, within air chambers, attached to a headboard, attached to one or more regions of an adjustable foundation). One or more of the sensors 902 can be load cells or force sensors as described in FIG. 9C. Other sensors 902 and 904 may not be mounted to the bed and can include a pressure sensor 902 and/or peripheral sensor 904. For example, the sensors 902 and 904 can be integrated or otherwise part of a user mobile device (e.g., mobile phone, wearable device). The sensors 902 and 904 can also be part of a central controller for controlling the bed and peripheral devices. Sometimes, the sensors 902 and 904 can be part of one or more home automation devices or other peripheral devices. In some implementations, the peripheral sensors 904 can include but are not limited to light-detection-and-ranging (LiDAR), radar, and/or time-of-flight (ToF) sensors. LiDAR sensors can, for example emit light from a laser in order to collect measurements, including but not limited to user movement and/or user biometrics. The light can be emitted from pulsed laser beams with wavelengths in a near-infrared (NIR) range. Radar sensors can use radio waves and/or microwaves and thus operate at longer wavelengths than LiDAR sensors. Radar sensors can similarly be used to detect user movement and/or user biometrics. ToF sensors can be used to determine amounts of time that it takes photons or other energy particles to travel between two points, which can be similarly used to detect user movement and/or user biometrics. One or more other peripheral sensors 904 are also possible.

Sometimes, some or all of the bed mounted sensors 900 and/or sensors 902 and 904 share networking hardware (e.g., a conduit that contains wires from each sensor, a multi-wire cable or plug that, when affixed to the motherboard 402, connect all the associated sensors with the motherboard 402). One, some, or all the sensors 902, 904, 906, 908, and 910 can sense features of a mattress (e.g., pressure, temperature, light, sound, and/or other features) and features external to the mattress. Sometimes, pressure sensor 902 can sense pressure of the mattress while some or all the sensors 902, 904, 906, 908, and 910 sense features of the mattress and/or features external to the mattress.

Figure 9B:
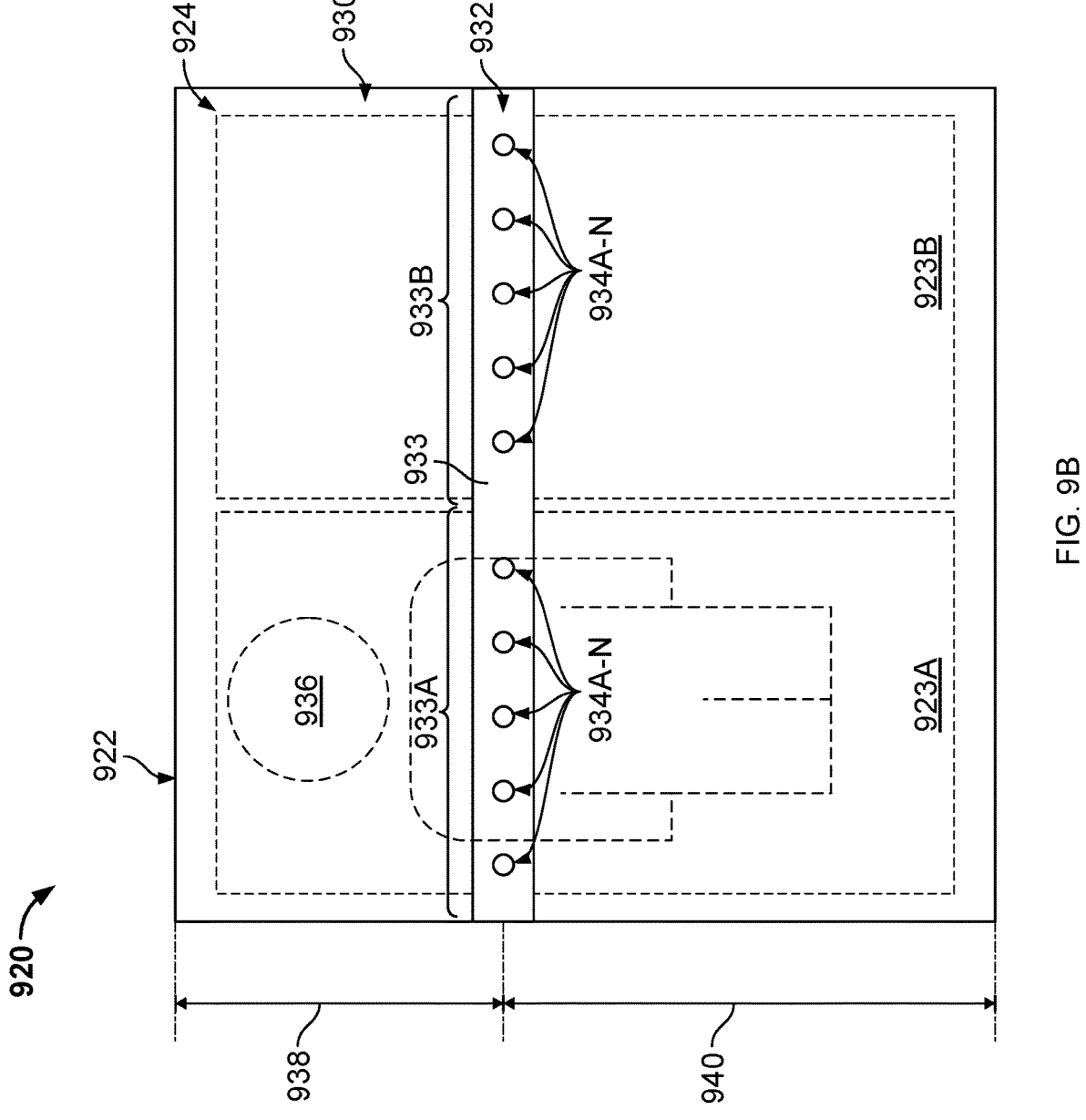
FIG. 9B is a schematic top view of a bed having an example of a sensor strip with one or more sensors that can be used in a data processing system associated with the bed.

FIG. 9B is a schematic top view of a bed 920 having a sensor strip 932 with sensors 934A-N used in a data processing system associated with the bed 920. The bed 920 includes a mattress 922 (e.g., refer to FIG. 1). The mattress 922 can have a foam tub 930 beneath a top of the mattress 922. The foam tub 930 can have air chamber 923A and/or 923B, similar to those described herein.

The sensor strip 932 can be attached across the mattress top 924 from one lateral side to an opposing lateral side (e.g., from left to right). The sensor strip 932 can be attached proximate to a head section of the mattress 922 to measure temperature and/or humidity values around a chest area of a user 936. The sensor strip 932 can also be placed at a center point (e.g., midpoint) of the mattress 922 such that the distances 938 and 940 are equal to each other. The sensor strip 932 can be placed at other locations to capture temperature and/or humidity values at the top of the mattress 922.

The sensors 934A-N can be any one or more of the temperature sensors 906 described in FIG. 9A. The sensor strip 932 can also include a carrier strip 933 having a first strip portion 933A and a second strip portion 933B. The carrier strip 933 can be releasably attached to the foam tub layer 920 and extend between the opposite lateral ends of the foam tub 920. The sensor strip 932 can have first sensors 934A-N and second sensors 934A-N. Each of the first and second sensors 934A-N can have five sensors each. For example, a sensor strip 932 for a king or queen size mattress can have a total of ten sensors. When the user 936 is positioned on top of the mattress 922 over the air chamber 923A, the first sensors 934A-N can measure temperature and/or humidity of the mattress top 924 above the air chamber 923A. Those values can be used to, for example, determine a conditioned airflow to supply to the air chamber 923A. Temperature and/or humidity values measured by the second sensors 934A-N can be used to, for example, determine a conditioned airflow to supply to the air chamber 923B. The bed system 920 can provide for custom airflow to different portions of the mattress 922 based on body temperatures of users and/or temperatures of different portions of the mattress top 924.

Sometimes, two separate sensor strips can be attached to the mattress 922 (e.g., a first sensor strip over the air chamber 923A and a second sensor strip, separate from the first sensor strip, over the air chamber 923B). The first and second sensor strips can be attached to a center of the mattress top 924 via fastening elements, such as adhesive. The sensor strip 932 can also be easily replaced with another sensor strip.

Figure 9C:
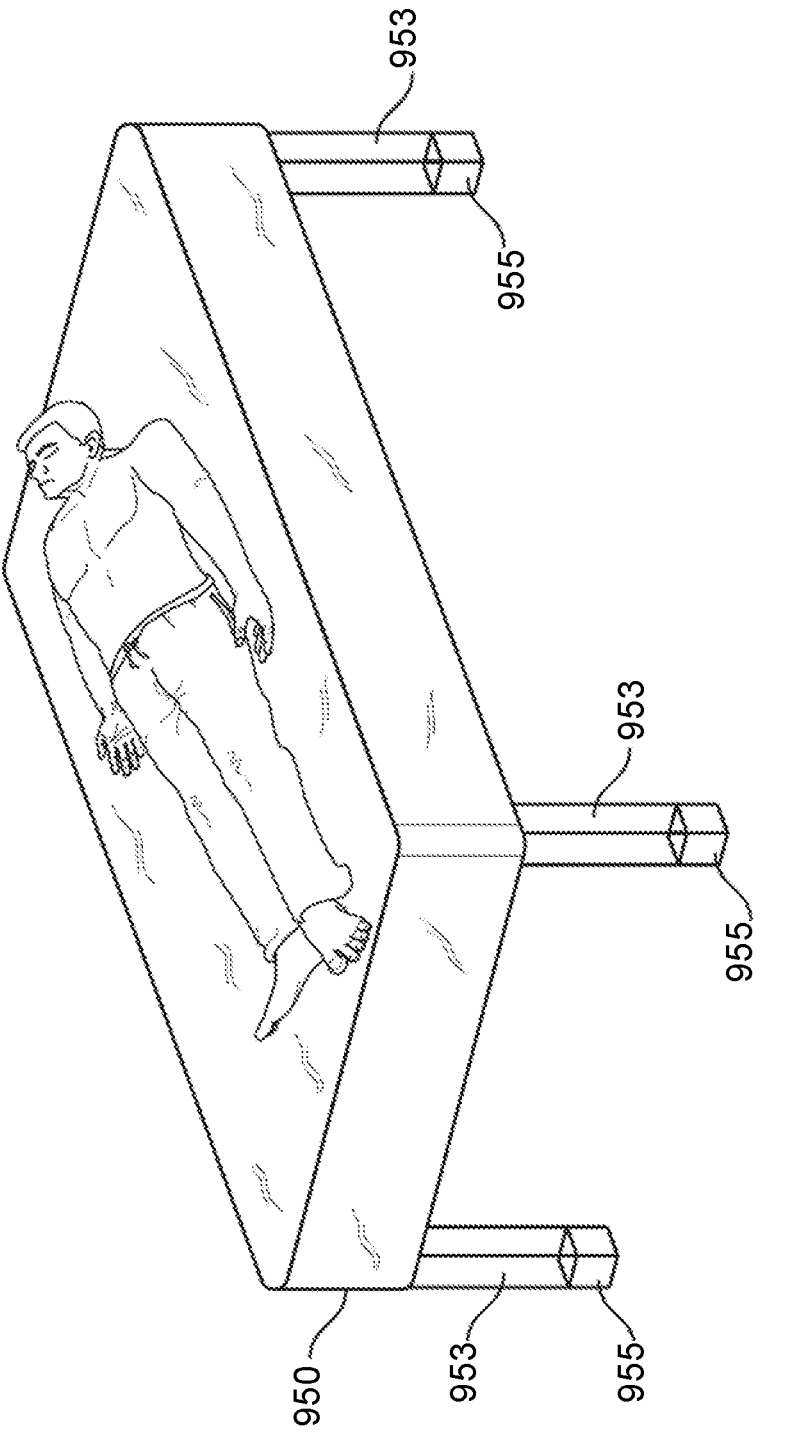
FIG. 9C is a schematic diagram of an example bed with force sensors located at the bottom of legs of the bed.

FIG. 9C is a schematic diagram of an example bed with force sensors 955 located at the bottom of legs 953 of the bed (e.g., in four, six, eight, or another number of legs). The force sensors 955 may also be located elsewhere on the bed with similar effect (e.g., between the legs 953 and platform 950). When a strain gauge is used as the force sensors 955, the force sensor(s) 955 can be positioned nearer centers of the legs 953. The force sensors 955 can be load cells.

Figure 10:
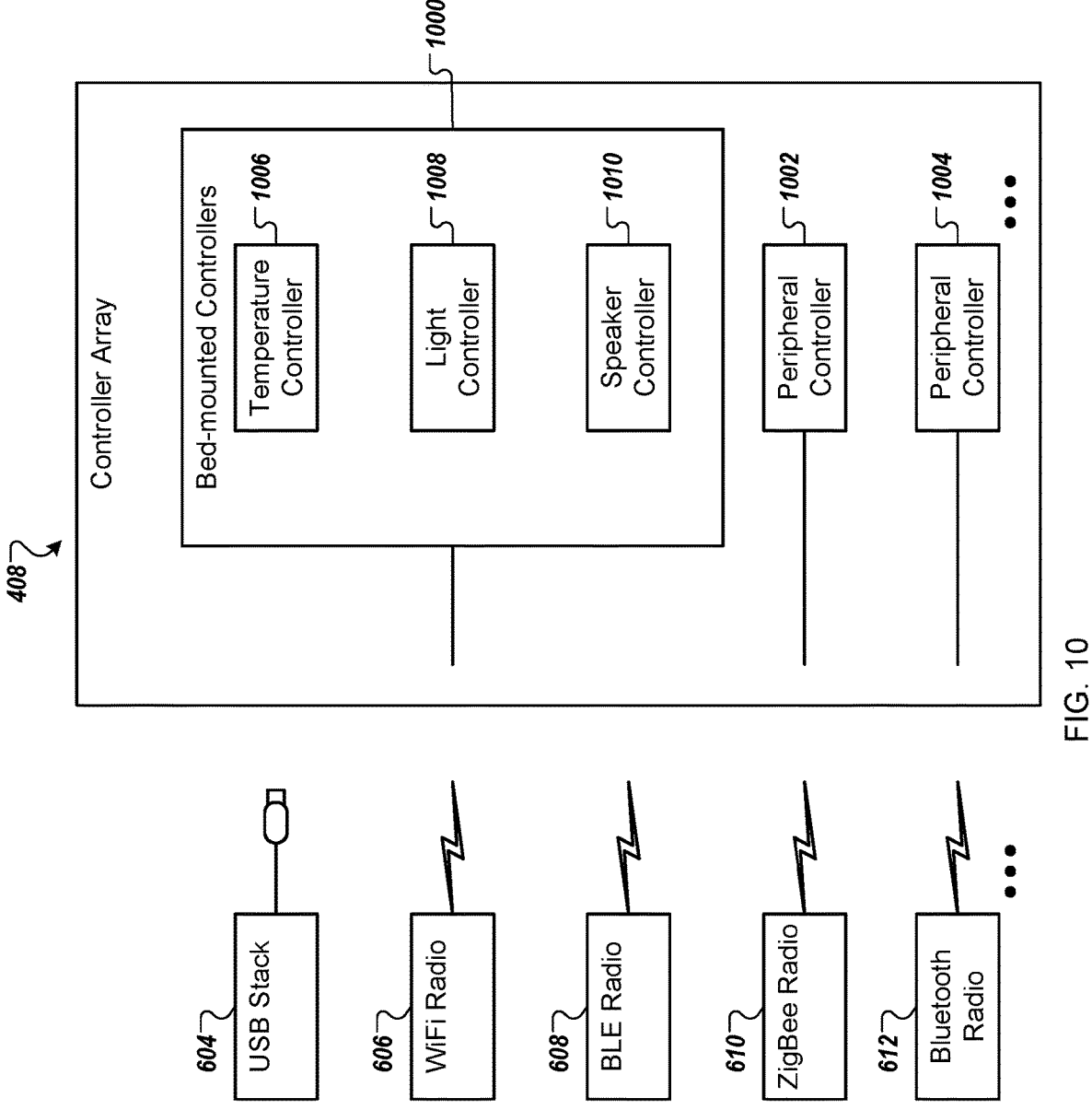
FIG. 10 is a block diagram of an example of a control array that can be used in a data processing system associated with a bed

FIG. 10 is a block diagram of an example controller array 408 used in a data processing system associated with a bed system. The controller array 408 is a conceptual grouping of some or all peripheral controllers that communicate with the motherboard 402 but are not native to the motherboard 402. The peripheral controllers can communicate with the motherboard 402 through one or more of the network interfaces 604, 606, 608, 610, and 612 of the motherboard, as is appropriate for the configuration of the particular controller. Some of the controllers can be bed mounted controllers 1000, such as a temperature controller 1006, a light controller 1008, and a speaker controller 1010, as described in reference to bed-mounted sensors in FIG. 9A. Peripheral controllers 1002 and 1004 can be in communication with the motherboard 402, but optionally not mounted to the bed.

Figure 11:
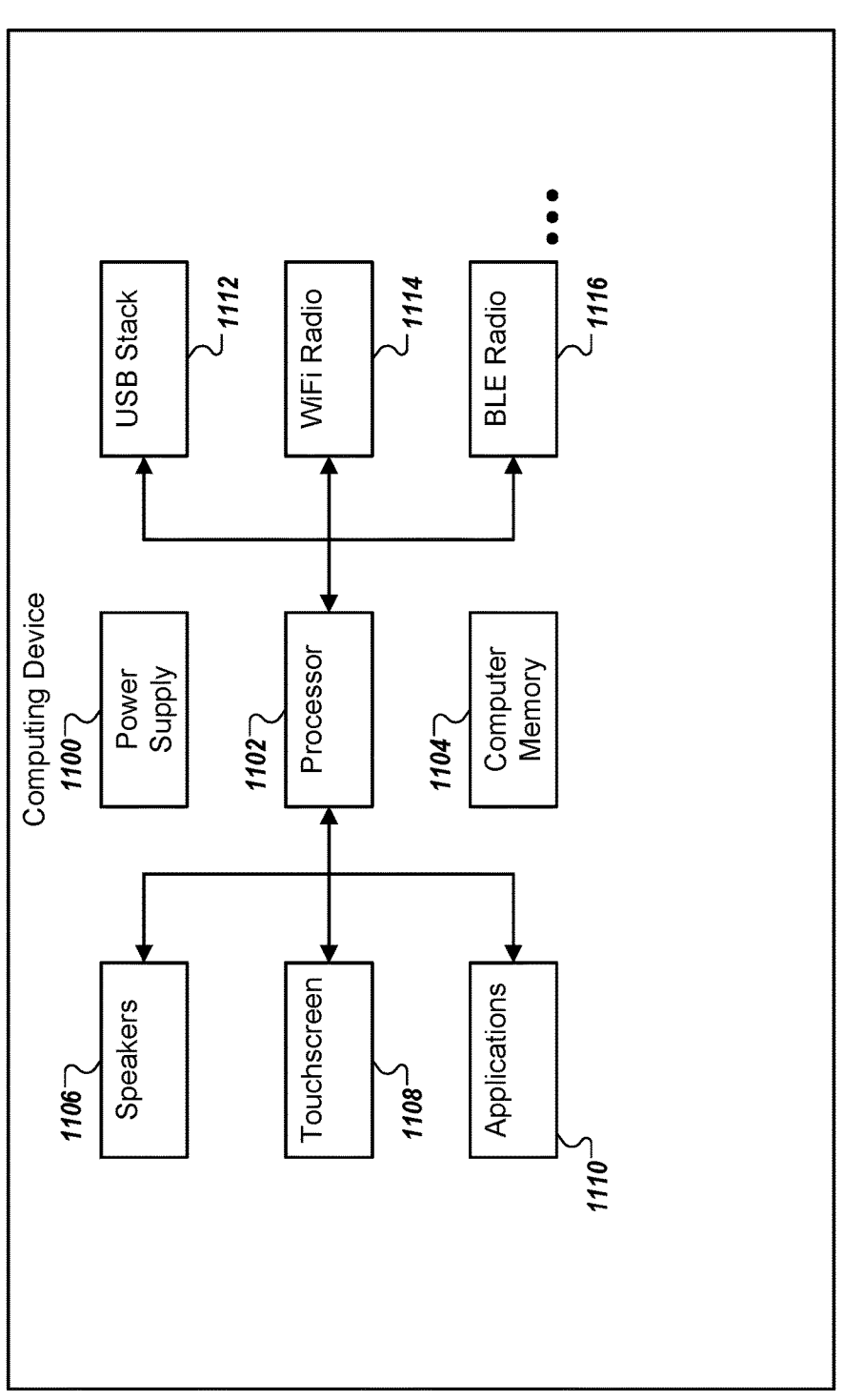
FIG. 11 is a block diagram of an example of a computing device that can be used in a data processing system associated with a bed.

FIG. 11 is a block diagram of an example computing device 412 used in a data processing system associated with a bed system. The computing device 412 can include computing devices used by a user of a bed including but not limited to mobile computing devices (e.g., mobile phones, tablet computers, laptops, smart phones, wearable devices), desktop computers, home automation devices, and/or central controllers or other hub devices.

The computing device 412 includes a power supply 1100, a processor 1102, and computer readable memory 1104. User input and output can be transmitted by speakers 1106, a touchscreen 1108, or other not shown components (e.g., a pointing device or keyboard). The computing device 412 can run applications 1110 including, for example, applications to allow the user to interact with the system 400. These applications can allow a user to view information about the bed (e.g., sensor readings, sleep metrics), information about themselves (e.g., health conditions detected based on signals sensed at the bed), and/or configure the system 400 behavior (e.g., set desired firmness, set desired behavior for peripheral devices). The computing device 412 can be used in addition to, or to replace, the remote control 122 described above.

FIG. 12 is a block diagram of an example bed data cloud service 410a used in a data processing system associated with a bed system. Here, the bed data cloud service 410a is configured to collect sensor data and sleep data from a particular bed, and to match the data with one or more users that used the bed when the data was generated.

The bed data cloud service 410a includes a network interface 1200, a communication manager 1202, server hardware 1204, and server system software 1206. The bed data cloud service 410a is also shown with a user identification module 1208, a device management 1210 module, a sensor data module 1210, and an advanced sleep data module 1214. The network interface 1200 includes hardware and low level software to allow hardware devices (e.g., components of the service 410a) to communicate over networks (e.g., with each other, with other destinations over the Internet 412). The network interface 1200 can include network cards, routers, modems, and other hardware. The communication manager 1202 generally includes hardware and software that operate above the network interface 1200 such as software to initiate, maintain, and tear down network communications used by the service 410a (e.g., TCP/IP, SSL or TLS, Torrent, and other communication sessions over local or wide area networks). The communication manager 1202 can also provide load balancing and other services to other elements of the service 410a. The server hardware 1204 generally includes physical processing devices used to instantiate and maintain the service 410a. This hardware includes, but is not limited to, processors (e.g., central processing units, ASICs, graphical processers) and computer readable memory (e.g., random access memory, stable hard disks, tape backup). One or more servers can be configured into clusters, multi-computer, or datacenters that can be geographically separate or connected. The server system software 1206 generally includes software that runs on the server hardware 1204 to provide operating environments to applications and services (e.g., operating systems running on real servers, virtual machines instantiated on real servers to create many virtual servers, server level operations such as data migration, redundancy, and backup).

The user identification 1208 can include, or reference, data related to users of beds with associated data processing systems. The users may include customers, owners, or other users registered with the service 410a or another service. Each user can have a unique identifier, user credentials, contact information, billing information, demographic information, or any other technologically appropriate information.

The device manager 1210 can include, or reference, data related to beds or other products associated with data processing systems. The beds can include products sold or registered with a system associated with the service 410a. Each bed can have a unique identifier, model and/or serial number, sales information, geographic information, delivery information, a listing of associated sensors and control peripherals, etc. An index or indexes stored by the service 410a can identify users associated with beds. This index can record sales of a bed to a user, users that sleep in a bed, etc.

The sensor data 1212 can record raw or condensed sensor data recorded by beds with associated data processing systems. For example, a bed's data processing system can have temperature, pressure, motion, audio, and/or light sensors. Readings from these sensors, either in raw form or in a format generated from the raw data (e.g. sleep metrics), can be communicated by the bed's data processing system to the service 410a for storage in the sensor data 1212. An index or indexes stored by the service 410a can identify users and/or beds associated with the sensor data 1212.

The service 410a can use any of its available data (e.g., sensor data 1212) to generate advanced sleep data 1214. The advanced sleep data 1214 includes sleep metrics and other data generated from sensor readings (e.g., health information). Some of these calculations can be performed in the service 410a instead of locally on the bed's data processing system because the calculations can be computationally complex or require a large amount of memory space or processor power that may not be available on the bed's data processing system. This can help allow a bed system to operate with a relatively simple controller while being part of a system that performs relatively complex tasks and computations.

For example, the service 410a can retrieve one or more machine learning models from a remote data store and use those models to determine the advanced sleep data 1214. The service 410a can retrieve one or more models to determine overall sleep quality of the user based on currently detected sensor data 1212 and/or historic sensor data. The service 410a can retrieve other models to determine whether the user is snoring based on the detected sensor data 1212. The service 410a can retrieve other models to determine whether the user experiences a health condition based on the data 1212.

FIG. 13 is a block diagram of an example sleep data cloud service 410b used in a data processing system associated with a bed system. Here, the sleep data cloud service 410b is configured to record data related to users' sleep experience. The service 410b includes a network interface 1300, a communication manager 1302, server hardware 1304, and server system software 1306. The service 410b also includes a user identification module 1308, a pressure sensor manager 1310, a pressure based sleep data module 1312, a raw pressure sensor data module 1314, and a non-pressure sleep data module 1316. Sometimes, the service 410b can include a sensor manager for each sensor. The service 410b can also include a sensor manager that relates to multiple sensors in beds (e.g., a single sensor manager can relate to pressure, temperature, light, movement, and audio sensors in a bed).

The pressure sensor manager 1310 can include, or reference, data related to the configuration and operation of pressure sensors in beds. This data can include an identifier of the types of sensors in a particular bed, their settings and calibration data, etc. The pressure based sleep data 1312 can use raw pressure sensor data 1314 to calculate sleep metrics tied to pressure sensor data. For example, user presence, movements, weight change, heartrate, and breathing rate can be determined from raw pressure sensor data 1314. An index or indexes stored by the service 410b can identify users associated with pressure sensors, raw pressure sensor data, and/or pressure based sleep data. The non-pressure sleep data 1316 can use other sources of data to calculate sleep metrics. User-entered preferences, light sensor readings, and sound sensor readings can be used to track sleep data. User presence can also be determined from a combination of raw pressure sensor data 1314 and non-pressure sleep data 1316 (e.g., raw temperature data). Sometimes, bed presence can be determined using only the temperature data. Changes in temperature data can be monitored to determine bed presence or absence in a temporal interval (e.g., window of time) of a given duration. The temperature and/or pressure data can also be combined with other sensing modalities or motion sensors that reflect different forms of movement (e.g., load cells) to accurately detect user presence. For example, the temperature and/or pressure data can be provided as input to a bed presence classifier, which can determine user bed presence based on real-time or near real-time data collected at the bed. The classifier can be trained to differentiate the temperature data from the pressure data, identify peak values in the temperature and pressure data, and generate a bed presence indication based on correlating the peak values. The peak values can be within a threshold distance from each other to then generate an indication that the user is in the bed. An index or indexes stored by the service 410b can identify users associated with sensors and/or the data 1316.

Figure 14:
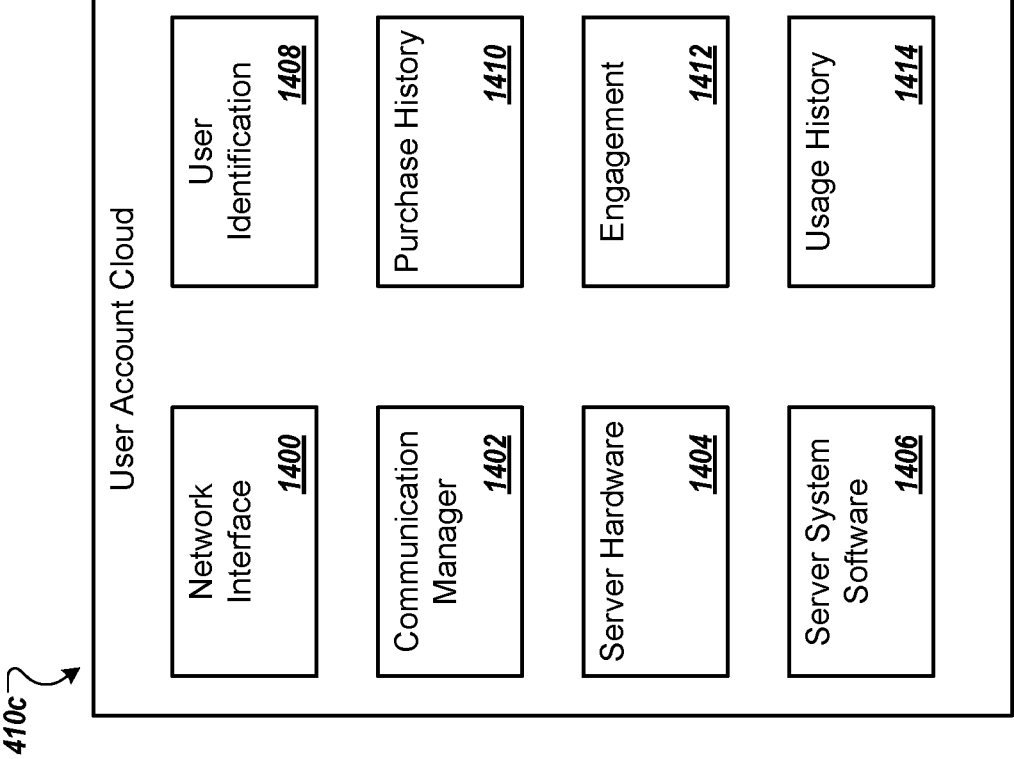

FIG. 14 is a block diagram of an example user account cloud service 410c used in a data processing system associated with a bed system. Here, the service 410c is configured to record a list of users and to identify other data related to those users. The service 410c includes a network interface 1400, a communication manager 1402, server hardware 1404, and server system software 1406. The service 410c also includes a user identification module 1408, a purchase history module 1410, an engagement module 1412, and an application usage history module 1414.

The user identification module 1408 can include, or reference, data related to users of beds with associated data processing systems, as described above. The purchase history module 1410 can include, or reference, data related to purchases by users. The purchase data can include a sale's contact information, billing information, and salesperson information associated with the user's purchase of the bed system. An index or indexes stored by the service 410c can identify users associated with a bed purchase.

The engagement module 1412 can track user interactions with the manufacturer, vendor, and/or manager of the bed/cloud services. This data can include communications (e.g., emails, service calls), data from sales (e.g., sales receipts, configuration logs), and social network interactions. The data can also include servicing, maintenance, or replacements of components of the user's bed system. The usage history module 1414 can contain data about user interactions with applications and/or remote controls of the bed. A monitoring and configuration application can be distributed to run on, for example, computing devices 412 described herein. The application can log and report user interactions for storage in the application usage history module 1414. An index or indexes stored by the service 410c can also identify users associated with each log entry. User interactions stored in the module 1414 can optionally be used to determine or predict user preferences and/or settings for the user's bed and/or peripheral devices that can improve the user's overall sleep quality.

Figure 15:
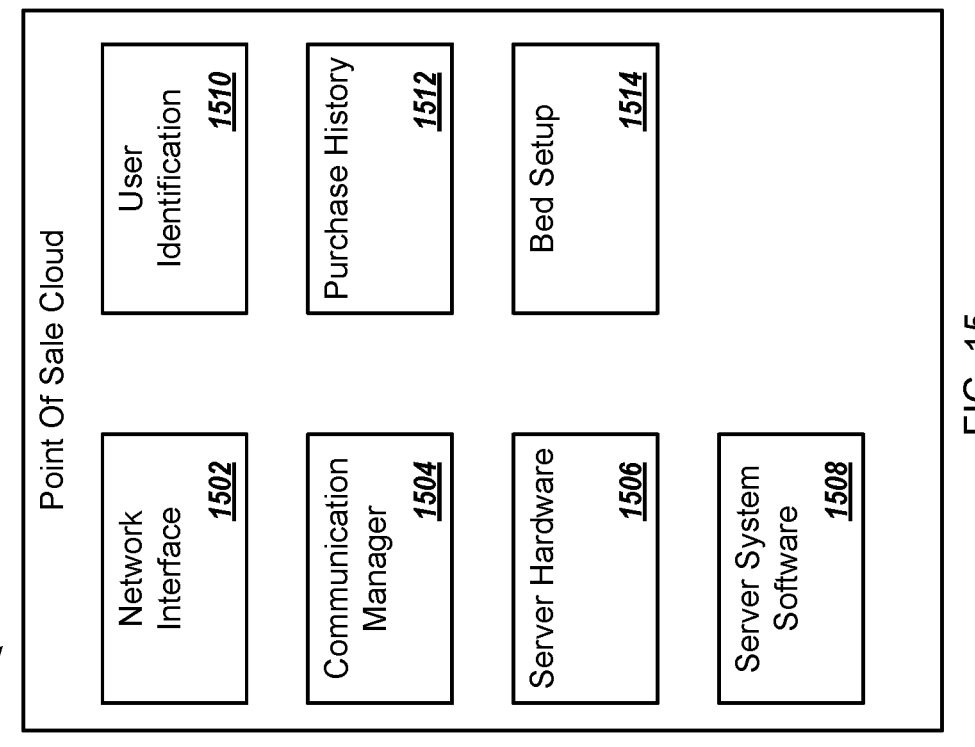

FIG. 15 is a block diagram of an example point of sale cloud service 1500 used in a data processing system associated with a bed system. Here, the service 1500 can record data related to users' purchases, specifically purchases of bed systems described herein. The service 1500 is shown with a network interface 1502, a communication manager 1504, server hardware 1506, and server system software 1508. The service 1500 also includes a user identification module 1510, a purchase history module 1512, and a bed setup module 1514.

The purchase history module 1512 can include, or reference, data related to purchases made by users identified in the module 1510, such as data of a sale, price, and location of sale, delivery address, and configuration options selected by the users at the time of sale. The configuration options can include selections made by the user about how they wish their newly purchased beds to be setup and can include expected sleep schedule, a listing of peripheral sensors and controllers that they have or will install, etc.

The bed setup module 1514 can include, or reference, data related to installations of beds that users purchase. The bed setup data can include a date and address to which a bed is delivered, a person who accepts delivery, configuration that is applied to the bed upon delivery (e.g., firmness settings), name(s) of bed user(s), which side of the bed each user will use, etc. Data recorded in the service 1500 can be referenced by a user's bed system at later times to control functionality of the bed system and/or to send control signals to peripheral components. This can allow a salesperson to collect information from the user at the point of sale that later facilitates bed system automation. Sometimes, some or all aspects of the bed system can be automated with little or no user-entered data required after the point of sale. Sometimes, data recorded in the service 1500 can be used in connection with other, user-entered data.

Figure 16:
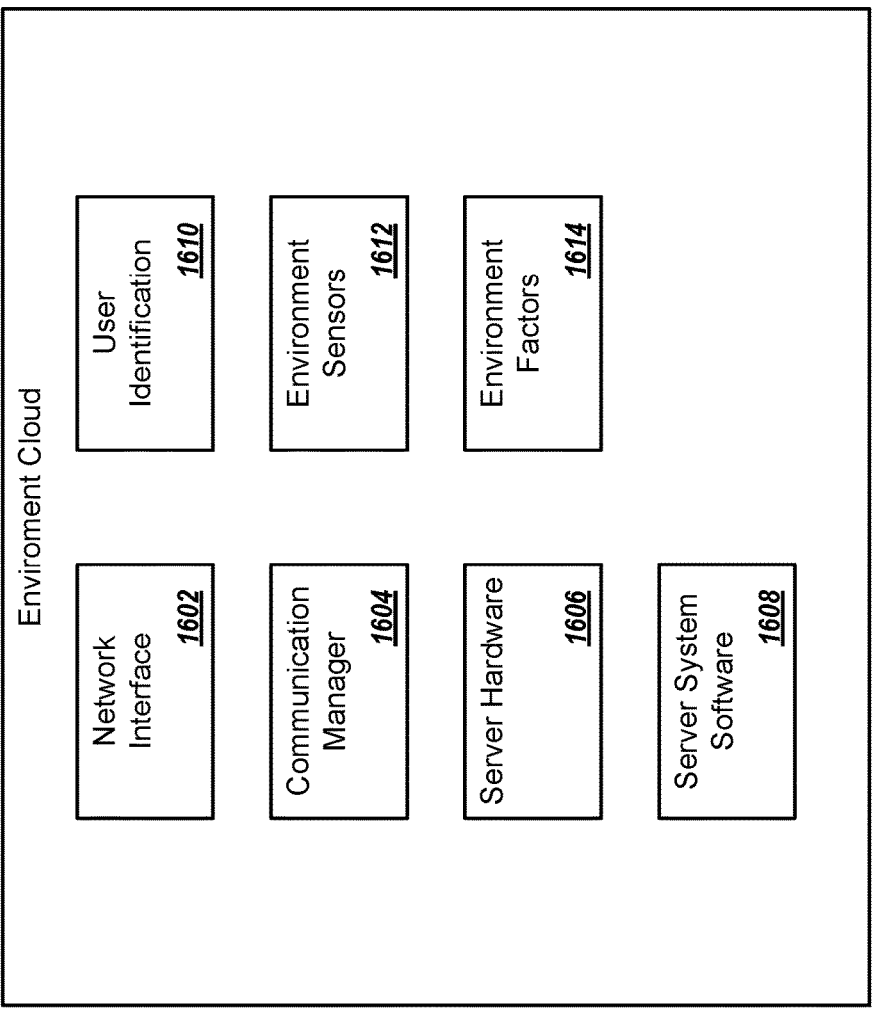

FIG. 16 is a block diagram of an example environment cloud service 1600 used in a data processing system associated with a bed system. Here, the service 1600 is configured to record data related to users' home environment. The service 1600 includes a network interface 1602, a communication manager 1604, server hardware 1606, and server system software 1608. The service 1600 also includes a user identification module 1610, an environmental sensors module 1612, and an environmental factors module 1614. The environmental sensors module 1612 can include a listing and identification of sensors that users identified in the module 1610 to have installed in and/or surrounding their bed (e.g., light, noise/audio, vibration, thermostats, movement/motion sensors). The module 1612 can also store historical readings or reports from the environmental sensors. The module 1612 can be accessed at a later time and used by one or more cloud services described herein to determine sleep quality and/or health information of the users. The environmental factors module 1614 can include reports generated based on data in the module 1612. For example, the module 1614 can generate and retain a report indicating frequency and duration of instances of increased lighting when the user is asleep based on light sensor data that is stored in the environment sensors module 1612.

In the examples discussed here, each cloud service 410 is shown with some of the same components. These same components can be partially or wholly shared between services, or they can be separate. Sometimes, each service can have separate copies of some or all the components that are the same or different in some ways. These components are provided as illustrative examples. In other examples, each cloud service can have different number, types, and styles of components that are technically possible.

Figure 17:
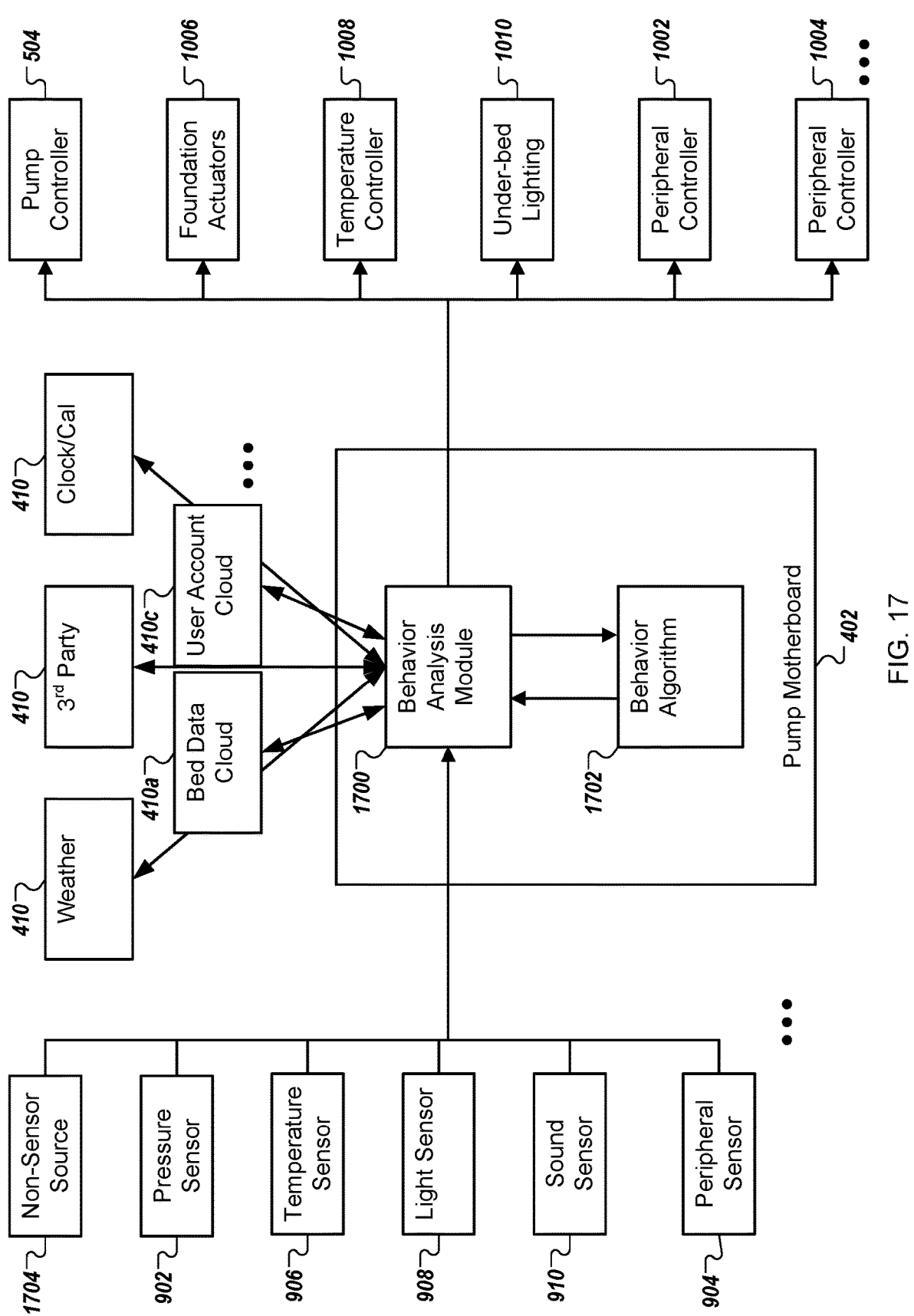
FIG. 17 is a block diagram of an example of using a data processing system that can be associated with a bed to automate peripherals around the bed.

FIG. 17 is a block diagram of an example of using a data processing system associated with a bed to automate peripherals around the bed. Shown here is a behavior analysis module 1700 that runs on the motherboard 402. The behavior analysis module 1700 can be one or more software components stored on the computer memory 512 and executed by the processor 502. In general, the module 1700 can collect data from a variety of sources (e.g., sensors 902, 904, 906, 908, and/or 910, non-sensor local sources 1704, cloud data services 410a and/or 410c) and use a behavioral algorithm 1702 (e.g., machine learning model(s)) to generate actions to be taken (e.g., commands to send to peripheral controllers, data to send to cloud services, such as the bed data cloud 410a and/or the user account cloud 410c). This can be useful, for example, in tracking user behavior and automating devices in communication with the user's bed.

The module 1700 can collect data from any technologically appropriate source (e.g., sensors of the sensor array 406) to gather data about features of a bed, the bed's environment, and/or the bed's users. The data can provide the module 1700 with information about a current state of the bed's environment. For example, the module 1700 can access readings from the pressure sensor 902 to determine air chamber pressure in the bed. From this reading, and potentially other data, user presence can be determined. In another example, the module 1700 can access the light sensor 908 to detect the amount of light in the environment. The module 1700 can also access the temperature sensor 906 to detect a temperature in the environment and/or microclimates in the bed. Using this data, the module 1700 can determine whether temperature adjustments should be made to the environment and/or components of the bed to improve the user's sleep quality and overall comfortability. Similarly, the module 1700 can access data from cloud services to make more accurate determinations of user sleep quality, health information, and/or control the bed and/or peripheral devices. For example, the behavior analysis module 1700 can access the bed cloud service 410a to access historical sensor data 1212 and/or advanced sleep data 1214. The module 1700 can also access a weather reporting service, a $3^{rd}$ party data provider (e.g., traffic and news data, emergency broadcast data, user travel data), and/or a clock and calendar service. Using data retrieved from the cloud services 410, the module 1700 can accurately determine user sleep quality, health information, and/or control of the bed and/or peripheral devices. Similarly, the module 1700 can access data from non-sensor sources 1704, such as a local clock and calendar service (e.g., a component of the motherboard 402 or of the processor 502). The module 1700 can use this information to determine, for example, times of day that the user is in bed, asleep, waking up, and/or going to bed.

The behavior analysis module 1700 can aggregate and prepare this data for use with one or more behavioral algorithms 1702 (e.g., machine learning models). The behavioral algorithms 1702 can be used to learn a user's behavior and/or to perform some action based on the state of the accessed data and/or the predicted user behavior. For example, the behavior algorithm 1702 can use available data (e.g., pressure sensor, non-sensor data, clock and calendar data) to create a model of when a user goes to bed every night. Later, the same or a different behavioral algorithm 1702 can be used to determine if an increase in air chamber pressure is likely to indicate a user going to bed and, if so, send some data to a third-party cloud service 410 and/or engage a peripheral controller 1002 or 1004, foundation actuators 1006, a temperature controller 1008, and/or an under-bed lighting controller 1010.

Here, the module 1700 and the behavioral algorithm 1702 are shown as components of the motherboard 402. Other configurations are also possible. For example, the same or a similar behavioral analysis module 1700 and/or behavioral algorithm 1702 can be run in one or more cloud services, and resulting output can be sent to the pump motherboard 402, a controller in the controller array 408, or to any other technologically appropriate recipient described throughout this document.

Figure 18:
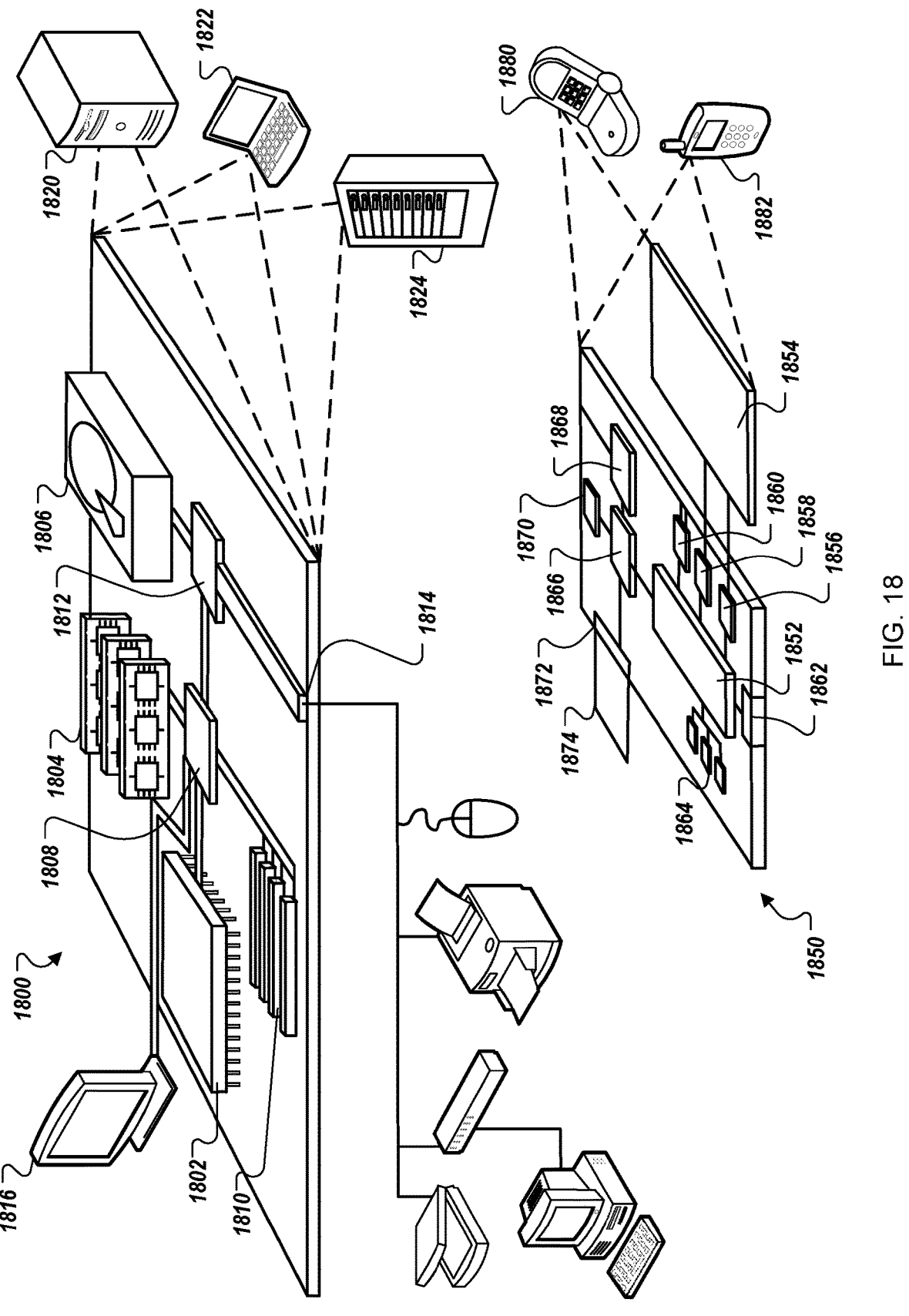
FIG. 18 is a schematic diagram that shows an example of a computing device and a mobile computing device.

FIG. 18 shows an example of a computing device 1800 and an example of a mobile computing device that can be used to implement the techniques described here. The computing device 1800 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 1800 includes a processor 1802, a memory 1804, a storage device 1806, a high-speed interface 1808 connecting to the memory 1804 and multiple high-speed expansion ports 1810, and a low-speed interface 1812 connecting to a low-speed expansion port 1814 and the storage device 1806. Each of the processor 1802, the memory 1804, the storage device 1806, the high-speed interface 1808, the high-speed expansion ports 1810, and the low-speed interface 1812, are interconnected using various busses, and can be mounted on a common motherboard or in other manners as appropriate. The processor 1802 can process instructions for execution within the computing device 1800, including instructions stored in the memory 1804 or on the storage device 1806 to display graphical information for a GUI on an external input/output device, such as a display 1816 coupled to the high-speed interface 1808. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system). The memory 1804 stores information within the computing device 1800. In some implementations, the memory 1804 is a volatile memory unit or units. In some implementations, the memory 1804 is a non-volatile memory unit or units. The memory 1804 can also be another form of computer-readable medium, such as a magnetic or optical disk. The storage device 1806 is capable of providing mass storage for the computing device 1800. In some implementations, the storage device 1806 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 1804, the storage device 1806, or memory on the processor 1802.

The high-speed interface 1808 manages bandwidth-intensive operations for the computing device 1800, while the low-speed interface 1812 manages lower bandwidth-intensive operations. Such allocation of functions is exemplary only. In some implementations, the high-speed interface 1808 is coupled to the memory 1804, the display 1816 (e.g., through a graphics processor or accelerator), and to the high-speed expansion ports 1810, which can accept various expansion cards (not shown). In the implementation, the low-speed interface 1812 is coupled to the storage device 1806 and the low-speed expansion port 1814. The low-speed expansion port 1814, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter. The computing device 1800 can be implemented in a number of different forms, as shown in the figure. For example, it can be implemented as a standard server 1820, or multiple times in a group of such servers. In addition, it can be implemented in a personal computer such as a laptop computer 1822. It can also be implemented as part of a rack server system 1824. Alternatively, components from the computing device 1800 can be combined with other components in a mobile device (not shown), such as a mobile computing device 1850. Each of such devices can contain one or more of the computing device 1800 and the mobile computing device 1850, and an entire system can be made up of multiple computing devices communicating with each other. The mobile computing device 1850 includes a processor 1852, a memory 1864, an input/output device such as a display 1854, a communication interface 1866, and a transceiver 1868, among other components. The mobile computing device 1850 can also be provided with a storage device, such as a micro-drive or other device, to provide additional storage. Each of the processor 1852, the memory 1864, the display 1854, the communication interface 1866, and the transceiver 1868, are interconnected using various buses, and several of the components can be mounted on a common motherboard or in other manners as appropriate.

The processor 1852 can execute instructions within the mobile computing device 1850, including instructions stored in the memory 1864. The processor 1852 can be implemented as a chipset of chips that include separate and multiple analog and digital processors. The processor 1852 can provide, for example, for coordination of the other components of the mobile computing device 1850, such as control of user interfaces, applications run by the mobile computing device 1850, and wireless communication by the mobile computing device 1850. The processor 1852 can communicate with a user through a control interface 1858 and a display interface 1856 coupled to the display 1854. The display 1854 can be, for example, a TFT (Thin-Film-Transistor Liquid Crystal Display) display or an OLED (Organic Light Emitting Diode) display, or other appropriate display technology. The display interface 1856 can comprise appropriate circuitry for driving the display 1854 to present graphical and other information to a user. The control interface 1858 can receive commands from a user and convert them for submission to the processor 1852. In addition, an external interface 1862 can provide communication with the processor 1852, so as to enable near area communication of the mobile computing device 1850 with other devices. The external interface 1862 can provide, for example, for wired communication in some implementations, or for wireless communication in other implementations, and multiple interfaces can also be used.

The memory 1864 stores information within the mobile computing device 1850. The memory 1864 can be implemented as one or more of a computer-readable medium or media, a volatile memory unit or units, or a non-volatile memory unit or units. An expansion memory 1874 can also be provided and connected to the mobile computing device 1850 through an expansion interface 1872, which can include, for example, a SIMM (Single In Line Memory Module) card interface. The expansion memory 1874 can provide extra storage space for the mobile computing device 1850, or can also store applications or other information for the mobile computing device 1850. Specifically, the expansion memory 1874 can include instructions to carry out or supplement the processes described above, and can include secure information also. Thus, for example, the expansion memory 1874 can be provide as a security module for the mobile computing device 1850, and can be programmed with instructions that permit secure use of the mobile computing device 1850. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 1864, the expansion memory 1874, or memory on the processor 1852. In some implementations, the computer program product can be received in a propagated signal, for example, over the transceiver 1868 or the external interface 1862.

The mobile computing device 1850 can communicate wirelessly through the communication interface 1866, which can include digital signal processing circuitry where necessary. The communication interface 1866 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 1868 using a radio-frequency. In addition, short-range communication can occur, such as using a Bluetooth, WiFi, or other such transceiver (not shown). In addition, a GPS (Global Positioning System) receiver module 1870 can provide additional navigation- and location-related wireless data to the mobile computing device 1850, which can be used as appropriate by applications running on the mobile computing device 1850. The mobile computing device 1850 can also communicate audibly using an audio codec 1860, which can receive spoken information from a user and convert it to usable digital information. The audio codec 1860 can likewise generate audible sound for a user, such as through a speaker, e.g., in a handset of the mobile computing device 1850. Such sound can include sound from voice telephone calls, can include recorded sound (e.g., voice messages, music files, etc.) and can also include sound generated by applications operating on the mobile computing device 1850. The mobile computing device 1850 can be implemented in a number of different forms, as shown in the figure. For example, it can be implemented as a cellular telephone 1880. It can also be implemented as part of a smart-phone 1882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input. The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet. The computing system can include clients and servers. A client and server are generally remote from each other and typically interact through a communication network. The relationship of client and server arises by virtue of computer programs running on the respective computers and having a client-server relationship to each other.

Figure 19:
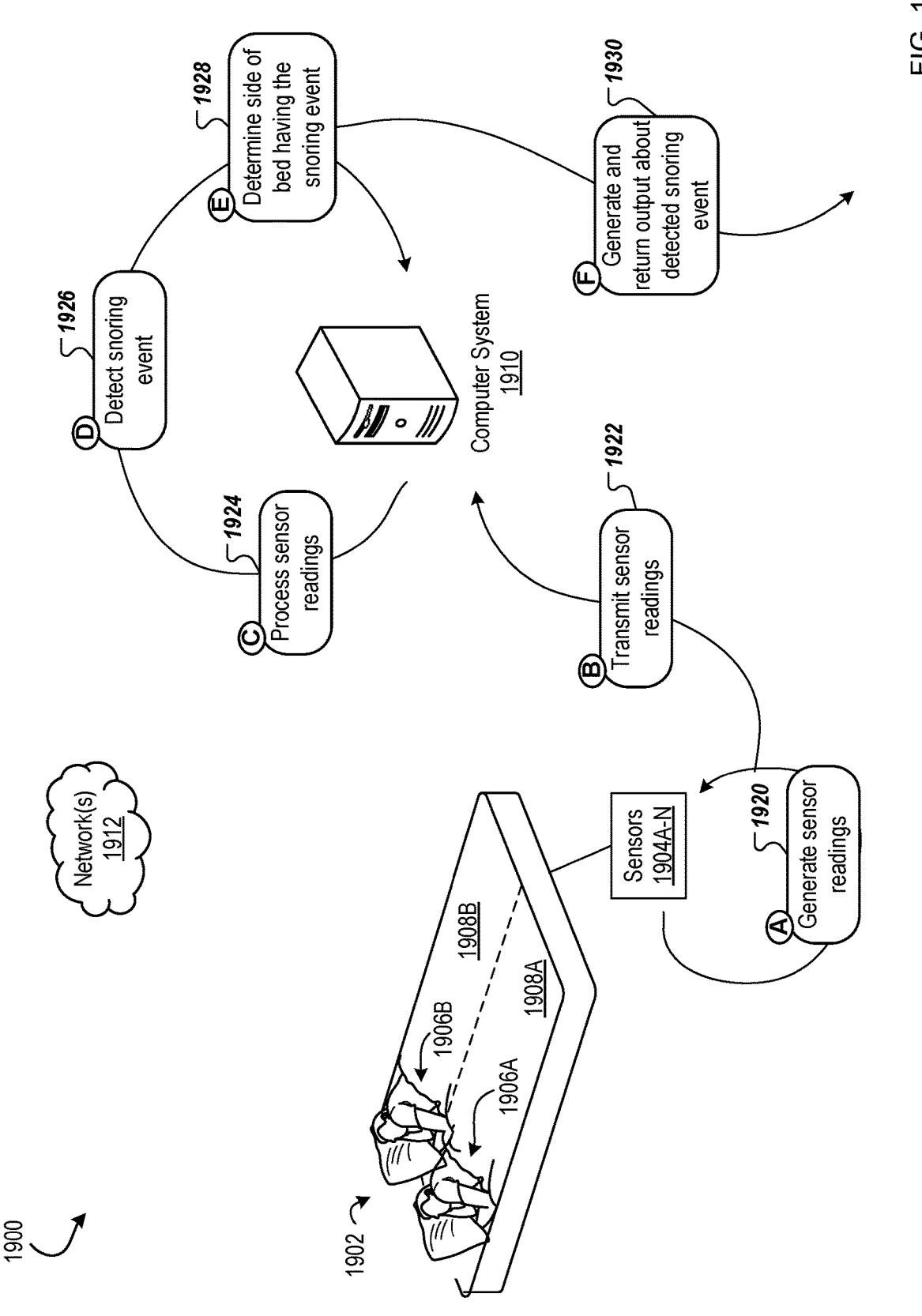
FIG. 19 is a conceptual diagram of a system for detecting snorer side at a bed system.

FIG. 19 is a conceptual diagram of a system 1900 for detecting snorer side at a bed system 1902. The bed system 1902 can be similar to any of the bed systems described above. The bed system 1902 can include a mattress, two mattresses supported by a single frame, or two mattresses supported by adjacent and synchronized frames. The bed system 1902 is configured to support first and second sleepers 1906A and 1906B, respectively. The bed system 1902 can include a first side 1908A to support the first sleeper 1906A and a second side 1908B to support the second sleeper 1906B. The bed system 1902 can also include one or more sensors 1904A-N. The sensors 1904A-N can include any variety and/or quantity of sensors described above. For example, at least one first pressure sensor can be proximate the first side 1908A of the bed system 1902 and configured to sense pressure applied to the first side 1908A by the first sleeper 1906A (e.g., the first pressure sensor can be integrated into a first side of a mattress as described above). At least one second pressure sensor can be positioned proximate the second side 1908B of the bed system 1902 and configured to sense pressure applied to the second side 1908B by the second sleeper 1906B (e.g., the second pressure sensor can be integrated into a second side of a mattress as described above). The sensors 1904A-N can include at least one first acoustic sensor proximate the first side 1908A and configured to sense acoustics from the first sleeper 1906A on the first side 1908A. The sensors can include at least one second acoustic sensor proximate the second side 1908B and configured to sense acoustics from the second sleeper 1906B on the second side 1908B.

In some implementations, the bed system 1902 can include a foundation or frame as described above. The first acoustic sensor can be integrated into a first side of the foundation and the second acoustic sensor can be integrated into a second side of the foundation. The second side of the foundation can be opposite the first side and the first side can be configured to support the first sleeper 1906A while the second side can be configured to support the second sleeper 1906B. In some configurations, the bed system can include two adjacent foundations, with each foundation supporting a mattress configured to support one of the sleepers 190A-B, respectively, with each of the two adjacent foundations having an acoustic sensor integrated therein. Sometimes, the first and second acoustic sensors can be integrated into at least one device that is positioned near the bed system 1902. The at least one device can include at least one of a mobile phone, smartphone, wearable device, laptop, tablet, or home automation device (e.g., a smartphone of at least one of the first and second sleepers 1906A and 1906B).

Any other combination and/or quantity of sensors 1904A-N can also be positioned throughout the bed system 1902 and/or on each of the first and second sides 1908A and 1908B of the bed system 1902.

The sensors 1904A-N of the bed system 1902 can communicate over network(s) 1912 (e.g., wired, wireless) with a computer system 1910. The computer system 1910 can be configured to determine a snorer side of the bed system 1902 in real-time and/or near real-time (e.g., while the sleepers 1906A and 1906B are in the bed system 1902). The computer system 1910 can be any type of computing system, computing device, edge computing device, network of devices/systems, and/or cloud-based system. The computer system 1910 can be remote from the bed system 1902. The computer system 1910 can be in communication with sensors from many bed systems. In some implementations, the computer system 1910 can be a controller of the bed system 1902.

Referring to the system 1900 in FIG. 19, the sensors 1904A-N can generate sensor readings in block A (1920). The sensor readings can include acoustic readings and/or pressure readings. The sensor readings can be continuously generated. The sensor readings can be generated at predetermined time intervals (e.g., every 5 seconds, 30 seconds, 1 minute, 5 minutes). The sensor readings can be generated so long as bed presence is detected (e.g., by the computer system 1910 and/or by a controller of the bed system 1902) by at least one of the sleepers 1906A and 1906B (e.g., one of the sleepers enters the bed, one of the sleepers moves less than a threshold amount, one of the sleepers falls asleep). The sensor readings can be generated until bed presence is no longer detected by at least one of the sleepers 1906A and 1906B (e.g., one of the sleepers exits the bed, one of the sleepers moves at least a threshold amount, one of the sleepers wakes up).

The sensors 1904A-N can transmit the sensor readings to the computer system 1910 (block B, 1922). The sensor readings can be transmitted in real-time or near real-time as they are generated by the sensors 1904A-N. The sensor readings can be transmitted in batches at predetermined time intervals. As an illustrative example, the computer system 1910 can receive, from the at least one pressure sensor, pressure readings indicative of the sensed pressure at the bed system 1902. The computer system 1910 can additionally or alternatively receive, from the at least one acoustic sensor, acoustic readings indicative of the sensed acoustics from at least one of the first or second sleepers 1906A and 1906B.

Figure 23:
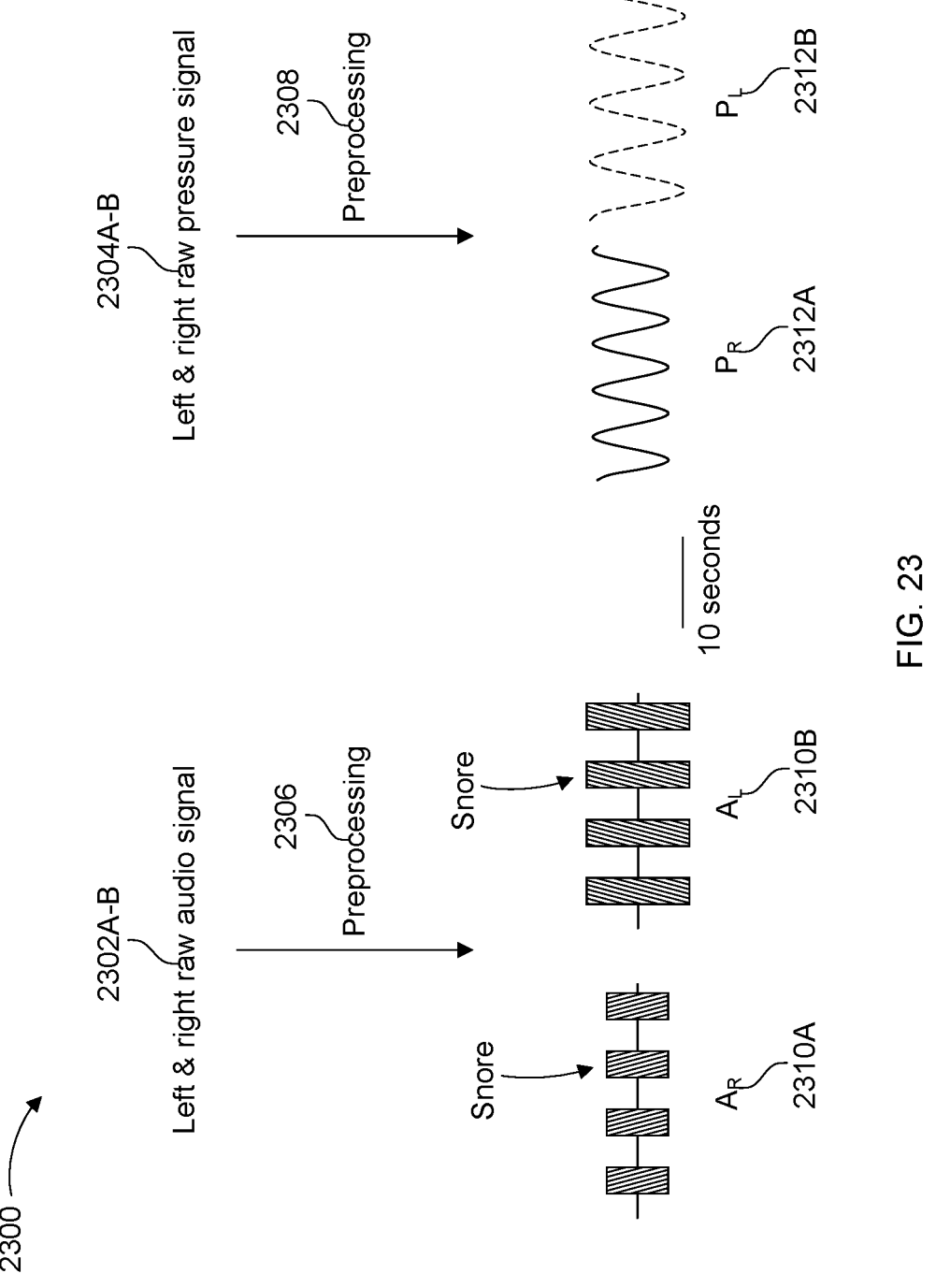
FIG. 23 illustrates an example process for processing acoustic and pressure readings that are received from acoustic and pressure readings at a bed system described herein.

The computer system 1910 can process the received sensor readings in block C (1924). Refer to FIG. 23 for further discussion about processing the sensor readings. For example, processing the received sensor readings can include providing, as input to a machine learning-trained model, at least one of the pressure readings or the acoustic readings. Processing the received sensor readings can also include receiving, as output from the model, the detected snoring event. Sometimes, the model can also be used to determine a snorer side at the bed system 1902, as described below.

In block D (1926), the computer system 1910 can detect a snoring event at the bed system 1902 using the processed sensor readings. Refer to the disclosure herein for detecting the snoring event.

Figure 20A:
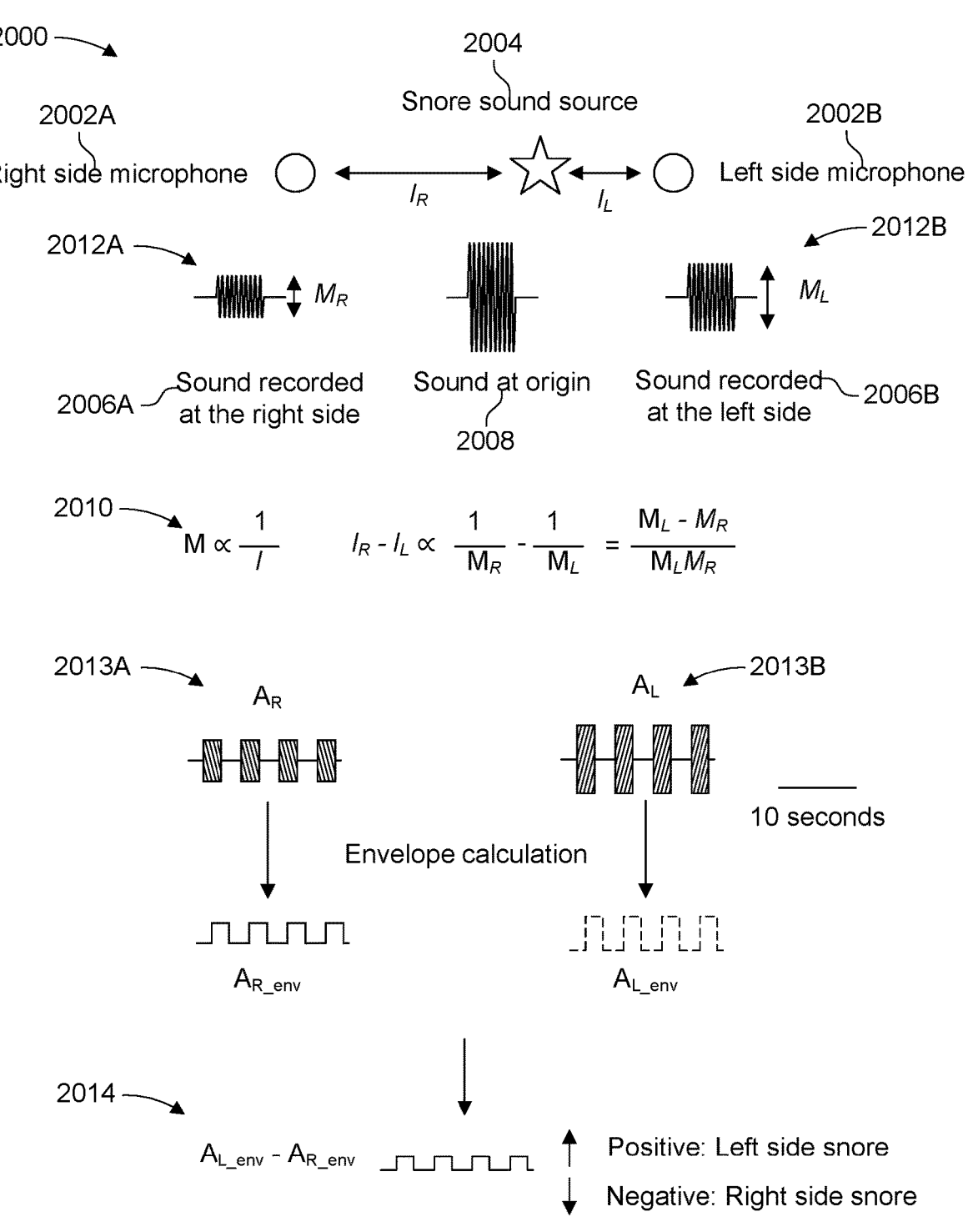
FIGS. 20A-B illustrate an example process for detecting snorer side based on assessing amplitude of acoustic readings.
Figure 20B:
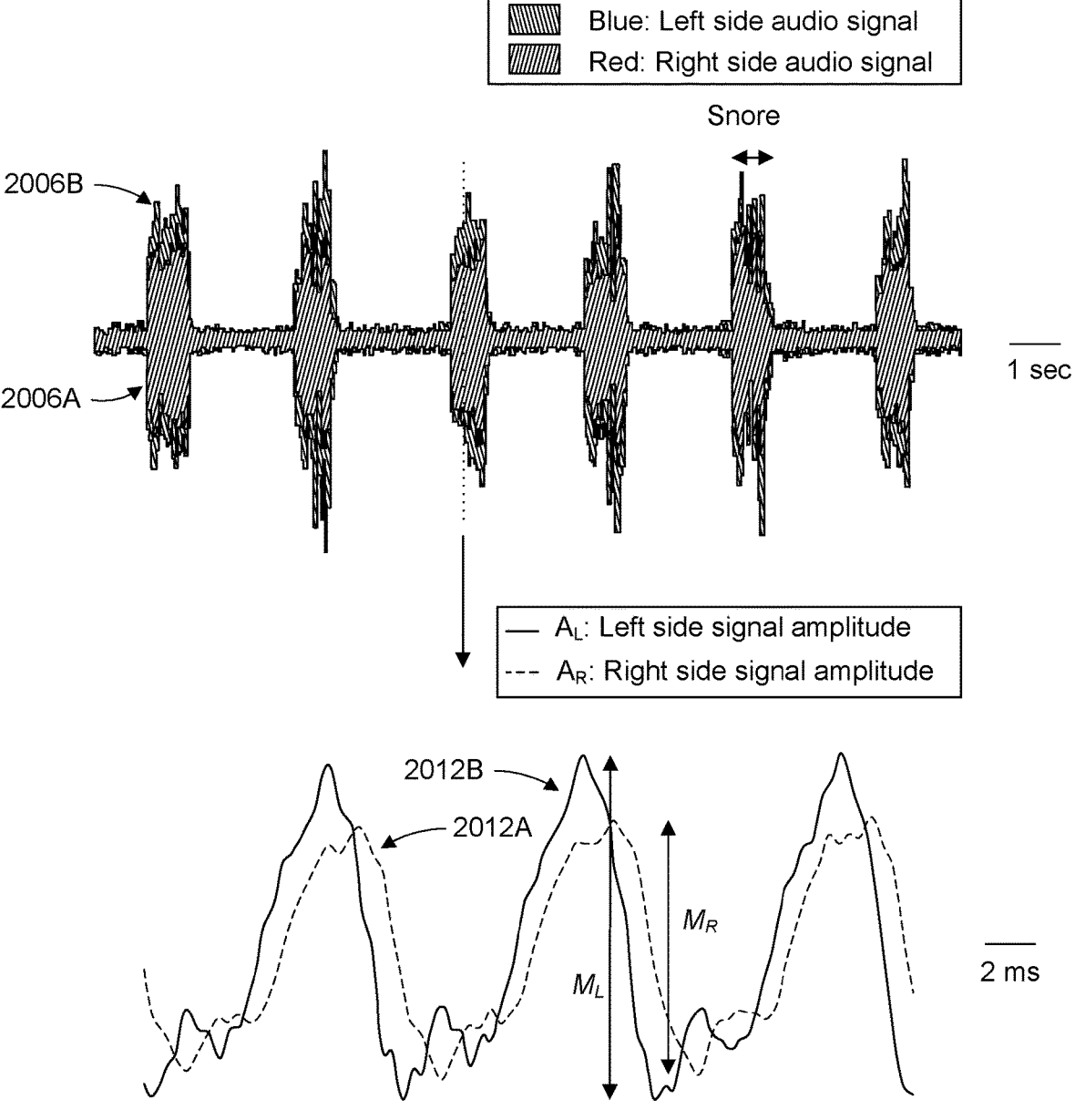
Figure 21A:
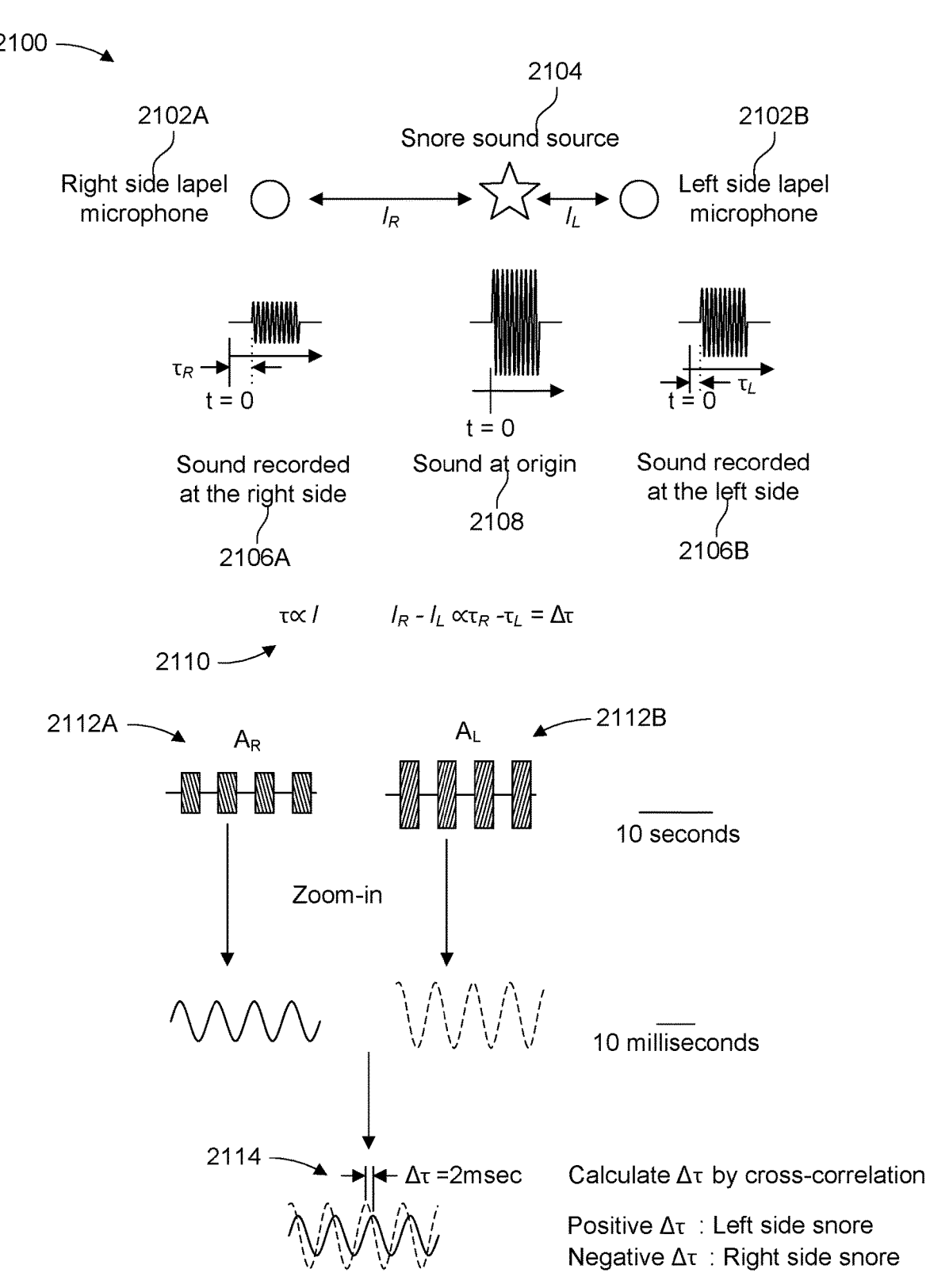
FIGS. 21A-B illustrate an example process for detecting snorer side based on assessing time-delay of acoustic readings.
Figure 21B:
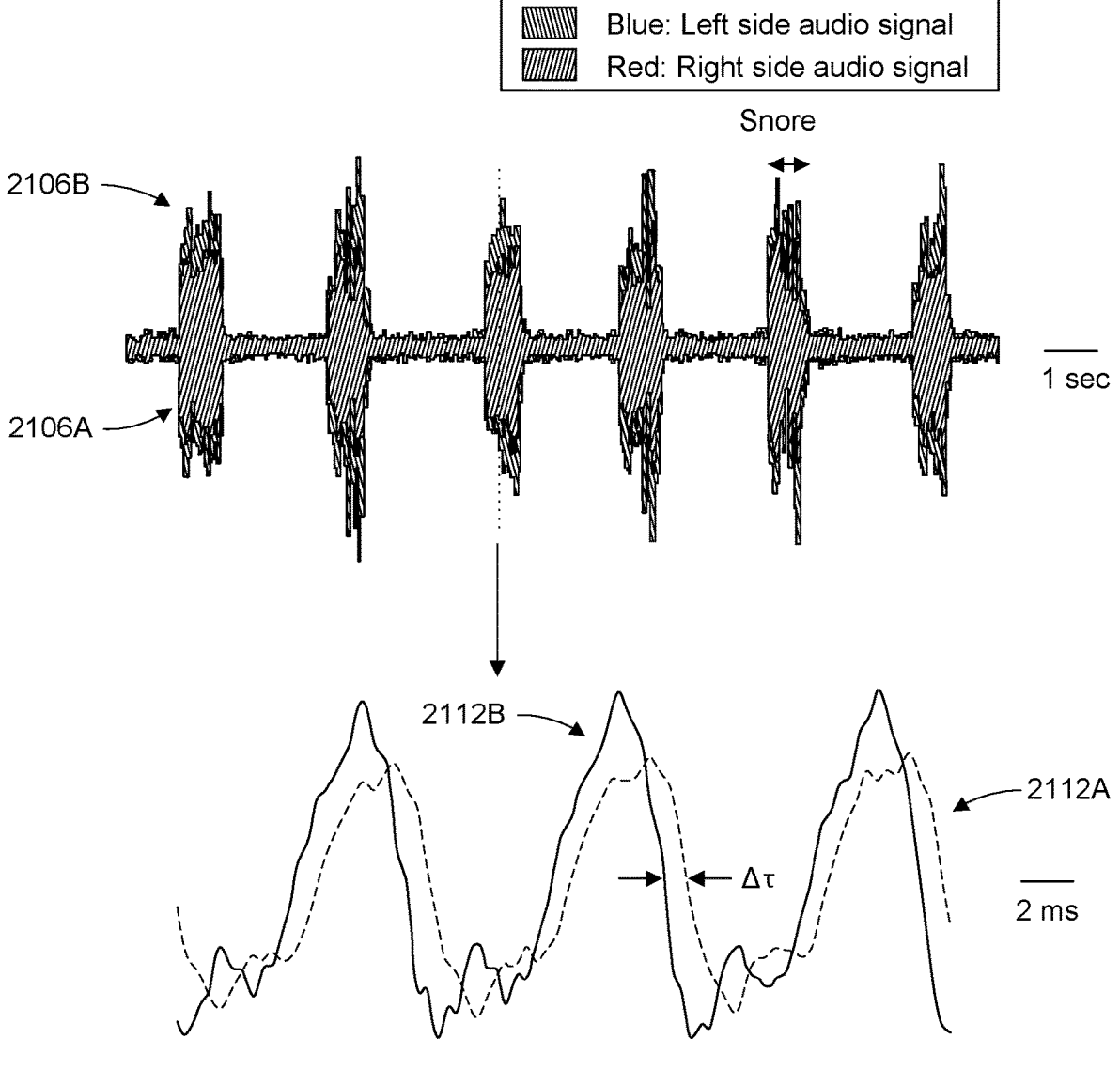
Figure 22A:
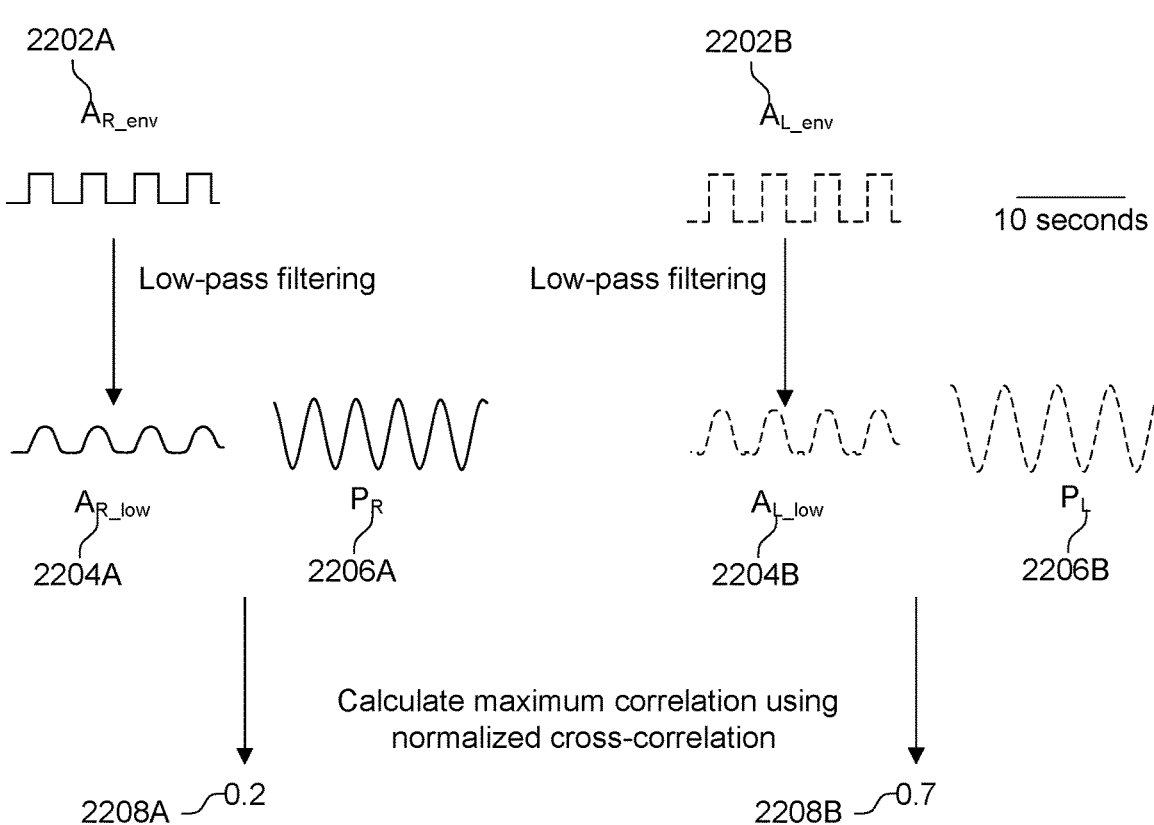
FIGS. 22A-B illustrate example processes for detecting snorer side based on assessing synchronized behavior of acoustic and pressure readings.
Figure 22B:
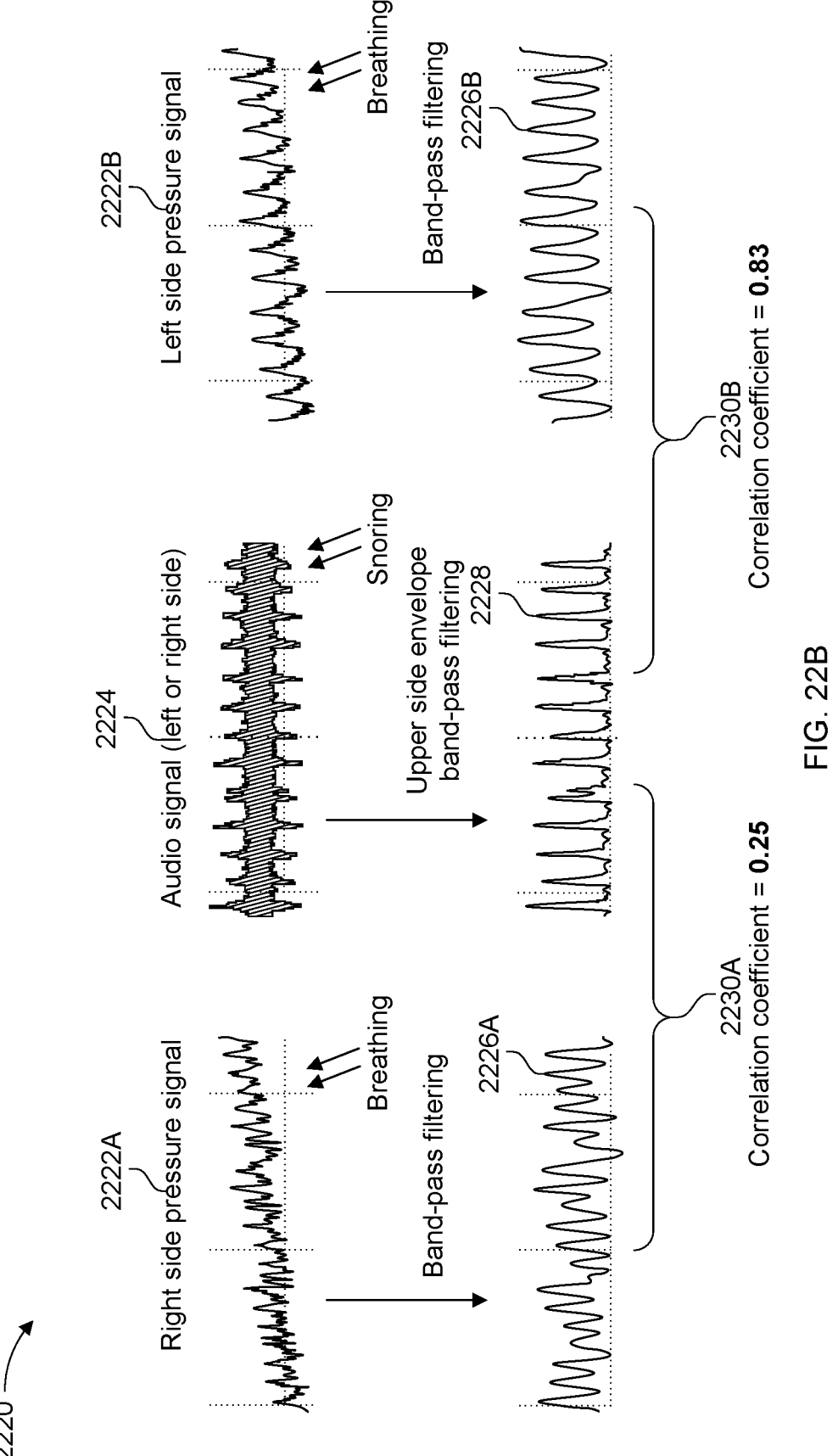
Figure 27:
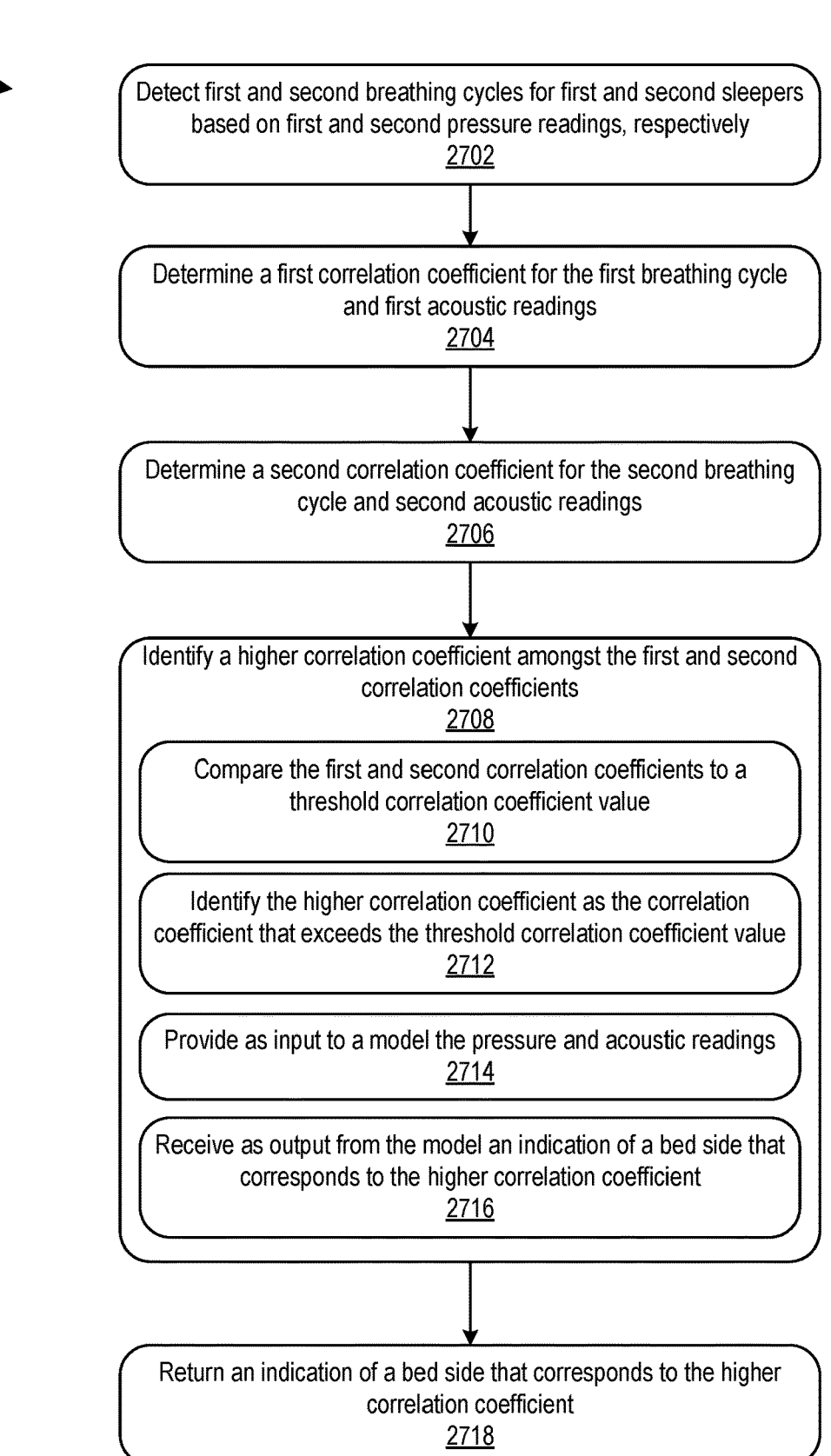
FIG. 27 is a flowchart of a process for detecting snorer side at a bed system based on assessing synchronized behavior of acoustic and pressure readings. Like reference symbols in the various drawings indicate like elements.

The computer system 1910 can determine which of the sides 1908A and 1908B of the bed system 1902 has the snoring event (block E, 1928). The computer system 1910 can implement any of the techniques described in reference to FIGS. 20-22 and FIGS. 25-27 in order to determine the snorer side at the bed system 1902. For example, as described further below, the computer system 1910 can determine the snorer side based on assessing amplitudes of the acoustic readings to determine whether one of the acoustic readings is stronger on one side of the bed system 1902 and therefore indicative of the snorer side. Refer to FIGS. 20A-B and 25. As another example, the computer system 1910 can determine the snorer side based on assessing time-delays of the acoustic readings to determine and identify which acoustic sensor picks up a sound indicative of the snoring event first. Signal processing techniques can be used, for example, to identify phase differences between the acoustic readings generated for each side of the bed system 1902 to then identify the snorer side. Refer to FIGS. 21A-B and 26. As yet another example, the computer system 1910 can determine the snorer side based on jointly assessing acoustic and pressure readings. Refer to FIGS. 22A-B and 27.

Accordingly, the computer system 1910 can generate and return output about the detected snoring event in block F (1930). Refer to FIG. 24 for further discussion about generating and returning the output, which can include actions to be performed at the bed system 1902 to alleviate the detected snoring event and/or indications of the snorer side at the bed system 1902.

FIGS. 20A-B illustrate an example process 2000 for detecting snorer side based on assessing amplitude of acoustic readings. The process 2000 can be performed by the computer system 1910. The process 2000 can also be performed by any other computing system, computing device, edge computing device, network of devices/systems, cloud-based system, and/or component of a bed system described herein (e.g., a controller of the bed system). For illustrative purposes, the process 2000 is described from the perspective of a computer system.

Referring to the process 2000 in both FIGS. 20A and 20B, amplitude of sound decreases as it propagates through air. A right-side microphone 2002A or other acoustic sensor described herein can collect acoustic readings 2006A. A left-side microphone 2002B or other acoustic sensor described herein can collect acoustic readings 2006B. The acoustic readings 2006A and 2006B can include sound that is recorded at each of the respective sides of the bed system described herein when a snore sound source 2004 is resting on the bed system. The snore sound source 2004 can generate a sound 2008. Using the disclosed techniques, the computer system can determine which of the acoustic readings 2006A and 2006B is most similar to the sound 2008 based on assessing amplitudes of the acoustic readings 2006A and 2006B to determine the snorer side of the bed system. For example, the computer system can implement a formula 2010 to determine a right-side amplitude 2012A and a left-side amplitude 2012B from a right-side audio signal 2013A and a left side audio signal 2013B. In some implementations, the formula 2010 can be performed by a machine learning-trained model that receives the acoustic readings 2006A and 2006B from the microphones 2002A and 2002B.

Once the amplitudes 2012A and 2012B are determined, the computer system can perform an envelope calculation to identify which of the acoustic readings 2006A and 2006B has an amplitude most similar to the origin sound 2008 (e.g., a highest amplitude) and thus determine which side of the bed system the snore originates from (2014). In some implementations, for example, a positive amplitude post-envelope calculation can indicate a left-side snore while a negative amplitude post-envelope calculation can indicate a right-side snore. In the example of FIGS. 20A-B, the acoustic readings 2006B from the left side of the bed system has the amplitude 2012B that is higher than the amplitude 2012A of the acoustic readings 2006A from the right side of the bed system, thereby indicating that the left side of the bed system is the snorer side. After all, when the left side sleeper snores, the left side sound amplitude is larger than the right side sound amplitude, because the sound travels a shorter distance to the left-side microphone 2002B than to the right side microphone 2002A. Similarly, if right side sleeper snores, then right side sound amplitude is larger than the left side sound amplitude.

FIGS. 21A-B illustrate an example process 2100 for detecting snorer side based on assessing time-delay of acoustic readings. The process 2100 can be performed by the computer system 1910. The process 2100 can also be performed by any other computing system, computing device, edge computing device, network of devices/systems, cloud-based system, and/or component of a bed system described herein (e.g., a controller of the bed system). For illustrative purposes, the process 2100 is described from the perspective of a computer system.

Referring to the process 2100 in both FIGS. 21A and 21B, sound travels approximately 340 meters per second, and there is time-delay in sound recordings, which can be considered a time for sound propagation to acoustic sensors. When a left side sleeper snores, for example, the sound can be recorded earlier by a left-side microphone 2102B than a right-side microphone 2102A due to shorter propagation distance. If, on the other hand, a right side sleeper snores, then the sound can be recorded earlier by the right-side microphone 2002A.

Accordingly, the right-side microphone 2102A or other acoustic sensor described herein can collect acoustic readings 2106A. The left-side microphone 2102B or other acoustic sensor described herein can collect acoustic readings 2106B. The acoustic readings 2106A and 2106B can include sound that is recorded at each of the respective sides of the bed system described herein when a snore sound source 2104 is resting on the bed system. The snore sound source 2104 can generate a sound 2108. Using the disclosed techniques, the computer system can determine which of the acoustic readings 2106A and 2106B has a shortest or earliest time-delay relative the origin sound 2108 based on assessing time-delays of the acoustic readings 2106A and 2106B to then determine the snorer side of the bed system. For example, the computer system can implement a formula 2110 to determine a right-side amplitude 2112A and a left-side amplitude 2112B. In some implementations, the formula 2110 can be performed by a machine learning-trained model that receives the acoustic readings 2106A and 2106B from the microphones 2102A and 2102B.

Once the amplitudes 2112A and 2112B are determined, the computer system can identify which of the acoustic readings 2106A and 2106B has a shortest or earliest time-delay relative the origin sound 2108 and thus determine which side of the bed system the snore originates from (2114). For example, the computer system can calculate or determine a change in time between the right-side and left-side amplitudes 2112A and 2112B by cross-correlation. In some implementations, a positive change in time can indicate a left-side snore while a negative change in time can indicate a right-side snore. In the example of FIGS. 21A-B, the acoustic readings 2106B from the left side of the bed system has a shorter or earlier time-delay than the acoustic readings 2106A from the right side of the bed system, thereby indicating that the left side of the bed system is the snorer side.

FIGS. 22A-B illustrate example processes 2200 and 2220 for detecting snorer side based on assessing synchronized behavior of acoustic and pressure readings. The processes 2200 and 2220 can be performed by the computer system 1910. The processes 2200 and 2220 can also be performed by any other computing system, computing device, edge computing device, network of devices/systems, cloud-based system, and/or component of a bed system described herein (e.g., a controller of the bed system). For illustrative purposes, the processes 2200 and 2220 are described from the perspective of a computer system.

Referring to the processes 2200 and 2220 in both FIGS. 22A and 22B, snore sounds can be generated when breathing air flow is disturbed at a certain period of a respiration cycle. Consequently, snore events can be synchronized with respiration cycles. Sleeper respiration cycles can be extracted from each side (left and/or right) pressure readings by each side pressure sensors. When a left side sleeper snores, for example, an acoustic reading indicative of a snore signal (left or right, or both left and right acoustic readings) can be synchronized with the left side respiration cycle identified from the left side pressure readings. Similarly, if a right side sleeper snores, the acoustic reading can be synchronized with the right side respiration cycle identified from the right side pressure readings. Therefore, the snorer side can be detected by identifying whether the acoustic reading indicative of the snore signal is synchronized with the left side respiration cycle or the right side respiration cycle.

Referring to the process 2200 in FIG. 22A, right side and left side acoustic readings 2202A and 2202B can be processed by the computer system using low-pass filtering techniques to generate processed right side and left side acoustic readings 2204A and 2204B, respectively. In some implementations, the amplitude signals 2012A and 2012B that were processed in the process 2000 using an envelope calculation (refer to FIG. 20A) can be processed using the low-pass filtering techniques in the process 2200.

The computer system also can receive right side and left side pressure readings 2206A and 2206B, respectively, as described herein. In some implementations, the computer system may also process the pressure readings 2206A and 2206B (e.g., band-pass filtering). The computer system can calculate maximum right side and left side correlation coefficients 2208A and 2208B, respectively, using normalized cross-correlation of the readings associated with each side of the bed system. For example, the right side correlation coefficient 2208A can be determined between the processed right side acoustic readings 2204A and the right side pressure readings 2206A. The left side correlation coefficient 2208B can be determined between the processed left side acoustic readings 2204A and the left side pressure readings 2206B.

The computer system can then compare the correlation coefficients 2208A and 2208B to determine the snorer side. The correlation coefficients 2208A and 2208B can be compared to each other to determine which of the determined correlation coefficients is higher, which can indicate the snorer side. The correlation coefficients 2208A and 2208B can be compared to one or more correlation coefficient criteria, such as one or more threshold correlation coefficient values and/or ranges. For example, if neither correlation coefficient is higher than a predetermined threshold correlation coefficient, the system can determine that neither sleeper is snoring. As another illustrative example, if the right side correlation coefficient 2208A is less than the left side correlation coefficient 2208B, then the snorer side is likely the left side of the bed system. If the right side correlation coefficient 2208A is greater than the left side correlation coefficient 2208B, then the snorer side is likely the right side of the bed system. In the example of FIG. 22A, the left side correlation coefficient 2208B is greater than the right side correlation coefficient 2208A, thereby indicating that the snorer side is the left side of the bed system.

Referring to the process 2220 in FIG. 22B, the computer system can receive right side pressure readings 2222A and left side pressure readings 2222B. The computer system can perform band-pass filtering techniques on the pressure readings 2222A and 2222B to generate processed right side and left side pressure readings 2226A and 2226B, respectively. The computer system can also receive left side and right side acoustic readings 2224 (e.g., audio signals) as described above. The acoustic readings 2224 can be processed by the computer system using an envelope calculation (e.g., upper side envelope calculation) and/or band-pass filtering techniques. For example, an envelope calculation can be applied to identify the outline of time series data. This can include identifying an upper envelope/outline of the top side of the acoustic readings and a lower envelope/outline of the acoustic readings. In some cases, the upper or lower envelope is selected and a low pass filter is applied to selected envelope. Accordingly the computer system can generate processed acoustic readings 2228. As described above, the computer system can determine right side and left side correlation coefficients 2230A and 2230B, respectively, between (i) the processed right side pressure readings 2226A and the processed acoustic readings 2228 and (ii) the processed left side pressure readings 2226B and the processed acoustic readings 2228. A higher correlation coefficient value can indicate the snorer side of the bed system. In the example of FIG. 22B, the left side correlation coefficient 2230B is a higher value than the right side correlation coefficient value 2230A. Therefore, the left side can be determined as the snorer side.

FIG. 23 illustrates an example process 2300 for processing acoustic and pressure readings that are received from acoustic and pressure readings at a bed system described herein. The process 2300 can be performed by the computer system 1910. The process 2300 can also be performed by any other computing system, computing device, edge computing device, network of devices/systems, cloud-based system, and/or component of a bed system described herein (e.g., a controller of the bed system). For illustrative purposes, the process 2300 is described from the perspective of a computer system.

The process 2300 can be performed before using the acoustic and/or pressure readings to detect the snorer side of the bed system. As described herein, the computer system can receive left side and right side audio readings 2302A-B, left side and right side pressure readings 2304A-B, or other sensor readings from respective sensors at the bed system. The received readings can be raw readings (e.g., not preprocessed before being transmitted to the computer system). The computer system can perform processing techniques 2306 and/or 2308, including but not limited to filtering, resampling, etc. in order to generate processed right side and left side acoustic readings 2310A and 2310B, respectively, which may indicate snore signals, and processed right side and left side pressure readings 2312A and 2312B indicative of respiration (e.g., breathing) cycles/signals. The processed readings 2310A, 2310B, 2312A, and 2312B can then be used by the computer system to perform the techniques described in reference to FIGS. 20-22 and FIGS. 25-27.

FIG. 24 is a flowchart of a process 2400 for detecting snorer side at a bed system described herein. The process 2400 can be performed by the computer system 1910. The process 2400 can also be performed by any other computing system, computing device, edge computing device, network of devices/systems, cloud-based system, and/or component of a bed system described herein (e.g., a controller of the bed system). For illustrative purposes, the process 2400 is described from the perspective of a computer system.

Referring to the process 2400 in FIG. 24, the computer system can receive pressure and/or audio readings from sensors at a bed system in block 2402. As described herein, the computer system can receive, from a first pressure sensor, first pressure readings indicative of sensed pressure at a first side of a mattress of the bed system where a first sleeper (e.g., first user) rests, receive, from a second pressure sensor, second pressure readings indicative of sensed pressure at a second side of the mattress where a second sleeper rests, receive, from a first acoustic sensor, first acoustic readings indicative of sensed acoustics from the first sleeper, and receive, from a second acoustic sensor, second acoustic readings indicative of sensed acoustics from the second sleeper.

In block 2404, the computer system can process the received readings. The computer system can process the readings as described in reference to FIG. 23.

The computer system can determine whether a bed entrance event is detected based on the processed readings in block 2406. Sometimes, block 2406 can be performed before block 2404. The computer system can detect the bed entrance event using one or more of the techniques described above. For example, based on processing the received readings, the computer system can determine that at least one of the first or second sleepers entered the bed system. Additionally or alternatively, based on processing the received readings, the computer system can determine that at least one of the first or second sleepers fell asleep. Additionally or alternatively, based on processing the received readings, the computer system can determine that at least one of the first or second sleepers moves less than a threshold amount of movement in the bed system. Any of these examples are indicative of the bed entrance event.

If a bed entrance event is not detected, the computer system returns to block 2402. The computer system can continue to monitor the bed system until the bed entrance event is detected. If a bed entrance event is detected, the computer system proceeds to block 2408.

The computer system can determine, in block 2408, which snore detection algorithm criteria is satisfied by the processed readings. The computer system can determine whether any one or more of the processed readings exceed or otherwise satisfy respective threshold quality levels. Based on the determination in block 2408, the computer system can perform one of blocks 2410, 2412, or 2414. For example, the computer system can determine that at least one of the processed pressure readings does not satisfy threshold pressure quality levels. As a result, the computer system can determine that either blocks 2410 or 2412 should be performed to detect the snorer side. As another example, if the computer system determines that the pressure readings and the acoustic readings satisfy respective threshold quality levels, then the computer system can determine that block 2414 should be performed to detect the snorer side. For example, the system can use cross-correlation to measure similarities between time series signals. The system normalizes each of the measured time series signals and then time shifts one or more of the signals such that the signals align. The system can use a time-delay method to determine a difference of time delay as the amount of time shift at the moment of the maximum correlation value. In another example, the system can use a synchronicity method in which the correlation value between audio and pressure is the maximum value from normalized cross-correlation within +a few milliseconds shift boundaries.

In some implementations, a machine-learning model is used to detect the snore side using multiple inputs. For example, multiple detection methods can be fed into the machine-learning model and each of the multiple detection methods will contribute to the snoring side detection. The portion of contribution of each is determined by the machine-learning model at each side detection moment. Inputs to this machine-learning model can include a left side audio envelope (amplitude), a right side audio envelope (amplitude), left and right audio time-delay difference, left audio-pressure correlation coefficient, and/or right audio-pressure correlation coefficient.

In block 2410, the computer system can detect snorer side based on amplitude of the processed acoustic readings. Refer to FIG. 25 for further discussion.

In block 2412, the computer system can detect snorer side based on time-delay of the processed acoustic readings. Refer to FIG. 26 for further discussion.

In block 2414, the computer system can detect the snorer side based on synchronization of the processed acoustic and pressure readings. Refer to FIG. 27 for further discussion.

After the computer system performs one of blocks 2410, 2412, and 2414, the computer system proceeds to block 2416, in which the computer system generates an action and/or indication based on the detected snorer side. The action can include, for example, generating instructions that cause a controller of the bed system to (i) automatically raise a head portion of the side of the bed system where the one of the first and second sleeper is snoring; (ii) automatically tilt a portion of a foundation of the bed system that corresponds to the side of the bed system where the one of the first and second sleepers is snoring; (iii) automatically vibrate a portion of a foundation of the bed system that corresponds to the side of the bed system where the one of the first and second sleepers is snoring; (iv) automatically provide an outside visual/light stimulus on a side of the bed system where the one of the first and second sleepers is snoring; and/or (v) automatically provide an auditory stimulus on a side of the bed system where the one of the first and second sleepers is snoring.

The computer system then returns the action and/or indication in block 2418. For example, the computer system can transmit the instructions to the controller or other components of the bed system to automatically perform the action. The computer system can store the action and/or indication in a data store. The computer system can provide the action and/or indication in a notification or message to one or more computing devices, such as a mobile device of at least one of the first and second sleepers. The mobile device can be configured to present the notification or message in a graphical user interface (GUI) display so that the respective sleeper can view information about when snoring was detected, how long the snoring lasted, and/or who was snoring. Other information about the detected snoring event can also be provided to the sleeper at their respective device.

In some implementations, in response to generating the action in block 2416, the computer system can continuously perform one or more of the blocks 2402-2416. For example, the computer system can continuously perform the blocks 2402-2416 until the computer system determines, based on processing at least one of the received readings, that at least one of the first or second sleepers (i) exits the bed system, (ii) wakes up, and/or (iii) experiences at least a threshold level of movement. Thus, the computer system can continue detecting snoring events and snorer side at the bed system until a bed exit event is detected.

In yet some implementations, the computer system may determine that both the first and second sleepers are snoring. This determination can be made based on assessing and identifying snore sounds or pitches that are unique to each sleeper. For example, the computer system can identify a first audio pitch in the first acoustic readings, identify a second audio pitch in the second acoustic readings, determine whether the first and second audio pitches indicate a same snore event based on comparing the first and second audio pitches, determine that the first and second audio pitches represent first and second snore events of the first and second users, respectively, based on a determination that the first and second audio pitches do not indicate the same snore event, and return an indication that the first and second sleepers are snoring. Determining that both sleepers are snoring can include comparing the first and second audio pitches to one or more threshold values to determine that the first and second audio pitches each meet or exceed the threshold indicative of snoring. The computer system may also generate at least one action in response to the indication that the first and second sleepers are snoring. The action can include generating instructions that cause the controller of the bed system to automatically adjust at least one side of the bed system. The computer system can generate actions to adjust only one side of the bed system. The computer system can generate actions to adjust both sides of the bed system. In some implementations, the computer system can generate actions to adjust both sides of the bed system in a same way. In some implementations, the computer system can generate actions to adjust each side of the bed system differently.

The process 2400 can be performed in real-time. The process 2400 can also be performed in near real-time (e.g., several seconds delay). Performing the process 2400 in real-time or near real-time allows for actions to be generated and taken in response to detecting the snoring event and the snorer side. Moreover, once action is taken in response to the detected snoring event at the snorer side the process 2400 can continue to be performed in order to adjust the bed system one or more additional times (e.g., return the bed system to settings before the bed was initially adjusted based on determining that the snoring event has ended, adjust the bed system to sleeper-desired settings based on determining that the snoring event has ended).

FIG. 25 is a flowchart of a process 2500 for detecting snorer side at a bed system based on assessing amplitude of acoustic readings. As described herein, the closer in distance an acoustic sensor is to a location or origin of a snore sound, the higher or larger an amplitude of acoustic readings generated by that acoustic sensor, which indicates a side of the bed system where the snore originates from. In some implementations, the process 2500 can be performed based on a determination that at least one of the pressure readings received in the process 2400 of FIG. 24 does not exceed or satisfy threshold pressure quality levels. As another example, the process 2500 can be performed based on determining that acoustic sensors are positioned in accurate positions on a frame or foundation of the bed system near respective first and second sleepers. The process 2500 is similar or the same as the process 2000 described in FIGS. 20A-B. The process 2500 can be performed as part of block 2410 in the process 2400 of FIG. 24.

The process 2500 can be performed by the computer system 1910. The process 2500 can also be performed by any other computing system, computing device, edge computing device, network of devices/systems, cloud-based system, and/or component of a bed system described herein (e.g., a controller of the bed system). For illustrative purposes, the process 2500 is described from the perspective of a computer system.

Referring to the process 2500 in FIG. 25, the computer system determines a first amplitude of first acoustic readings indicative of sensed acoustics of a first sleeper in block 2502.

In block 2504, the computer system can determine a second amplitude of second acoustic readings indicative of sensed acoustics of a second sleeper.

The computer system can identify a higher amplitude amongst the first and second amplitudes in block 2506. The higher amplitude can indicate that one of the first and second sleepers is snoring.

For example, the computer system can compare the first and second amplitudes to a threshold amplitude level (block 2508) and then identify the higher amplitude as the amplitude that exceeds the threshold amplitude level (block 2510).

As another example, the computer system can provide, as input to a model, the first and second acoustic readings (block 2512) and receive, as output from the model, an indication of a bed side that corresponds to the higher amplitude (block 2514). The model can be trained with machine learning techniques to determine the first and second amplitudes and identify the higher amplitude based on comparing the first and second amplitudes with each other and/or against one or more threshold amplitude levels, values, and/or ranges. In yet some implementations, the model can be trained to: determine a first amplitude of a first portion of the acoustic readings, the first portion of the readings corresponding to a first side of the bed system where the first sleeper rests, determine a second amplitude of a second portion of the acoustic readings, the second portion of the readings corresponding to a second side of the bed system where the second sleeper rests, and detect a snore event based on identifying the higher amplitude amongst the first and second amplitudes.

The computer system can return the bed side that corresponds to the higher amplitude in block 2516. In other words, the computer system can return an indication of the snorer side of the bed system, which is a side of the bed system where the first or second sleeper is snoring. In some implementations, after block 2516, the computer system can proceed to block 2416 in the process 2400 of FIG. 24.

FIG. 26 is a flowchart of a process 2600 for detecting snorer side at a bed system based on assessing time-delay of acoustic readings. As described herein, sound arrives faster or earlier at a side of the bed system where an acoustic sensor is closest to a head of a snoring sleeper. Although a same wavelength of the acoustic readings may be identified by acoustic sensors at both sides of the bed system, a time-delay can be measured for each of the acoustic sensors. An acoustic reading having a shorter or earlier time-delay can indicate a snorer side at the bed system.

In some implementations, the process 2600 can be performed based on a determination that at least one of the pressure readings received in the process 2400 of FIG. 24 does not exceed or satisfy threshold pressure quality levels. In some implementations, the process 2600 can be performed based on a determination that acoustic sensors are configured to a mattress of the bed system, which can provide for accurate detection of acoustic readings closest to heads of first and second sleepers at the bed system. The process 2600 is similar or the same as the process 2100 described in FIGS. 21A-B. The process 2600 can be performed as part of block 2412 in the process 2400 of FIG. 24.

The process 2600 can be performed by the computer system 1910. The process 2600 can also be performed by any other computing system, computing device, edge computing device, network of devices/systems, cloud-based system, and/or component of a bed system described herein (e.g., a controller of the bed system). For illustrative purposes, the process 2600 is described from the perspective of a computer system.

Referring to the process 2600, the computer system can determine a first time that a peak is detected in first acoustic readings indicating of sensed acoustics of a first sleeper (block 2602). The peak can indicate a snore.

The computer system can determine a second time that the peak is detected in second acoustic readings indicative of sensed acoustics of a second sleeper (block 2604).

In block 2606, the computer system can identify an earlier time amongst the first and second times. The earlier time can indicate that one of the first and second sleepers is snoring.

For example, the computer system can compare the first and second times (block 2608) and identify the earlier time as the time that is less than a threshold time value and/or range (block 2610).

As another example, the computer system can provide, as input to a model, the first and second acoustic readings (block 2612) and then receive, as output, from the model, an indication of a bed side that corresponds to the earlier time (block 2614). The model can be trained to determine the first and second times and identify the earlier time based on comparing the first and second times. As another example, the model can be trained with machine learning techniques to determine a first time of a first portion of the acoustic readings at which a peak is detected, the peak indicating a snore and the first portion of the readings corresponding to a first side of the bed system where the first sleeper rests, determine a second time of a second portion of the acoustic readings at which the peak is detected, the second portion of the readings corresponding to a second side of the bed system where the second sleeper rests, and detect the snore event based on identifying an earlier time amongst the first and second times.

In block 2616, the computer system can return an indication of the bed side that corresponds to the earlier time. The indication can indicate the snorer side at the bed system where one of the first and second sleepers is snoring. In some implementations, after block 2616, the computer system can proceed to block 2416 in the process 2400 of FIG. 24.

FIG. 27 is a flowchart of a process 2700 for detecting snorer side at a bed system based on assessing synchronized behavior of acoustic and pressure readings. In some implementations, the process 2700 can be performed based on a determination that both pressure and acoustic readings in the process 2400 of FIG. 24 exceed or satisfy threshold pressure and acoustic quality levels. The process 2700 is similar or the same as the processes 2200 and 2220 described in FIGS. 22A-B. The process 2700 can be performed as part of block 2414 in the process 2400 of FIG. 24.

The process 2700 can be performed by the computer system 1910. The process 2700 can also be performed by any other computing system, computing device, edge computing device, network of devices/systems, cloud-based system, and/or component of a bed system described herein (e.g., a controller of the bed system). For illustrative purposes, the process 2700 is described from the perspective of a computer system.

Referring to the process 2700, the computer system can detect first and second breathing cycles for first and second sleepers based on first and second pressure readings, respectively (block 2702). Detecting the first and second breathing cycles for the first and second sleepers, respectively, can include applying band-pass filtering techniques to each of the first and second pressure readings. The band-pass filtering techniques can be applied around breathing frequencies (e.g., known for either of the first and second sleepers, generic for a population of sleepers). In other words, the computer system can synchronize a first portion of the pressure readings with a first portion of the acoustic readings, the first portion of the readings corresponding to a first side of the bed system where the first sleeper rests. The computer system can also synchronize a second portion of the pressure readings with a second portion of the acoustic readings, the second portion of the readings correspond to a second side of the bed system where the second sleeper rests.

In block 2704, the computer system can determine a first correlation coefficient for the first breathing cycle and first acoustic readings. Determining the first correlation coefficient further can include synchronizing the first breathing cycle with the first acoustic readings. The computer system can determine the first correlation coefficient between the synchronized first readings. The computer system can determine the second correlation coefficient between the synchronized second readings.

In block 2706, the computer system can determine a second correlation coefficient for the second breathing cycle and second acoustic readings. Determining the second correlation coefficient further can include synchronizing the second breathing cycle with the second acoustic readings.

The computer system can identify a higher correlation coefficient amongst the first and second correlation coefficients (block 2708). The higher correlation coefficient can indicate that one of the first and second sleepers is snoring.

For example, the computer system can compare the first and second correlation coefficients to a threshold correlation coefficient value (block 2710) and identify the higher correlation coefficient as the correlation coefficient that exceeds the threshold correlation coefficient value (block 2712). In some cases, neither correlation coefficient will exceed the threshold correlation coefficient, in which case the system will determine that neither sleeper is snoring. In some cases, both correlation coefficients will exceed the threshold correlation coefficient, in which case the system will determine that both sleepers are snoring and take corrective actions to alleviate snoring for both sleepers by adjusting an aspect of the sleep environment as described above.

As another example, the computer system can provide, as input to a model, the pressure and acoustic readings (or other sensor readings) (block 2714). Sometimes, the computer system can provide the first breathing cycle, the first acoustic readings, the second breathing cycle, and the second acoustic readings to the model as input. The computer system can then receive, as output from the model, an indication of a bed side that corresponds to the higher correlation coefficient (block 2716). The computer system can receive, as output, from the model, the higher correlation coefficient. The model can be trained with machine learning techniques to determine the first and second correlation coefficients and compare the first and second correlation coefficients to identify the higher correlation coefficient.

The computer system can return an indication of the bed side that corresponds to the higher correlation coefficient (block 2718). The indication indicates the side of the bed system where the one of the first and second sleeper is snoring. In some implementations, after block 2718, the computer system can proceed to block 2416 in the process 2400 of FIG. 24. In response to the indication, the sleep system can automatically adjust an aspect of the sleep environment to alleviate the snoring of the sleeper on the detected snoring side. For example, the sleep system can automatically adjust a vertical inclination of a head portion of the side of the sleep system supporting the snoring sleeper, cause a portion of the sleep system supporting the snoring sleeper to vibrate, provide audio, visual, or tactile stimulation to the snoring sleeper, or otherwise stimulate the snoring sleeper, without providing simulation to the non-snoring sleeper, to attempt to alleviate snoring of the detected snoring sleeper.

What is claimed is:

1. A bed system comprising:
a mattress having a first side to support a first user and a second side to support a second user;
a first pressure sensor proximate the first side of the mattress configured to sense pressure applied to the first side of the mattress;
a second pressure sensor proximate the second side of the mattress configured to sense pressure applied to the second side of the mattress;
a first acoustic sensor proximate the first side of the mattress configured to sense acoustics from the first user on the first side of the mattress;
a second acoustic sensor proximate the second side of the mattress configured to sense acoustics from the second user on the second side of the mattress; and
a computer system in data communication with the first pressure sensor, the second pressure sensor, the first acoustic sensor, and the second acoustic sensor, wherein the computer system is configured to:
    receive, from the first pressure sensor, first pressure readings indicative of the sensed pressure at the first side of the mattress;
    receive, from the second pressure sensor, second pressure readings indicative of the sensed pressure at the second side of the mattress;
    receive, from the first acoustic sensor, first acoustic readings indicative of the sensed acoustics from the first user;
    receive, from the second acoustic sensor, second acoustic readings indicative of the sensed acoustics from the second user;
    detect, based on the first and second pressure readings, first and second breathing cycles for the first and second users, respectively;
    determine a first correlation coefficient for the first breathing cycle and the first acoustic readings;
    determine a second correlation coefficient for the second breathing cycle and the second acoustic readings;
    identify a higher correlation coefficient amongst the first and second correlation coefficients, wherein the higher correlation coefficient indicates that one of the first and second users is snoring; and
    return an indication of a side of the bed system that corresponds to the higher correlation coefficient, wherein the indication indicates the side of the bed system where the one of the first and second users is snoring.

2. The bed system of claim 1, wherein identifying the higher correlation coefficient comprises:
providing, as input to a machine learning-trained model, the first breathing cycle, the first acoustic readings, the second breathing cycle, and the second acoustic readings; and
receiving, as output from the model, an indication of the higher correlation coefficient, wherein the model was trained to determine the first and second correlation coefficients and compare the first and second correlation coefficients to identify the higher correlation coefficient.

3. The bed system of claim 1, wherein identifying the higher correlation coefficient comprises:
comparing the first and second correlation coefficients to a threshold correlation coefficient value; and
identifying the higher correlation coefficient as one of the first and second correlation coefficients that exceeds the threshold correlation coefficient value.

4. The bed system of claim 1, wherein: determining the first correlation coefficient further comprises synchronizing the first breathing cycle with the first acoustic readings, and determining the second correlation coefficient further comprises synchronizing the second breathing cycle with the second acoustic readings.

5. The bed system of claim 1, wherein detecting the first and second breathing cycles for the first and second users, respectively, comprises applying band-pass filtering techniques to each of the first and second pressure readings.

6. The bed system of claim 1, wherein the computer system is configured to perform the detecting, determining, identifying, and returning steps based on: processing the received readings; and determining that each of the processed readings exceed respective threshold quality levels.

7. The bed system of claim 6, wherein, in response to determining that at least one of the processed first or second pressure readings does not exceed the respective threshold quality levels, the computer system is configured to:
determine a first amplitude of the first acoustic readings;
determine a second amplitude of the second acoustic readings;
identify a higher amplitude amongst the first and second amplitudes, wherein the higher amplitude indicates that one of the first and second users is snoring; and
return the indication of the side of the bed system that corresponds to the higher amplitude, wherein the indication indicates the side of the bed system where the one of the first and second users is snoring.

8. The bed system of claim 6, wherein, in response to determining that at least one of the processed first or second pressure readings does not exceed the respective threshold quality levels, the computer system is configured to:
determine a first time that a peak is detected in the first acoustic readings, wherein the peak indicates a snore;
determine a second time that the peak is detected in the second acoustic readings;
identify an earlier time amongst the first time and the second time, wherein the earlier time indicates that one of the first and second users is snoring; and
return the indication of the side of the bed system that corresponds to the earlier time, wherein the indication indicates the side of the bed system where the one of the first and second users is snoring.

9. The bed system of claim 1, wherein the computer system is further configured to generate an action in response to the indication of the side of the bed system where the one of the first and second users is snoring, wherein the action comprises generating instructions that cause a controller of the bed system to (i) automatically raise a head portion of the side of the bed system where the one of the first and second users is snoring or (ii) automatically tilt a portion of a foundation of the bed system that corresponds to the side of the bed system where the one of the first and second users is snoring.

10. The bed system of claim 9, wherein, in response to generating the action, the computer system is configured to continuously perform the receiving, detecting, determining, identifying, and returning steps.

11. The bed system of claim 10, wherein the computer system is configured to continuously perform the steps until the computer system determines, based on processing at least one of the received readings, that at least one of the first or second users (i) exits the bed system, (ii) wakes up, or (iii) experiences at least a threshold level of movement.

12. The bed system of claim 1, wherein the computer system is configured to perform the detecting, determining, identifying, and returning steps in response to determining, based on processing at least one of the received readings, that at least one of the first or second users (i) entered the bed system or (ii) fell asleep.

13. The bed system of claim 1, wherein the computer system is a controller of the bed system.

14. The bed system of claim 1, wherein the computer system is remote from the bed system.

15. The bed system of claim 1, wherein the bed system further comprises a foundation, wherein the first acoustic sensor is integrated into a first side of the foundation and the second acoustic sensor is integrated into a second side of the foundation, the second side of the foundation being opposite the first side, wherein the first side is configured to support the first user and the second side is configured to support the second user.

16. The bed system of claim 1, wherein the first and second acoustic sensors are integrated into at least one device that is positioned near the bed system, the at least one device being at least one of a mobile phone, smartphone, wearable device, laptop, tablet, or home automation device.

17. The bed system of claim 1, wherein the computer system is further configured to determine that both the first and second users are snoring based on:

identifying a first audio pitch in the first acoustic readings;
identifying a second audio pitch in the second acoustic readings;
determining whether the first and second audio pitches indicate a same snore event based on comparing the first and second audio pitches;
determining that the first and second audio pitches represent first and second snore events of the first and second users, respectively, based on a determination that the first and second audio pitches do not indicate the same snore event; and
returning an indication that the first and second users are snoring.

18. The bed system of claim 17, wherein the computer system is further configured to generate at least one action in response to the indication that the first and second users are snoring, wherein the action comprises generating instructions that cause a controller of the bed system to automatically adjust at least one side of the bed system.

19. A bed system configured to support a first user on a first side of the bed system and a second user on a second side of the bed system, the bed system comprising:

a first acoustic sensor positioned proximate the first side of the bed system configured to sense acoustics from the first user;
a second acoustic sensor positioned proximate the second side of the bed system configured to sense acoustics from the second user; and
a computer system in data communication with the first acoustic sensor and the second acoustic sensor, wherein the computer system is configured to:
receive, from the first acoustic sensor, first acoustic readings indicative of the sensed acoustics from the first user;
receive, from the second acoustic sensor, second acoustic readings indicative of the sensed acoustics from the second user;
determine a first amplitude of the first acoustic readings;
determine a second amplitude of the second acoustic readings;
identify a higher amplitude amongst the first and second amplitudes, wherein the higher amplitude indicates that one of the first and second users is snoring; and
return an indication of a side of the bed system that corresponds to the higher amplitude, wherein the indication indicates the side of the bed system where the one of the first and second users is snoring.

20. A bed system configured to support a first user on a first side of the bed system and a second user on a second side of the bed system, the bed system comprising:

a first acoustic sensor positioned proximate the first side of the bed system configured to sense acoustics from the first user;
a second acoustic sensor positioned proximate the second side of the bed system configured to sense acoustics from the second user; and
a computer system in data communication with the first acoustic sensor and the second acoustic sensor, wherein the computer system is configured to:
receive, from the first acoustic sensor, first acoustic readings indicative of the sensed acoustics from the first user;
receive, from the second acoustic sensor, second acoustic readings indicative of the sensed acoustics from the second user;
determine a first time that a peak is detected in the first acoustic readings, wherein the peak indicates a snore;
determine a second time that the peak is detected in the second acoustic readings;
identify an earlier time amongst the first time and the second time, wherein the earlier time indicates that one of the first and second users is snoring; and
return an indication of a side of the bed system that corresponds to the earlier time, wherein the indication indicates the side of the bed system where the one of the first and second users is snoring.

* * * * *